United States Patent
Demers et al.

(10) Patent No.: US 10,415,559 B2
(45) Date of Patent: Sep. 17, 2019

(54) PUMPING CASSETTE

(71) Applicant: DEKA Products Limited Partnership, Manchester, NH (US)

(72) Inventors: Jason A. Demers, Manchester, NH (US); Michael J. Wilt, Windham, NH (US); Kevin L. Grant, Litchfield, NH (US); James D. Dale, Nashua, NH (US); Brian D. Tracey, Litchfield, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 204 days.

(21) Appl. No.: 15/413,369

(22) Filed: Jan. 23, 2017

(65) Prior Publication Data
US 2017/0130705 A1    May 11, 2017

Related U.S. Application Data

(63) Continuation of application No. 15/056,701, filed on Feb. 29, 2016, now Pat. No. 9,550,018, which is a
(Continued)

(51) Int. Cl.
*F04B 43/06* (2006.01)
*A61M 1/16* (2006.01)
(Continued)

(52) U.S. Cl.
CPC ........... *F04B 43/06* (2013.01); *A61M 1/1037* (2013.01); *A61M 1/16* (2013.01); *A61M 1/1605* (2014.02);
(Continued)

(58) Field of Classification Search
CPC .... A61M 1/16; A61M 1/1605; A61M 1/1639; A61M 1/1664; A61M 1/1666;
(Continued)

(56) References Cited

U.S. PATENT DOCUMENTS 2,203,859 A    6/1940   Brednlin
2,339,876 A    1/1944   Phillips
(Continued)

FOREIGN PATENT DOCUMENTS

EP    0 288 145 A1    10/1988
EP    1 362 604 A1    11/2003
(Continued)

OTHER PUBLICATIONS

U.S. Appl. No. 15/415,748, filed Jan. 25, 2017, Gray et al.
(Continued)

*Primary Examiner* — Philip R Wiest
(74) *Attorney, Agent, or Firm* — Wolf, Greenfield & Sacks, P.C.

(57) ABSTRACT

A pump cassette is disclosed. The pump cassette includes a housing having at least, one fluid inlet line and at least one fluid outlet line. The cassette also includes at least one reciprocating pressure displacement membrane pump within the housing. The pressure pump pumps a fluid from the fluid inlet line to the fluid outlet line. A hollow spike is also included on the housing as well as at least one metering pump The metering pump is fluidly connected to the hollow spike on the housing and to a metering pump fluid line. The metering pump fluid line is fluidly connected to the fluid outlet line.

20 Claims, 108 Drawing Sheets

Related U.S. Application Data continuation of application No. 13/624,460, filed on Sep. 21, 2012, now Pat. No. 9,272,082, which is a continuation of application No. 11/871,680, filed on Oct. 12, 2007, now Pat. No. 8,273,049, application No. 15/413,369, which is a continuation-in-part of application No. 14/525,071, filed on Oct. 27, 2014, which is a continuation of application No. 13/657,628, filed on Oct. 22, 2012, now Pat. No. 8,870,549, which is a continuation of application No. 11/787,212, filed on Apr. 13, 2007, now Pat. No. 8,292,594.

(60) Provisional application No. 60/921,314, filed on Apr. 2, 2007, provisional application No. 60/904,024, filed on Feb. 27, 2007, provisional application No. 60/835,490, filed on Aug. 4, 2006, provisional application No. 60/792,073, filed on Apr. 14, 2006.

(51) Int. Cl.

| | | |
|---|---|---|
| *F04B 43/073* | (2006.01) | |
| *A61M 1/10* | (2006.01) | |
| *F17D 3/00* | (2006.01) | |
| *F04B 9/109* | (2006.01) | |
| *F04B 13/02* | (2006.01) | |
| *F04B 43/00* | (2006.01) | |
| *F04B 7/02* | (2006.01) | |
| *F04B 43/02* | (2006.01) | |
| *F04B 45/02* | (2006.01) | |
| *F04B 49/22* | (2006.01) | |
| *F04B 53/06* | (2006.01) | |
| *F04B 53/10* | (2006.01) | |
| *F04B 53/16* | (2006.01) | |
| *A61M 1/28* | (2006.01) | |
| *F04B 23/06* | (2006.01) | |
| *F04B 41/06* | (2006.01) | |
| *F04B 45/053* | (2006.01) | |

(52) U.S. Cl.
CPC ........ *A61M 1/1639* (2014.02); *A61M 1/1656* (2013.01); *A61M 1/1664* (2014.02); *A61M 1/1666* (2014.02); *A61M 1/287* (2013.01); *F04B 7/02* (2013.01); *F04B 9/109* (2013.01); *F04B 13/02* (2013.01); *F04B 23/06* (2013.01); *F04B 41/06* (2013.01); *F04B 43/00* (2013.01); *F04B 43/02* (2013.01); *F04B 43/073* (2013.01); *F04B 43/0733* (2013.01); *F04B 43/0736* (2013.01); *F04B 45/02* (2013.01); *F04B 45/0536* (2013.01); *F04B 49/22* (2013.01); *F04B 53/06* (2013.01); *F04B 53/10* (2013.01); *F04B 53/16* (2013.01); *F17D 3/00* (2013.01); *A61M 1/106* (2013.01); *A61M 1/1006* (2014.02); *A61M 1/1062* (2014.02); *A61M 1/1087* (2014.02); *A61M 1/1096* (2014.02); *A61M 2205/12* (2013.01); *A61M 2205/128* (2013.01); *A61M 2205/3317* (2013.01); *A61M 2205/3324* (2013.01); *A61M 2205/3368* (2013.01); *Y10T 137/0324* (2015.04); *Y10T 137/0379* (2015.04); *Y10T 137/2521* (2015.04); *Y10T 137/85978* (2015.04); *Y10T 137/86139* (2015.04)

(58) Field of Classification Search
CPC .. A61M 1/1037; A61M 1/1656; A61M 1/287; A61M 1/1006; A61M 1/1062; A61M 1/1087; A61M 1/1096; F04B 43/06; F04B 43/073; F04B 43/0733; F04B 43/0736; F04B 7/02; F04B 9/109; F04B 13/02; F04B 23/06
USPC ........................................................ 604/8
See application file for complete search history.

(56) References Cited

U.S. PATENT DOCUMENTS

| | | |
|---|---|---|
| 3,083,943 A | 4/1963 | Stewart et al. |
| RE27,849 E | 12/1973 | Wortman et al. |
| 4,222,127 A | 9/1980 | Donachy et al. |
| 4,781,535 A | 11/1988 | Frawley et al. |
| 5,098,262 A | 3/1992 | Wecker et al. |
| 5,242,384 A | 9/1993 | Robinson et al. |
| 5,349,896 A | 9/1994 | Delaney, III et al. |
| 5,476,368 A | 12/1995 | Rabenau et al. |
| 5,516,429 A | 5/1996 | Snodgrass et al. |
| 5,609,572 A | 3/1997 | Lang |
| 5,961,305 A | 10/1999 | Eek et al. |
| 6,165,154 A | 12/2000 | Gray et al. |
| 6,261,065 B1 | 7/2001 | Nayak et al. |
| 6,293,108 B1 | 9/2001 | Cho et al. |
| 6,295,918 B1 | 10/2001 | Simmons et al. |
| 6,435,844 B1 | 8/2002 | Fukami |
| 6,520,747 B2 | 2/2003 | Gray et al. |
| 6,655,257 B1 | 12/2003 | Meyer |
| 6,692,457 B2 | 2/2004 | Flaherty |
| 6,877,419 B2 | 4/2005 | Ohrle et al. |
| 6,949,079 B1* | 9/2005 | Westberg ................ A61M 1/30 210/258 |
| 7,044,432 B2 | 5/2006 | Beden et al. |
| 7,153,286 B2 | 12/2006 | Busby et al. |
| 7,232,418 B2 | 6/2007 | Neri et al. |
| 7,648,627 B2 | 1/2010 | Beden et al. |
| 7,798,997 B2 | 9/2010 | Kamen et al. |
| 8,029,454 B2 | 10/2011 | Kelly et al. |
| 8,105,265 B2 | 1/2012 | Demers et al. |
| 8,535,525 B2 | 9/2013 | Heyes et al. |
| 9,302,039 B2 | 4/2016 | Kelly et al. |
| 10,060,867 B2 | 8/2018 | Kamen et al. |
| 10,077,766 B2 | 9/2018 | Demers et al. |
| 2003/0194332 A1 | 10/2003 | Jahn et al. |
| 2004/0176724 A1 | 9/2004 | Kamen et al. |
| 2005/0069425 A1 | 3/2005 | Gray et al. |
| 2005/0095154 A1* | 5/2005 | Tracey ................... F04B 53/22 417/477.9 |
| 2005/0131332 A1* | 6/2005 | Kelly .................. A61M 1/1696 604/4.01 |
| 2005/0145010 A1 | 7/2005 | Vanderveen et al. |
| 2009/0076433 A1 | 3/2009 | Folden et al. |
| 2015/0265760 A1 | 9/2015 | Wilt et al. |
| 2016/0175505 A1 | 6/2016 | Demers et al. |
| 2017/0356435 A1 | 12/2017 | Gray |
| 2018/0361048 A1 | 12/2018 | Scarpaci et al. |

FOREIGN PATENT DOCUMENTS

| | | |
|---|---|---|
| GB | 1 508 116 A | 4/1978 |
| JP | 2002-113096 A | 4/2002 |
| JP | 2003-000706 A | 1/2003 |
| JP | 64-29267 B2 | 11/2018 |
| WO | WO 84/02473 A1 | 7/1984 |
| WO | WO 97/05913 A1 | 2/1997 |
| WO | WO 99/10028 A | 3/1999 |
| WO | WO 03/099353 A2 | 12/2003 |
| WO | WO 03/101510 A1 | 12/2003 |

OTHER PUBLICATIONS

U.S. Appl. No. 15/386,546, filed Dec. 21, 2016, Wilt et al.
U.S. Appl. No. 16/133,279, dated Sep. 17, 2018, Demers et al.
U.S. Appl. No. 15/960,426 filed, Apr. 23, 2018, Grant et al.
U.S. Appl. No. 15/619,961, filed Jun. 12, 2017, Wilt et al.

(56) References Cited

OTHER PUBLICATIONS

U.S. Appl. No. 16/112,375, filed Aug. 24, 2018, Kamen et al.
U.S. Appl. No. 14/525,071, filed Oct. 27, 2014, Tracey et al.
U.S. Appl. No. 16/207,349, filed Dec. 3, 2018, McGill et al.
U.S. Appl. No. 16/263,950, filed Jan. 31, 2019, Wilt et al.
U.S. Appl. No. 15/992,037, filed May 29, 2018, Scarpaci et al.
U.S. Appl. No. 15/199,204, filed Jun. 30, 2016, Wilt et al.
U.S. Appl. No. 15/445,683, filed Feb. 28, 2017, Wilt et al.
PCT/US2008/055000, dated Aug. 1, 2008, International Search Report and Written Opinion.
PCT/US2008/055000, dated Sep. 11, 2009, International Preliminary Report on Patentability.
International Search Report and Written Opinion for PCT/US2008/055000 filed Feb. 26, 2008, which Search Report is dated Aug. 1, 2008, and claims as pending for PCT/US2008/055000 as of Feb. 26, 2008.
International Preliminary Report of Patentability for PCT/US2008/055000 filed Feb. 26, 2008, which Report is dated Sep. 11, 2009, and claims as pending for PCT/US2008/055000 as of Feb. 26, 2008.

* cited by examiner

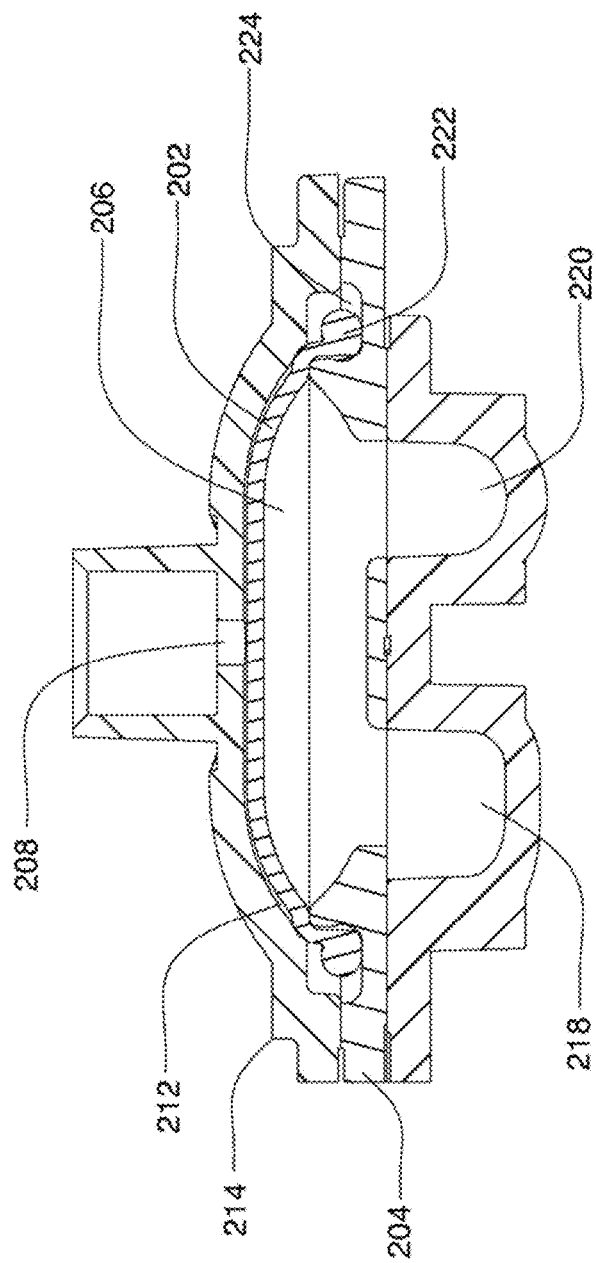

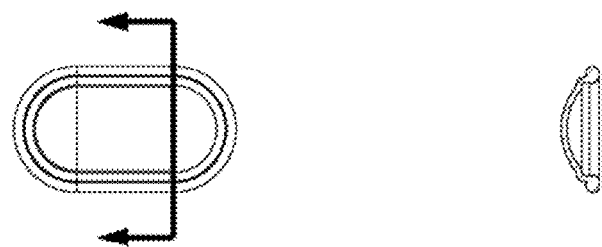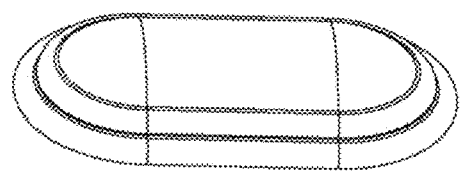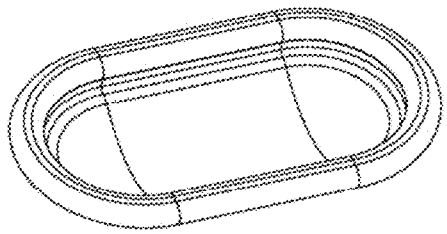
FIG. 2F

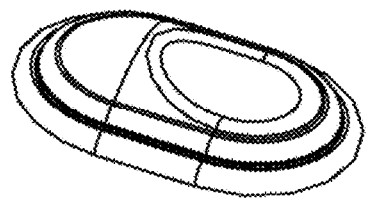
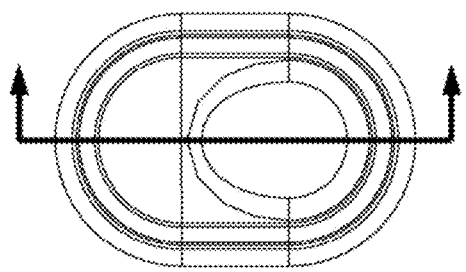
FIG. 2G

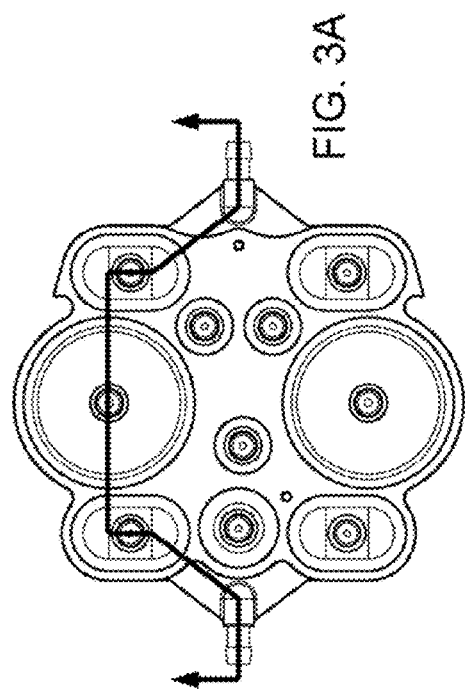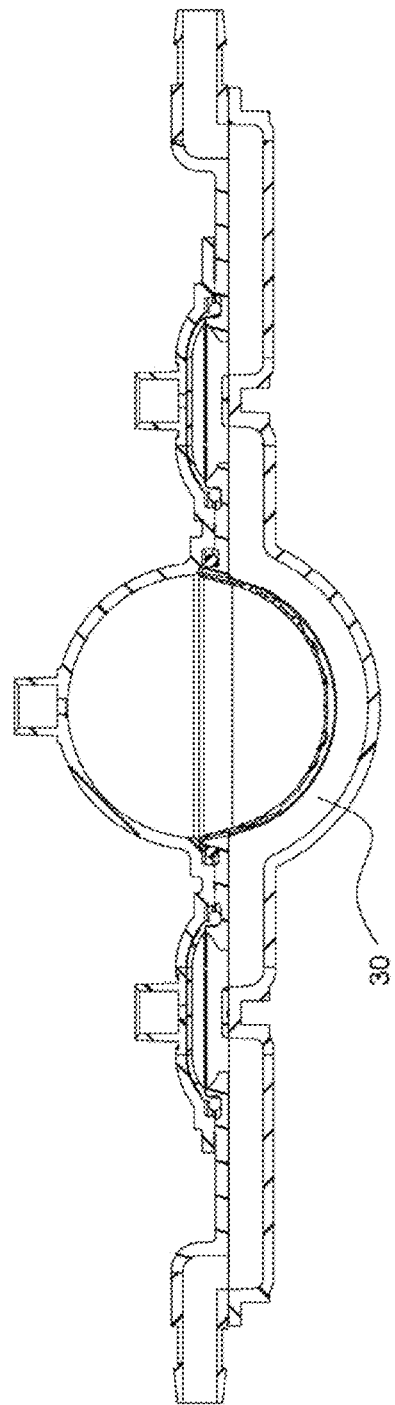

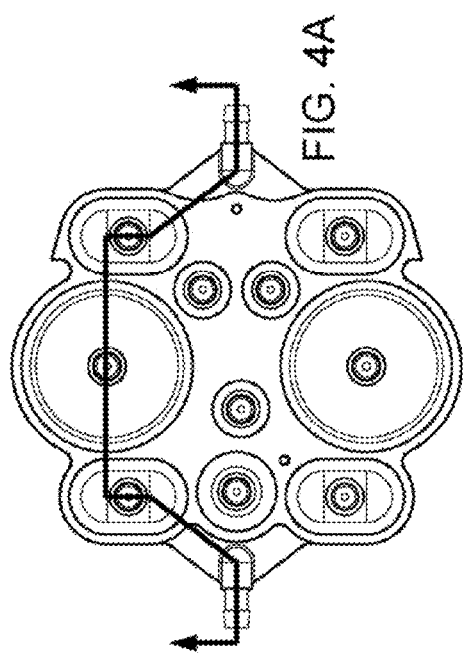
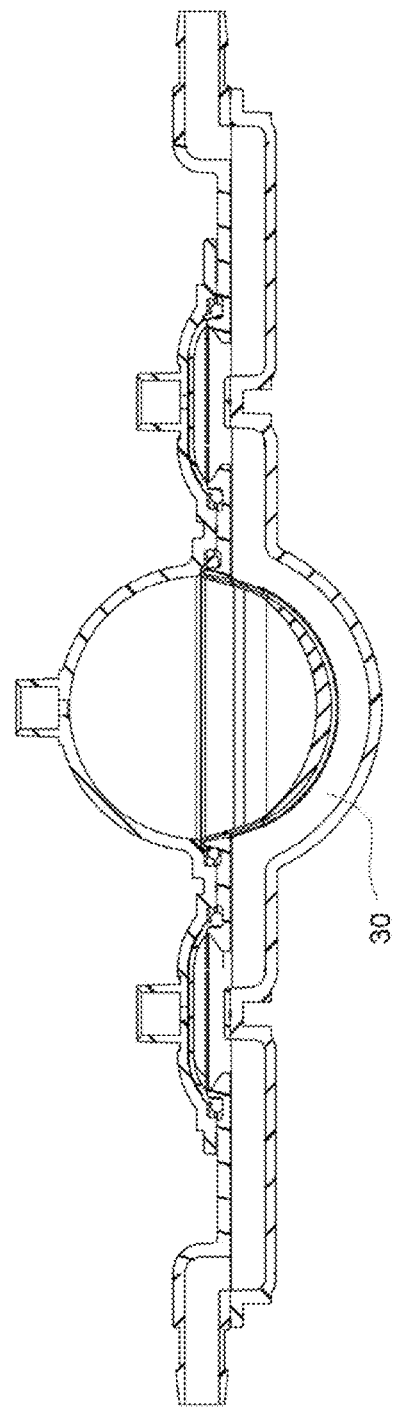
FIG. 4A
FIG. 4B

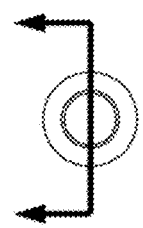
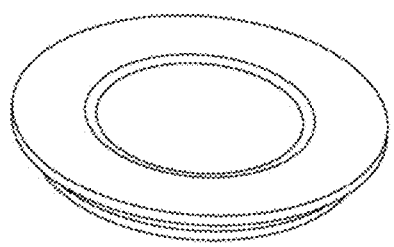
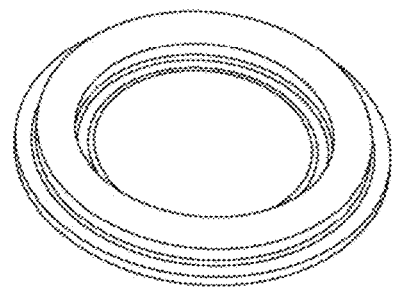
FIG. 5F

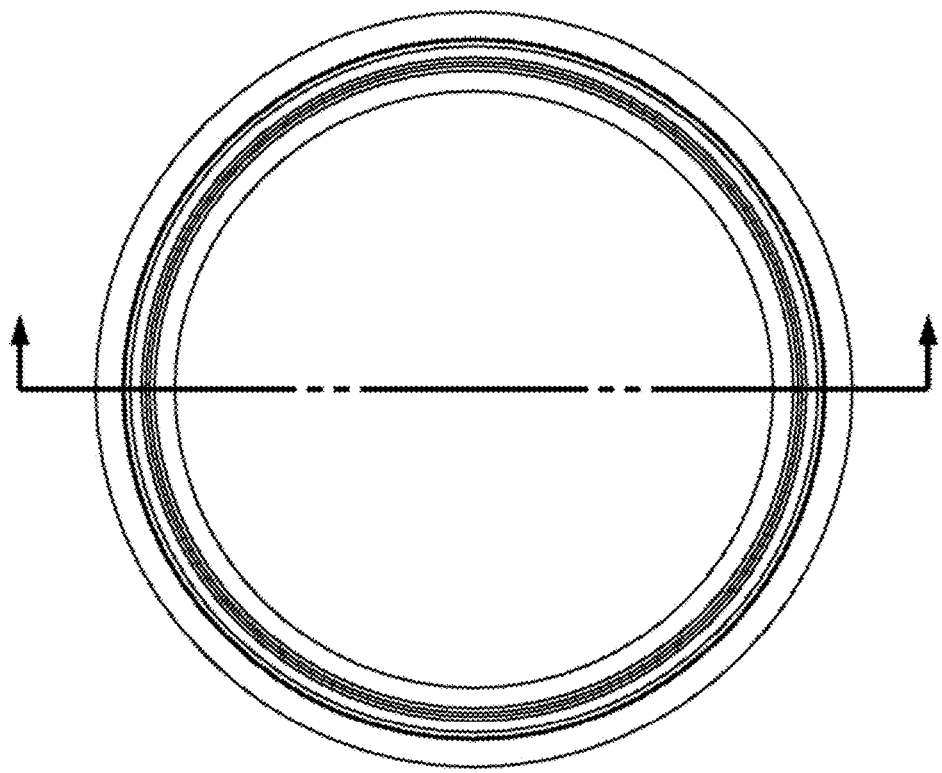
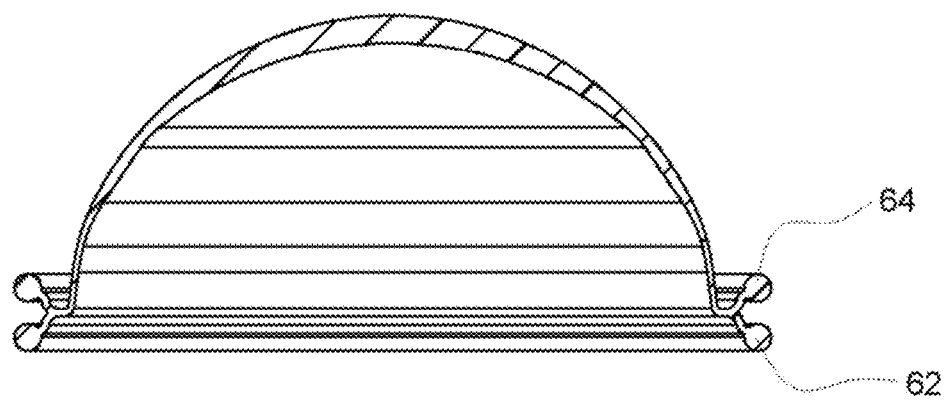
FIG. 6G

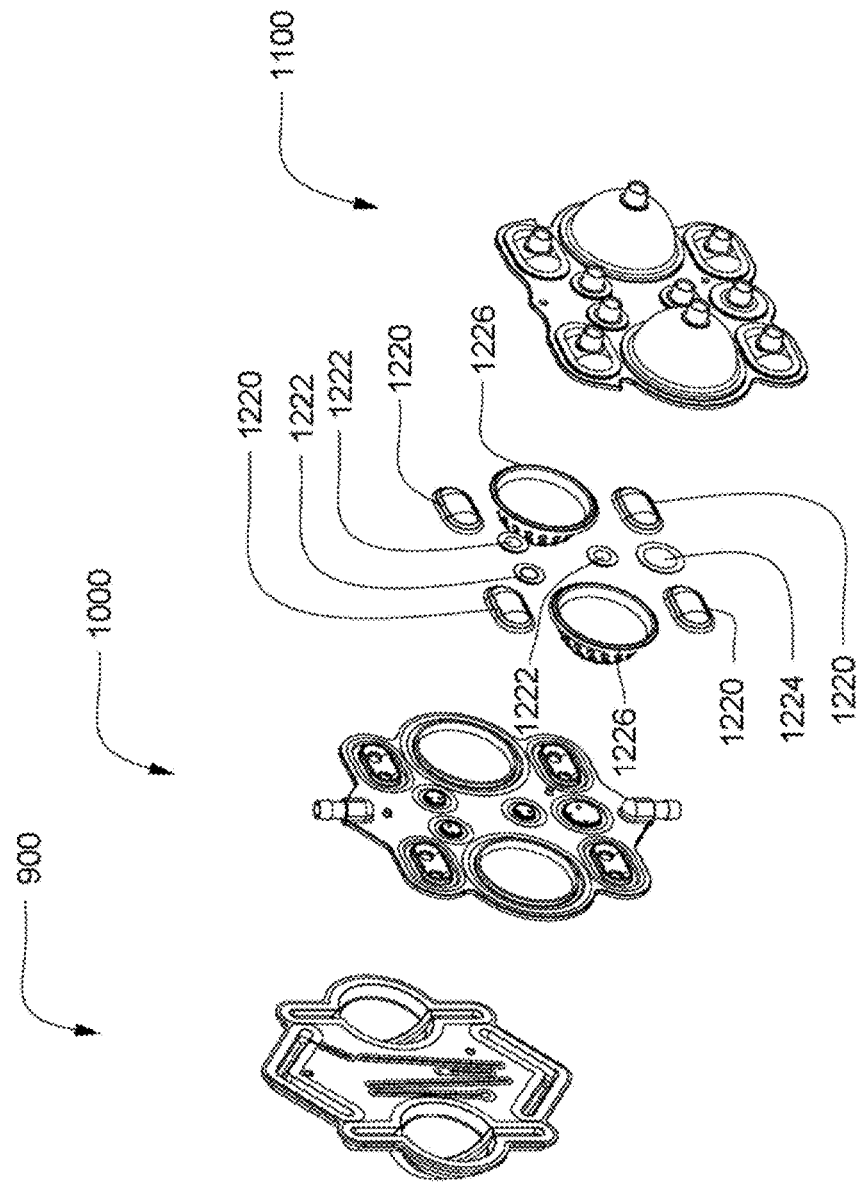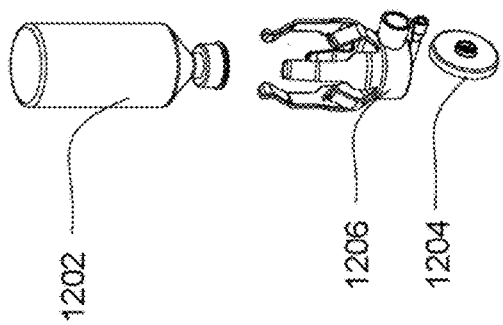
FIG. 12D

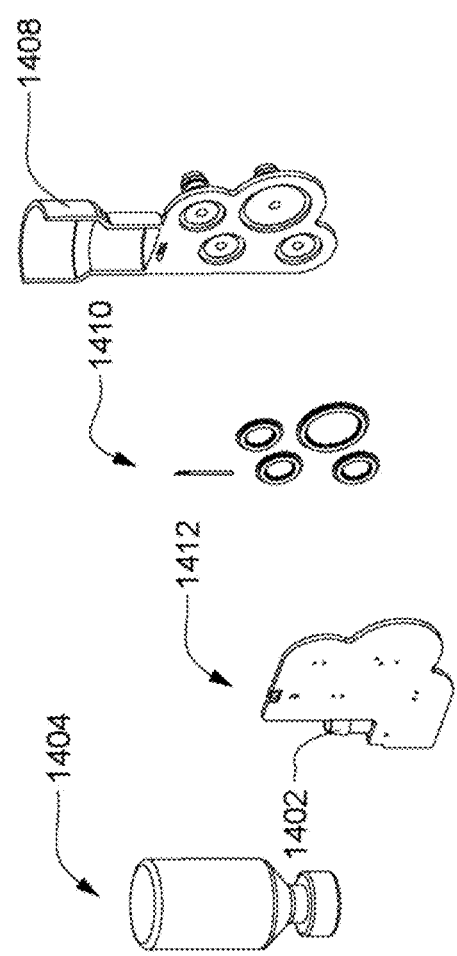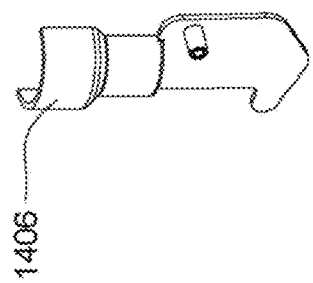
FIG. 14C

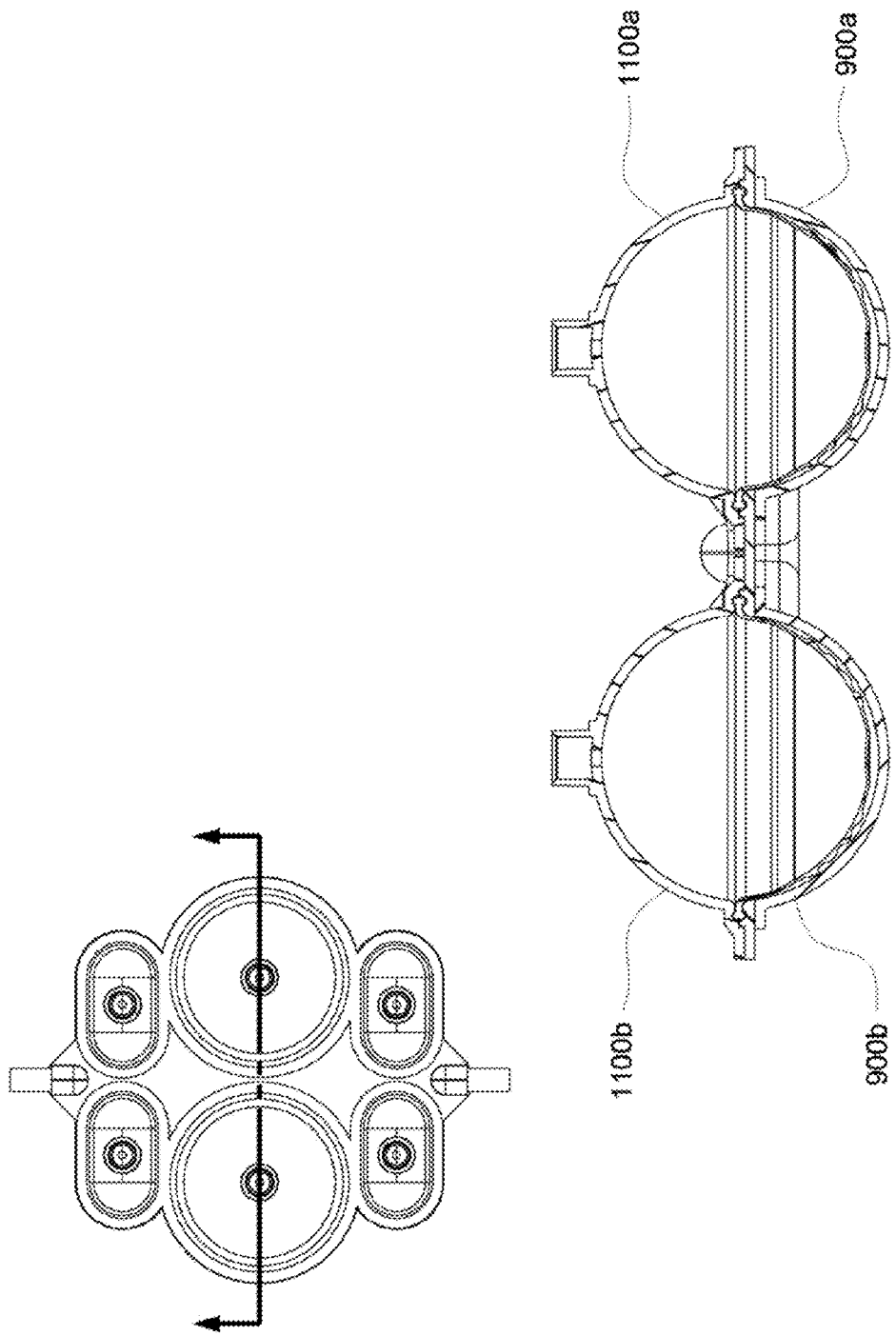

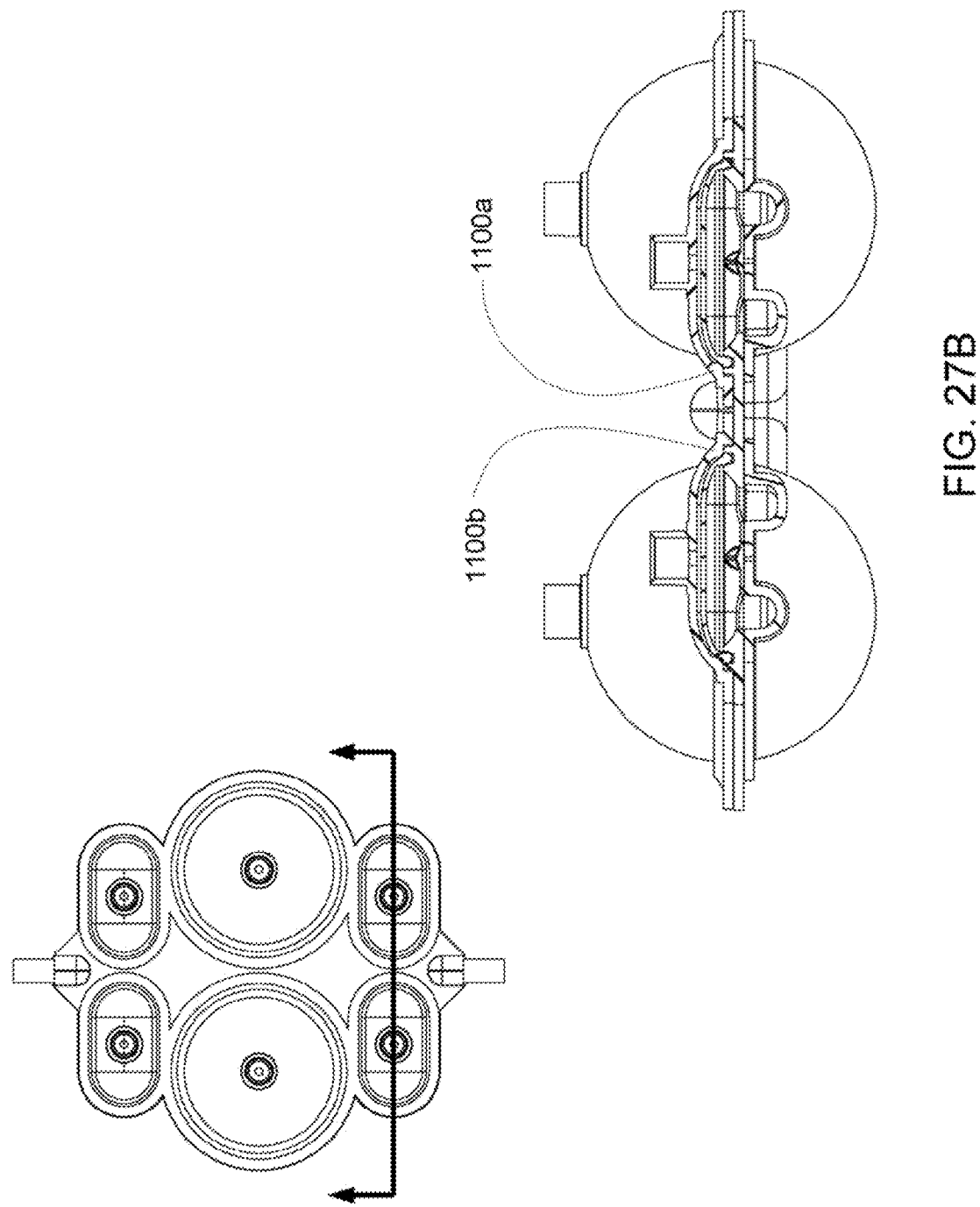

PUMPING CASSETTE

CROSS-REFERENCE TO RELATED APPLICATIONS

This application is a continuation of U.S. patent application Ser. No. 15/056,701, filed on Feb. 29, 2016 and issued as U.S. Pat. No. 9,550,018 on Jan. 24, 2017, which is a continuation of U.S. patent application Ser. No. 13/624,460, filed on Sep. 21, 2012 and issued as U.S. Pat. No. 9,272,082 on Mar. 1, 2016, which is a continuation of U.S. patent application Ser. No. 11/871,680, filed on Oct. 12, 2007 and issued as U.S. Pat. No. 8,273,049 on Sep. 25, 2012, which claims priority from the following U.S. Provisional Patent Applications:

U.S. Provisional Patent Application No. 60/904,024 entitled Hemodialysis System and Methods filed on Feb. 27, 2007; and U.S. Provisional Patent Application No. 60/921,314 entitled Sensor Apparatus filed on Apr. 2, 2007. All of the above-indicated priority applications are hereby incorporated by reference in their entireties.

This application is also a continuation-in-part of U.S. patent application Ser. No. 14/525,071, filed on Oct. 27, 2014, currently pending, which is a continuation of U.S. patent application Ser. No. 13/657,628, filed on Oct. 22, 2012 and issued as U.S. Pat. No. 8,870,549 on Oct. 28, 2014, which is a continuation of U.S. patent application Ser. No. 11/787,212 filed on Apr. 13, 2007 and issued as U.S. Pat. No. 8,292,594 on Oct. 23, 2012, which claims priority from the following U.S. Provisional Patent Applications:

U.S. Provisional Patent Application No. 60/921,314 entitled Sensor Apparatus filed on Apr. 2, 2007.

U.S. Provisional Patent Application No. 60/904,024 entitled Hemodialysis System and Methods filed on Feb. 27, 2007;

U.S. Provisional Patent Application No. 60/835,490 entitled Extracorporeal thermal therapy systems and methods filed on Aug. 4, 2006; and U.S. Provisional Patent Application No. 60/792,073 entitled Extracorporeal thermal therapy systems and methods filed on Apr. 14, 2006. All of the above-indicated priority applications are hereby incorporated by reference in their entireties.

TECHNICAL FIELD

The present invention relates to a pumping cassette for pumping fluid.

SUMMARY OF THE INVENTION

In accordance with one aspect of the pump cassette the cassette includes a housing having at least one fluid inlet line and at least one fluid outlet line. The cassette also includes at least one reciprocating pressure displacement membrane pump within the housing. The pressure pump pumps a fluid from the fluid inlet line to the fluid outlet line. A hollow spike is also included on the housing as well as at least one metering pump The metering pump is fluidly connected to the hollow spike on the housing and to a metering pump fluid line. The metering pump fluid line is fluidly connected to the fluid outlet line.

Various embodiments of this aspect of the cassette include one or more of the following. Where the reciprocating pressure displacement pump includes a curved rigid chamber wall and a flexible membrane attached to the rigid chamber wall. The flexible membrane and the rigid chamber wall define a pumping chamber. Also, where the cassette includes an air vent fluidly connected to the metering pump fluid line. Where the cassette includes an air filter connected to the air vent. Where the cassette housing includes a top plate, a midplate and a bottom plate. Some embodiments further include one or more of the following. A container attachment that includes a container support device for receiving and maintaining a container and a cassette attachment device for attaching to the spike on the cassette. The cassette attachment device includes a housing and needle inside the housing, the needle is in fluid communication with the container support device. Also, where the cassette further includes at least one valve. In some embodiments, the valves include a valve housing having a membrane dividing the housing into two chambers, an actuation chamber and a liquid chamber. In some embodiments, the actuation chamber has at least one aperture and the liquid chamber has at least one aperture. In some embodiments of the valve, the actuation chamber includes two apertures. In some embodiments of the valve, the liquid chamber includes a substantially smooth surface. In some embodiments of the valve, the actuation chamber includes at least one raised feature. In some embodiments of the valve, the valve is a volcano valve.

In accordance with another aspect of the pump cassette the cassette includes a housing having at least one fluid inlet line and at least one fluid outlet line. The cassette also includes at least one reciprocating pressure displacement membrane pump within the housing. The pressure pump pumps a fluid from the fluid inlet line to the fluid outlet line. Also, the cassette includes a second fluid administering system within the housing which includes a metering membrane pump, a second fluid inlet line for pumping a volume of a second fluid into the fluid outlet line, a hollow spike for fluid communication of the second fluid into the second fluid inlet line; and an air vent fluidly connected to the second fluid inlet line.

Various embodiments of this aspect of the cassette include one or more of the following. Where the reciprocating pressure displacement pump includes a curved rigid chamber wall and a flexible membrane attached to the rigid chamber wall. The flexible membrane and the rigid chamber wall define a pumping chamber. Where the cassette housing includes a top plate, a midplate and a bottom plate.

In accordance with another aspect of the pump cassette the cassette includes a housing having at least one blood inlet line for pumping blood from a patient and one blood outlet line for pumping blood to a dialyzer. Also, the cassette includes at least two reciprocating pressure displacement membrane pumps within the housing. The pressure pumps pump the blood from a patient to the dialyzer. The cassette also includes at least two valves, the valves including a housing and a membrane. The membrane divides the housing into two chambers, an actuation chamber and a liquid chamber. The actuation chamber has at least one aperture and the liquid chamber has at least two apertures. The liquid chamber includes a substantially smooth surface. The cassette also includes a heparin administering system within the housing. The heparin administering system includes a membrane pump, a heparin inlet line for pumping a volume of heparin into the blood outlet line, a hollow spike for fluid communication of heparin into the heparin inlet line, and an air filter fluidly connected to the heparin inlet line for trapping air.

Various embodiments of this aspect of the cassette include one or more of the following. Where the reciprocating pressure displacement pump includes a curved rigid chamber wall and a flexible membrane attached to the rigid chamber wall. The flexible membrane and the rigid chamber wall define a pumping chamber. Where the cassette housing includes a top plate, a midplate and a bottom plate. Where the reciprocating pressure displacement membrane pumps includes a membrane dimpled on at least one surface.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein;

FIG. 2C is a sectional view of another embodiment of one type of pneumatically controlled valve that is incorporated into some embodiments of the cassette;

FIGS. 2E-2F are top and bottom views of embodiments of the valving membrane;

FIG. 2G shows pictorial, top and cross sectional views of one embodiment of the valving membrane;

FIGS. 3A and 3B are top and section views respectively of a pod pump within a cassette;

FIGS. 4A and 4B are pictorial views respectively of a pod pump within a cassette having a variable membrane;

FIGS. 5E-5H are pictorial views of various embodiments of the metering pump membrane;

FIG. 6G is a cross sectional view of a double ring membrane with a variable surface;

FIG. 12D is an exploded view of the assembled exemplary embodiment of the cassette with a vial;

FIGS. 14C-14D show an exploded view of the assembled alternate embodiment of the metering pump;

FIGS. 27A-27B show cross sectional views of an alternate embodiment of the assembled cassette.

DETAILED DESCRIPTION OF SPECIFIC EMBODIMENTS

1. Pumping Cassette 1.1 Cassette

Figure 1A:
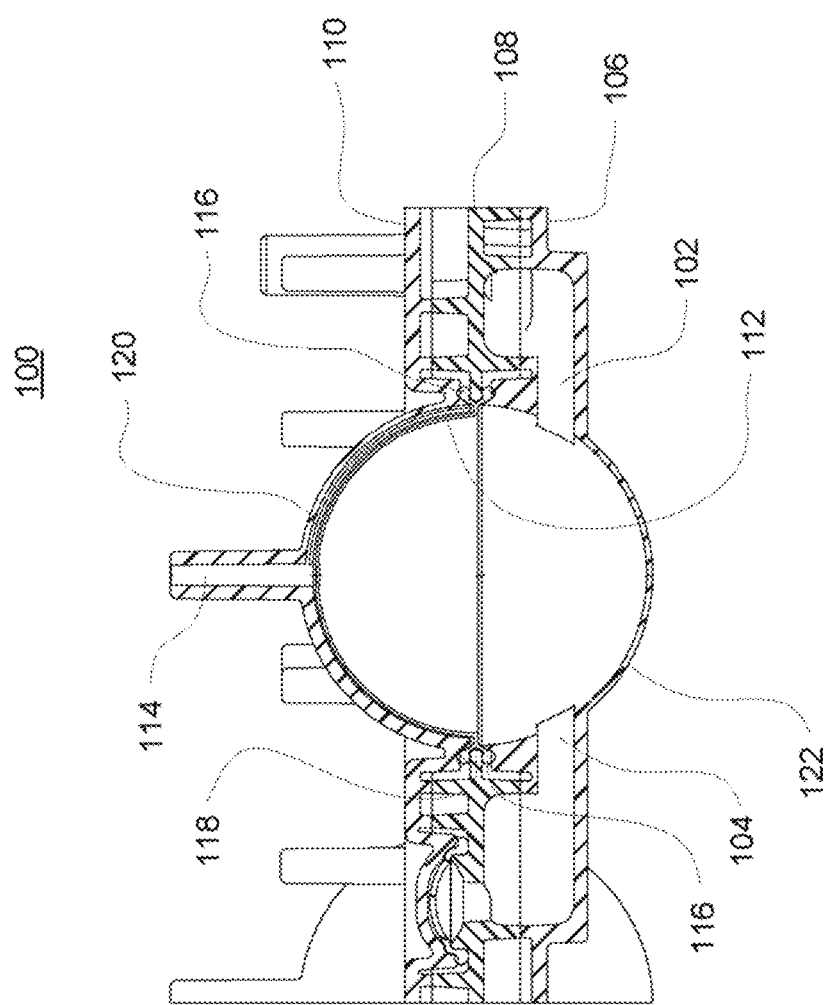
FIG. 1A is a sectional view of one exemplary embodiment of a pod pump that is incorporated into embodiments of the cassette.

The pumping cassette include various features, namely, pod pumps, fluid lines and in some embodiment, valves. The cassette embodiments shown and described in this description include exemplary and some alternate embodiments. However, any variety of cassettes is contemplated that include a similar functionality. As well, although the cassette embodiments described herein are implementations of the fluid schematics as shown in FIGS. 8A and 8B, in other embodiments, the cassette may have varying fluid paths and/or valve placement and/or pod pump placements and numbers and thus, is still within the scope of the invention.

In the exemplary embodiment, the cassette includes a top plate, a midplate and a bottom plate. There are a variety of embodiments for each plate. In general, the top plate includes pump chambers and fluid lines, the midplate includes complementary fluid lines, metering pumps and valves and the bottom plate includes actuation chambers (and in some embodiments, the top plate and the bottom plate include complementary portions of a balancing chamber).

In general, the membranes are located between the midplate and the bottom plate, however, with respect to balancing chambers, a portion of a membrane is located between the midplate and the top plate. Some embodiments include where the membrane is attached to the cassette, either overmolded, captured, bonded, press fit, welded in or any other process or method for attachment, however, in the exemplary embodiments, the membranes are separate from the top plate, midplate and bottom plate until the plates are assembled.

The cassettes may be constructed of a variety of materials. Generally, in the various embodiment, the materials used are solid and non flexible. In the preferred embodiment, the plates are constructed of polysulfone, but in other embodiments, the cassettes are constructed of any other solid material and in exemplary embodiment, of any thermoplastic or thermosot.

In the exemplary embodiment, the cassettes are formed by placing the membranes in their correct locations, assembling the plates in order and connecting the plates in one embodiment, the plates are connected using a laser welding technique. However, in other embodiments, the plates may be glued, mechanically fastened, strapped together, ultrasonically welded or any other mode of attaching the plates together.

In practice, the cassette may be used to pump any type of fluid from any source to any location. The types of fluid include nutritive, nonnutritive, inorganic chemicals, organic chemicals, bodily fluids or any other type of fluid. Additionally, fluid in some embodiments include a gas, thus, in some embodiments, the cassette is used to pump a gas.

The cassette serves to pump and direct the fluid from and to the desired locations. In some embodiments, outside pumps pump the fluid into the cassette and the cassette pumps the fluid out. However, in some embodiments, the pod pumps serve to pull the fluid into the cassette and pump the fluid out of the cassette.

As discussed above, depending on the valve locations, control of the fluid paths is imparted. Thus, the valves being in different locations or additional valves are alternate embodiments of this cassette. Additionally, the fluid lines and paths shown in the figures described above are mere examples of fluid lines and paths. Other embodiments may have more, less and/or different fluid paths. In still other embodiments, valves are not present in the cassette.

The number of pod pumps described above may also vary depending on the embodiment. For example, although the exemplary and alternate embodiments shown and described above include two pod pumps, in other embodiments, the cassette includes one. In still other embodiments, the cassette includes more than two pod pumps. The pod pumps can be single pumps or work in tandem to provide a more continuous flow Either or both may be used in various embodiments of the cassette.

The various fluid inlets and fluid outlets are fluid ports. In practice, depending on the valve arrangement and control, a fluid inlet can be a fluid outlet. Thus, the designation of the fluid port as a fluid inlet or a fluid outlet is only for description purposes. The various embodiments have interchangeable fluid ports. The fluid ports are provided to impart particular fluid paths onto the cassette. These fluid ports are not necessarily all used all of the time; instead, the variety of fluid ports provides flexibility of use of the cassette in practice.

1.2 Exemplary Pressure Pod Pump Embodiments

FIG. 1A is a sectional view of an exemplary pod pump 100 that is incorporated into a fluid control or pump cassette (see also FIGS. 3 and 4), in accordance with an exemplary embodiment of the cassette. In this embodiment, the pod pump is formed from three rigid pieces, namely a "top" plate 106, a midplate 108, and a "bottom" plate 110 (it should be noted that the terms "top" and "bottom" are relative and are used here for convenience with reference to the orientation shown in FIG. 1A). The top and bottom plates 106 and 110 include generally hemispheroid portions that when assembled together define a hemispheroid chamber, which is a pod pump 100.

A membrane 112 separates the central cavity of the pod pump into two chambers. In one embodiment, these chambers are: the pumping chamber that receives the fluid to be pumped and an actuation chamber for receiving the control gas that pneumatically actuates the pump. An inlet 102 allows fluid to enter the pumping chamber, and an outlet 104 allows fluid to exit the pumping chamber. The inlet 102 and the outlet 104 may be formed between midplate 108 and the top plate 106. Pneumatic pressure is provided through a pneumatic port 114 to either force, with positive gas pressure, the membrane 112 against one wall of pod pump cavity to minimize the pumping chamber's volume, or to draw, with negative gas pressure, the membrane 112 towards the other wall of the pod pump 100 cavity to maximize the pumping chamber's volume.

The membrane 112 is provided with a thickened rim 116, which is held tightly by a protrusion 118 in the midplate 108. Thus, in manufacture, the membrane 112 can be placed in and held by the groove 108 before the bottom plate 110 is connected (in the exemplary embodiment) to the midplate 108.

Figure 1B:
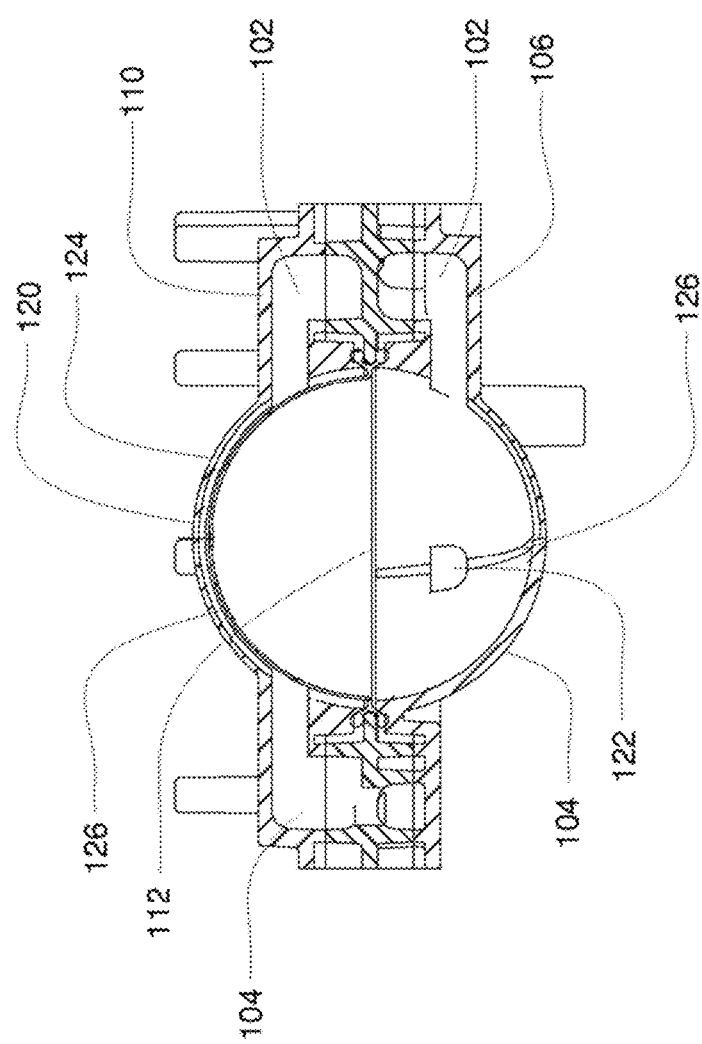
FIG. 1B is a sectional view of an alternate embodiment of pod pump that is incorporated into embodiments of the cassette.

Although not shown in FIGS. 1A and 1B, in some embodiments of the pod pump, on the fluid side, a groove is present on the chamber wall. The groove acts to prevent folds In the membrane from trapping fluid in the chamber when emptying.

Referring first to FIG. 1A a cross sectional view of a reciprocating positive-displacement pump 100 in a cassette is shown. The pod pump 100 includes a flexible membrane 112 (also referred to as the "pump diaphragm" or "membrane") mounted where the pumping chamber (also referred to as a "liquid chamber" or "liquid pumping chamber") wall 122 and the actuation chamber (also referred to as the "pneumatic chamber") wall 120 meet. The membrane 112 effectively divides that interior cavity into a variable-volume pumping chamber (defined by the rigid interior surface of the pumping chamber wall 122 and a surface of the membrane 112) and a complementary variable-volume actuation chamber (defined by the rigid interior surface of the actuation chamber wall 120 and a surface of the membrane 112). The top portion 106 includes a fluid inlet 102 and a fluid outlet 104, both of which are in fluid communication with the pumping/liquid chamber. The bottom portion 110 includes an actuation or pneumatic interface 114 in fluid communication with the actuation chamber. As discussed in greater detail below, the membrane 112 can be urged to move back and forth within the cavity by alternately applying negative or vent to atmosphere and positive pneumatic pressure at the pneumatic interface 114. As the membrane 112 reciprocates back and forth, the sum of the volumes of the pumping and actuation chambers remains constant.

During typical fluid pumping operations, the application of negative or vent to atmosphere pneumatic pressure to the actuation or pneumatic interface 114 tends to withdraw the membrane 112 toward the actuation chamber wall 120 so as to expand the pumping/liquid chamber and draw fluid into the pumping chamber through the inlet 102, while the application of positive pneumatic pressure tends to push the membrane 112 toward the pumping chamber wall 122 so as to collapse the pumping chamber and expel fluid in the pumping chamber through the outlet 104. During such pumping operations, the interior surfaces of the pumping chamber wall 122 and the actuation chamber wall 120 limit movement of the membrane 112 as it reciprocates back and forth. In the embodiment shown in FIG. 1A, the interior surfaces of the pumping chamber wall 122 and the actuation chamber wail 120 are rigid, smooth, and hemispherical. In lieu of a rigid actuation chamber wall 120, an alternative rigid limit structure—for example, a portion of a bezel used for providing pneumatic pressure and/or a set of ribs—may be used to limit the movement of the membrane as the pumping chamber approaches maximum value. Bezels and rib structures are described generally in U.S. patent application Ser. No. 10/697,450 entitled BEZEL ASSEMBLY FOR PNEUMATIC CONTROL filed on Oct. 30, 2003 and published as Publication No. US 2005/0095154 and related PCT Application No. PCT/US2004/035952 entitled BEZEL ASSEMBLY FOR PNEUMATIC CONTROL filed on Oct. 29, 2004 and published as Publication No. WO 2005/044435, both of which are hereby incorporated herein by reference in their entireties. Thus, the rigid limit structure—such as the rigid actuation chamber wall 120, a bezel, or a set of ribs—defines the shape of the membrane 112 when the pumping chamber is at its maximum value. In a preferred embodiment, the membrane 112 (when urged against the rigid limit structure) and the rigid interior surface of the pumping chamber wall 122 define a spherical pumping chamber volume when the pumping chamber volume is at a minimum.

Thus, in the embodiment shown in FIG. 1A, movement of the membrane 112 is limited by the pumping chamber wall 122 and the actuation chamber wall 120. As long as the positive and vent to atmosphere or negative pressurizations provided through the pneumatic port 114 are strong enough, the membrane 112 will move from a position limited by the actuation chamber wall 120 to a position limited by the pumping chamber wall 122. When the membrane 112 is forced against the actuation chamber wall 120, the membrane and the pumping chamber wall 122 define the maximum volume of the pumping chamber. When the membrane is forced against the pumping chamber wall 122, the pumping chamber is at its minimum volume.

In an exemplary embodiment, the pumping chamber wall 122 and the actuation chamber wall 120 both have a hemispheroid shape so that the pumping chamber will have a spheroid shape when it is at its maximum, volume. By using a pumping chamber that attains a spheroid shape—and particularly a spherical shape—at maximum volume, circulating flow may be attained throughout the pumping chamber. Such shapes accordingly tend to avoid stagnant pockets of fluid in the pumping chamber. As discussed further below, the orientations of the inlet 102 and outlet 104 also tend to have an impact on the flow of fluid through the pumping chamber and in some embodiments, reduce the likelihood of stagnant pockets of fluid forming. Additionally, compared to other volumetric shapes, the spherical shape (and spheroid shapes in general) tends to create less shear and turbulence as the fluid circulates into, through, and out of the pumping chamber.

Figure 18A:
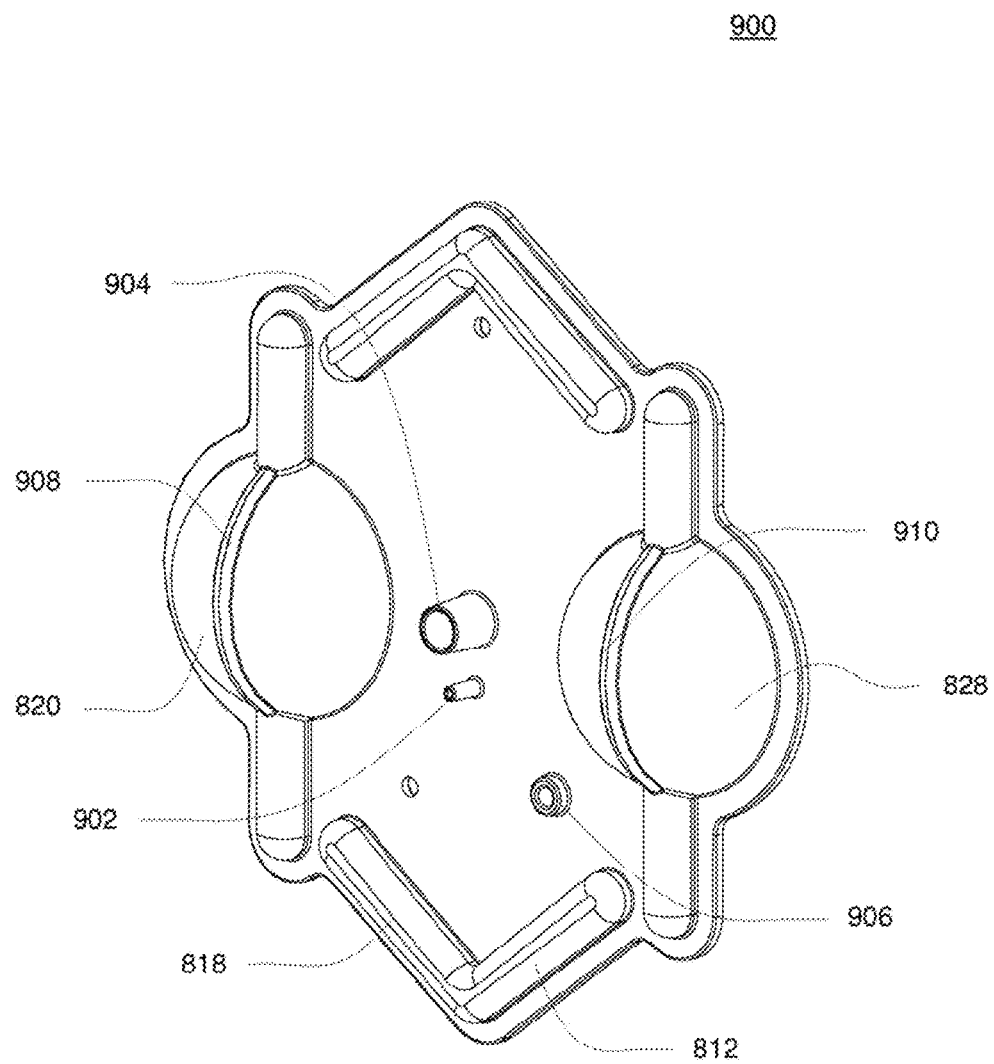
FIGS. 18A-18B show isometric and top views of outer top plate according to an alternate embodiment of the cassette.
Figure 18B:
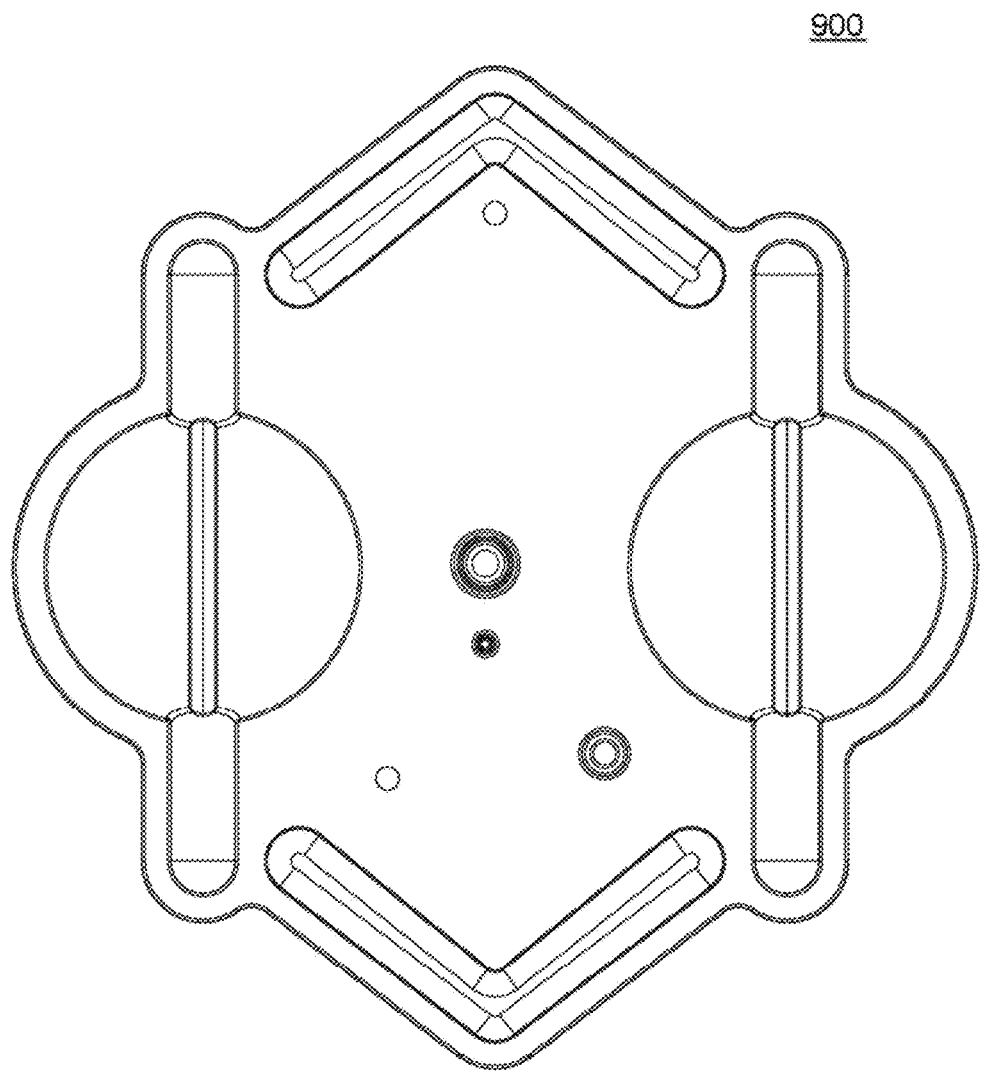
Figure 18C:
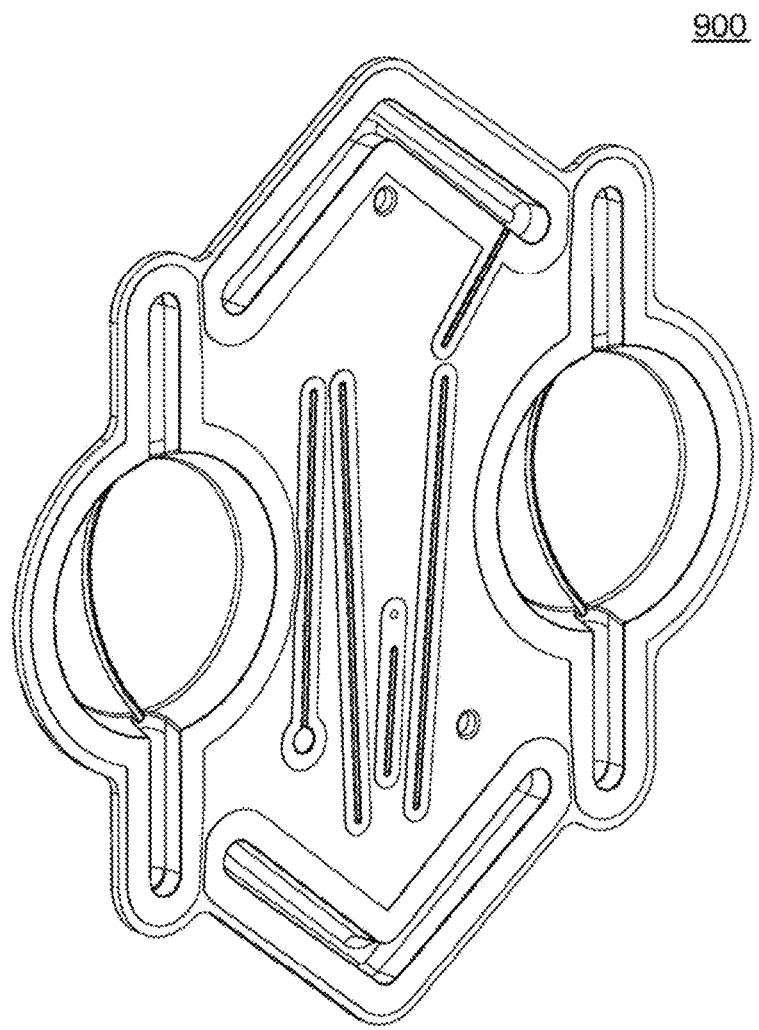
FIGS. 18C-18D show bottom views of the inner top plate according to an alternate embodiment of the cassette.
Figure 18D:
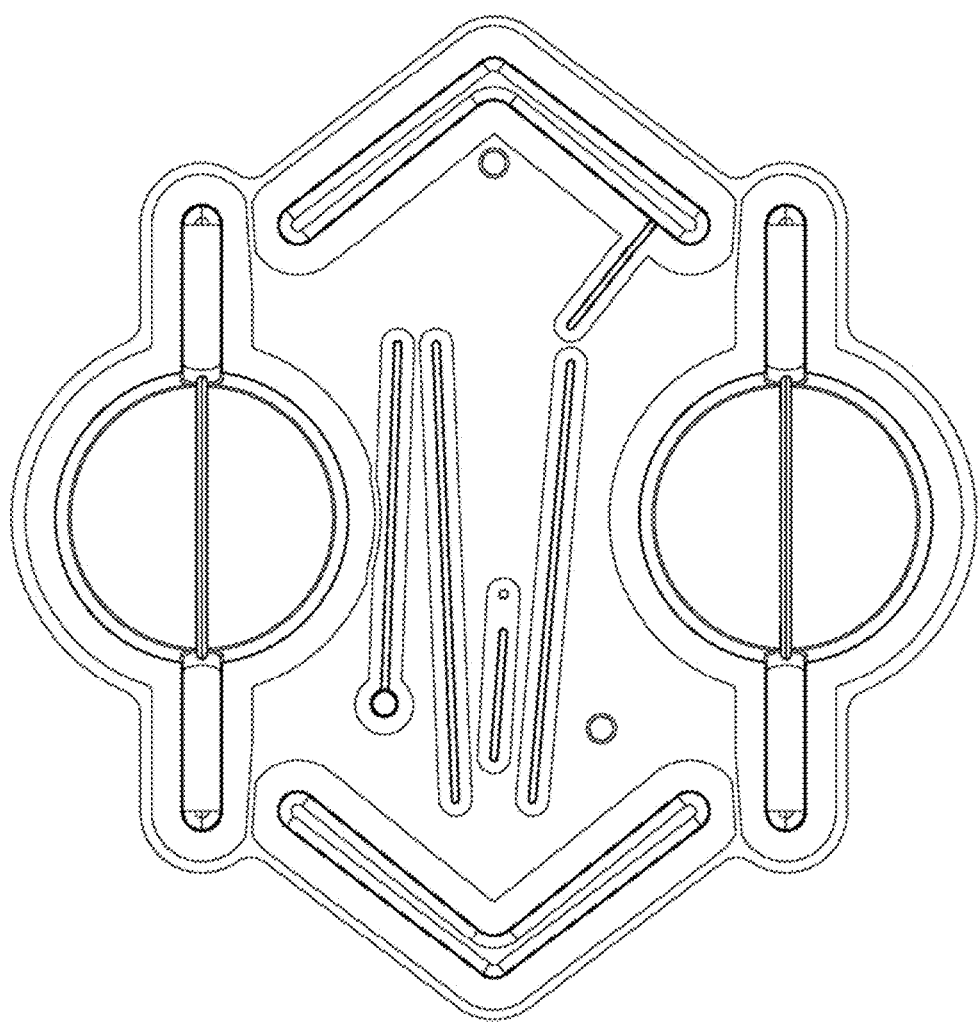
Figure 18E:
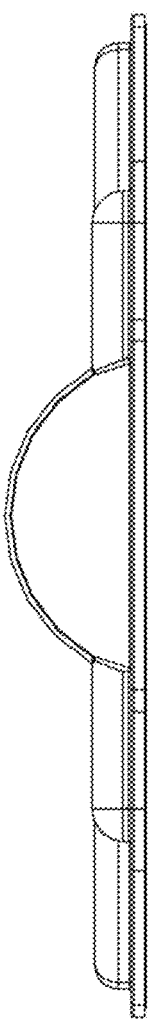
FIG. 18E shows a side view of the alternate embodiment of the top plate.
Figure 19A:
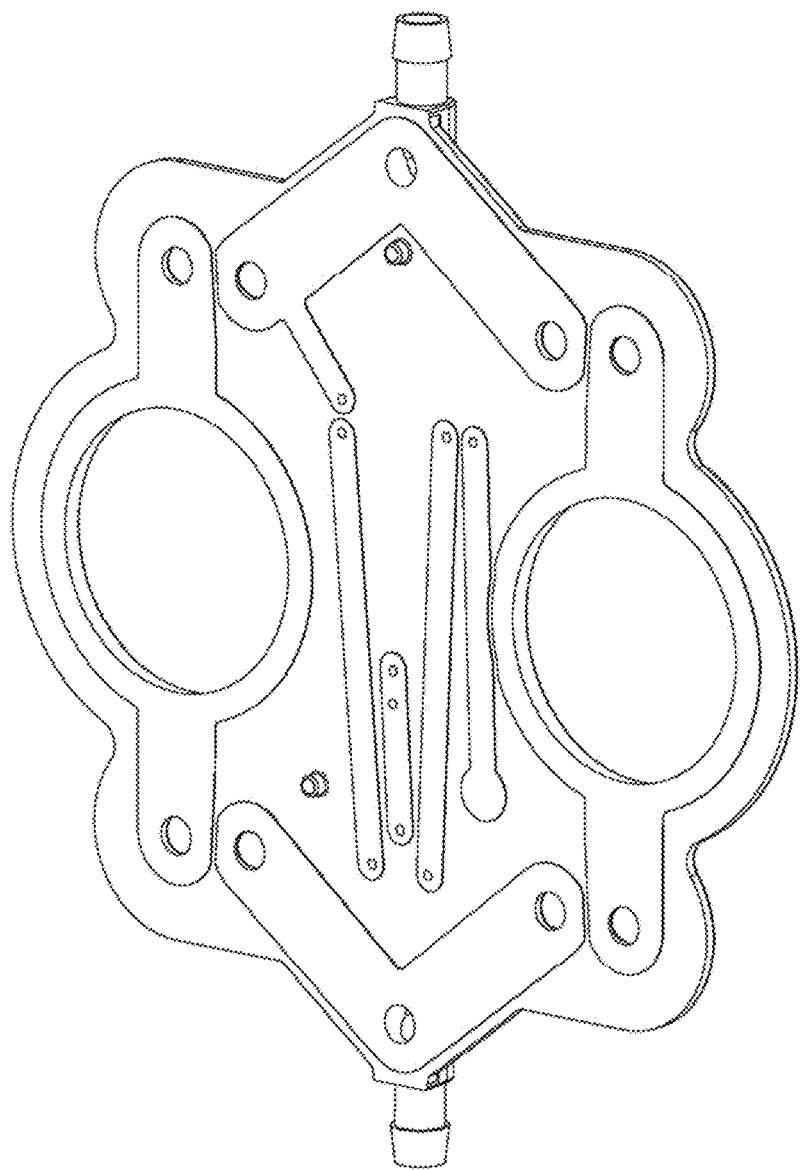
FIGS. 19A-19B show isometric and top views of the liquid side midplate according to an alternate embodiment of the cassette.
Figure 19B:
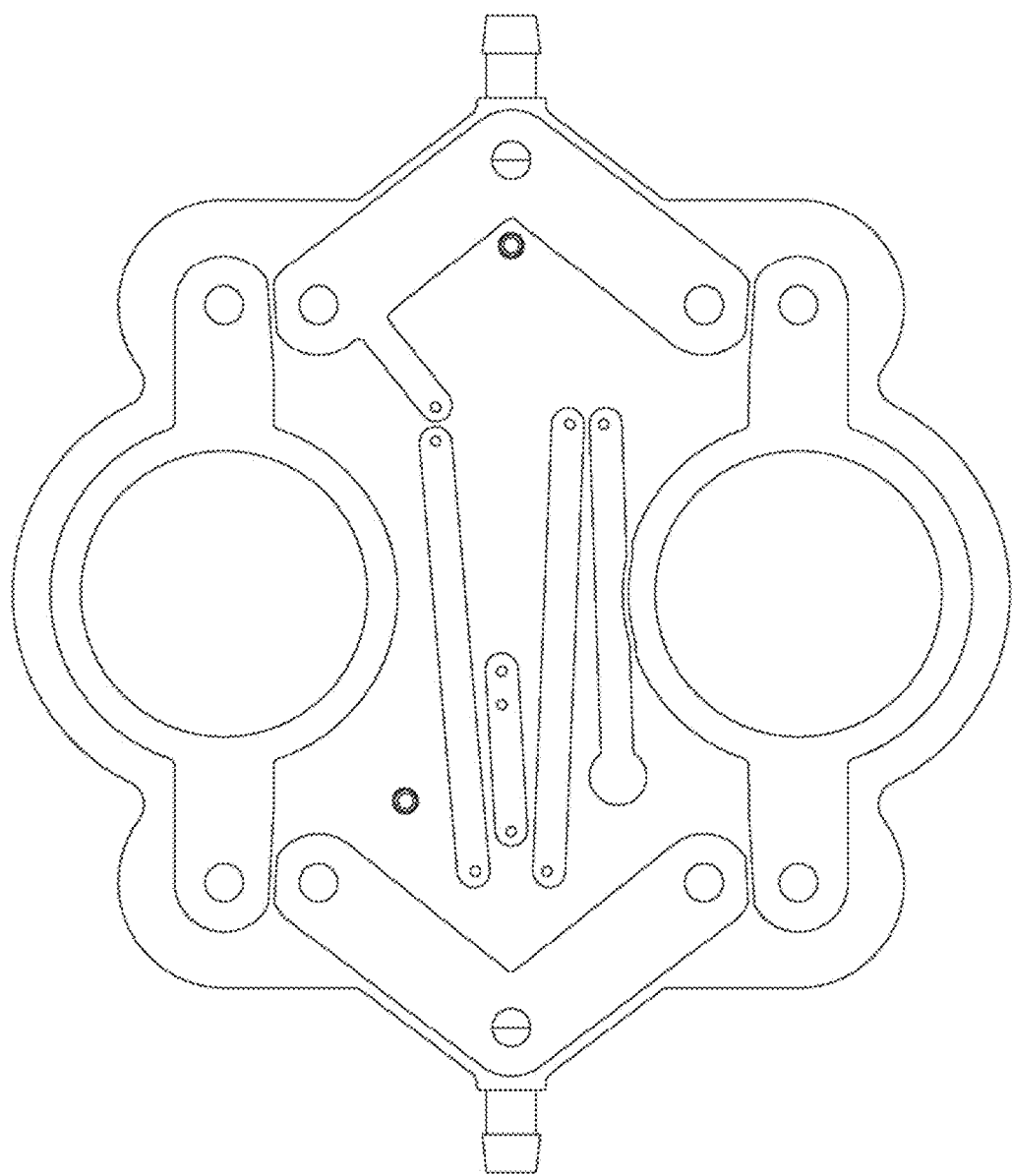
Figure 19C:
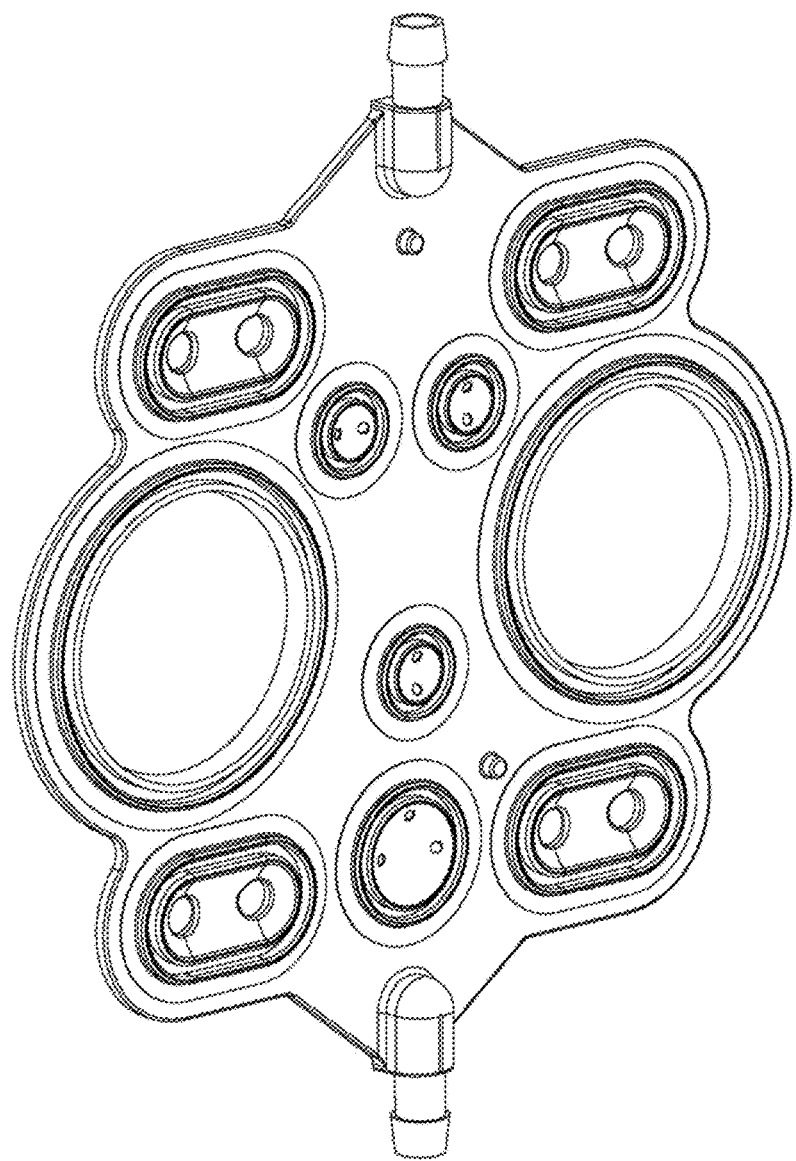
FIGS. 19C-19D show isometric and bottom views of the air side midplate according to an alternate embodiment of the cassette.
Figure 19D:
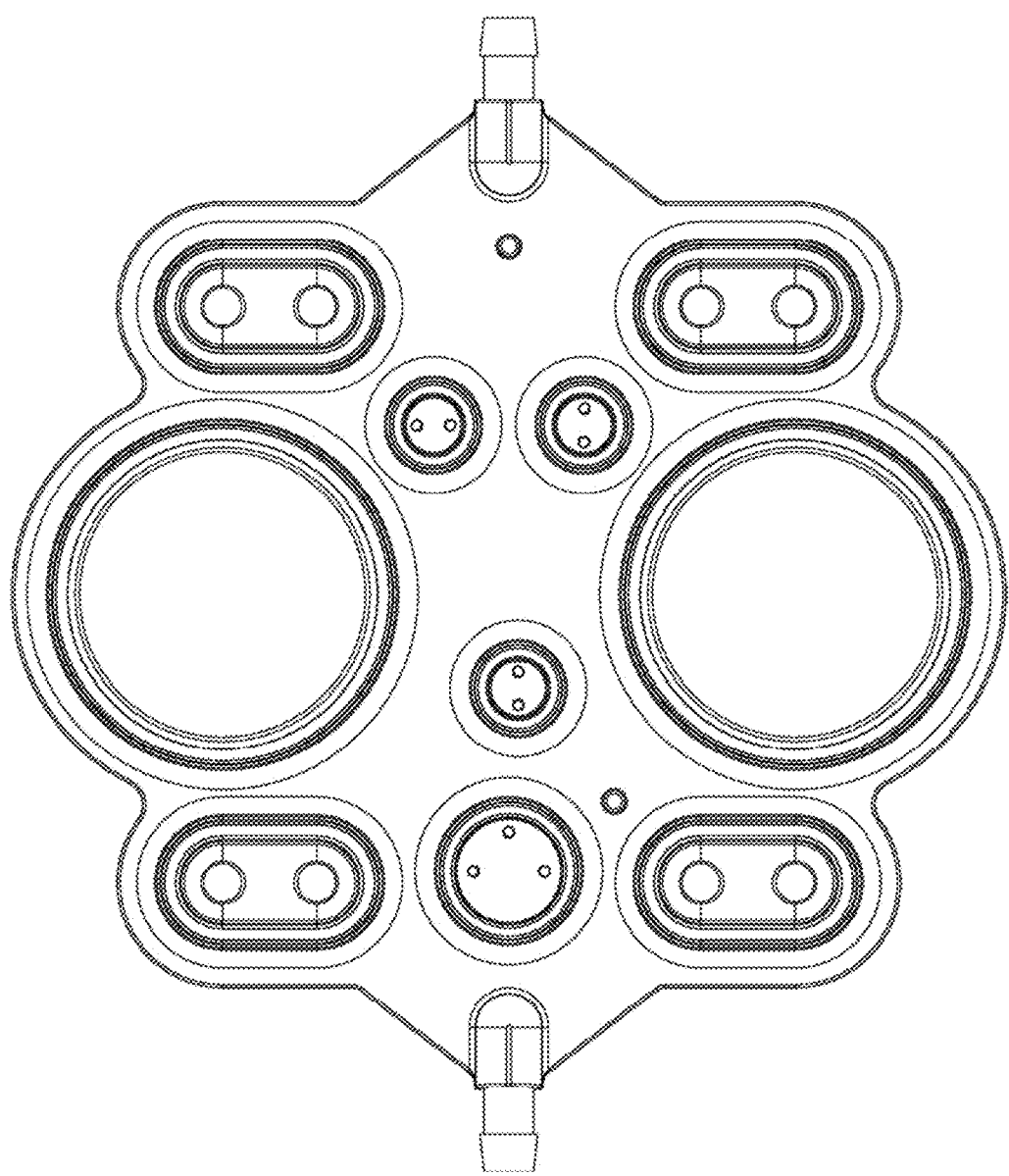
Figure 19E:
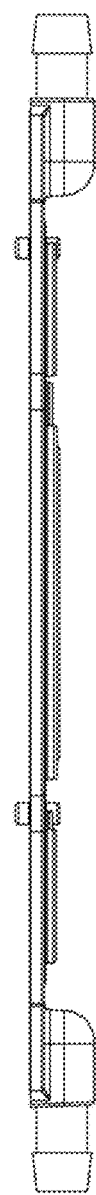
FIG. 19E shows a side view of the alternate embodiment of the midplate.
Figure 20A:
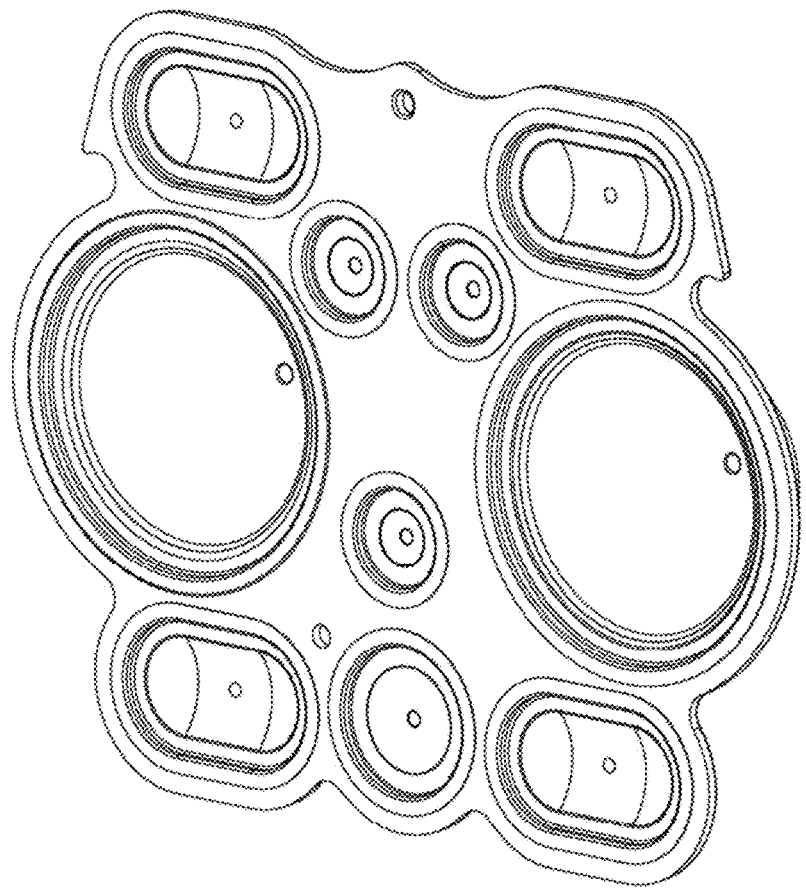
FIGS. 20A-20B show isometric and top views of the inner bottom plate according to an alternate embodiment of the cassette.
Figure 20B:
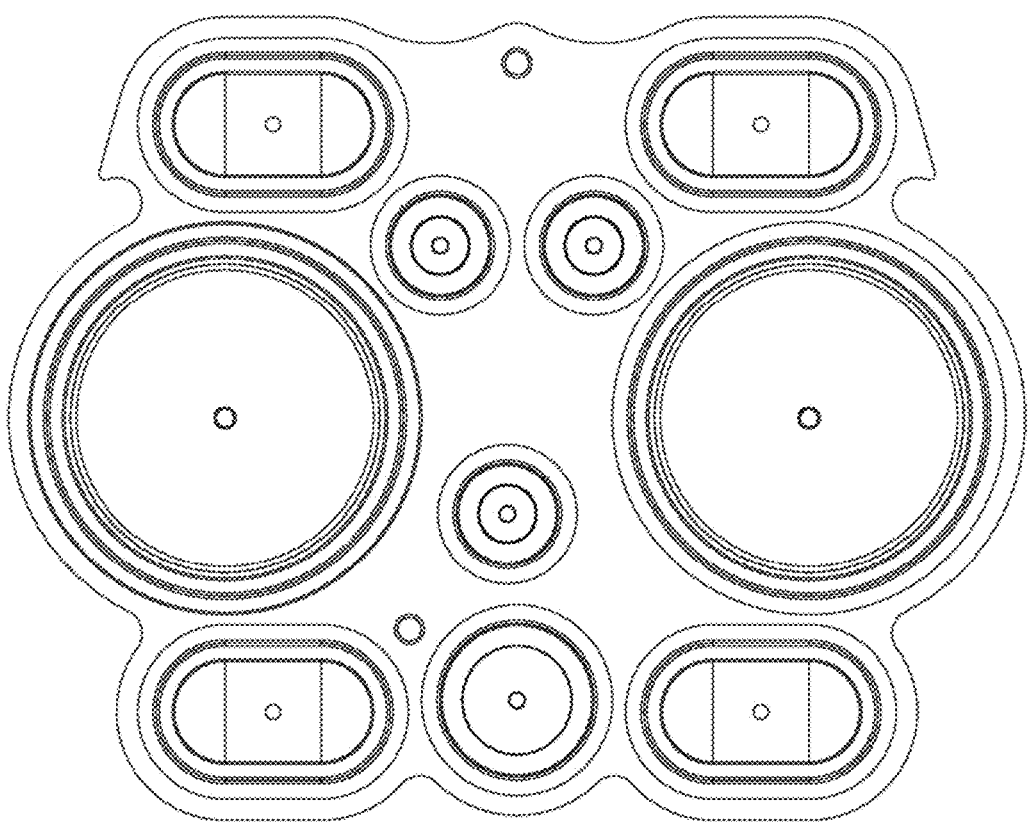
Figure 20C:
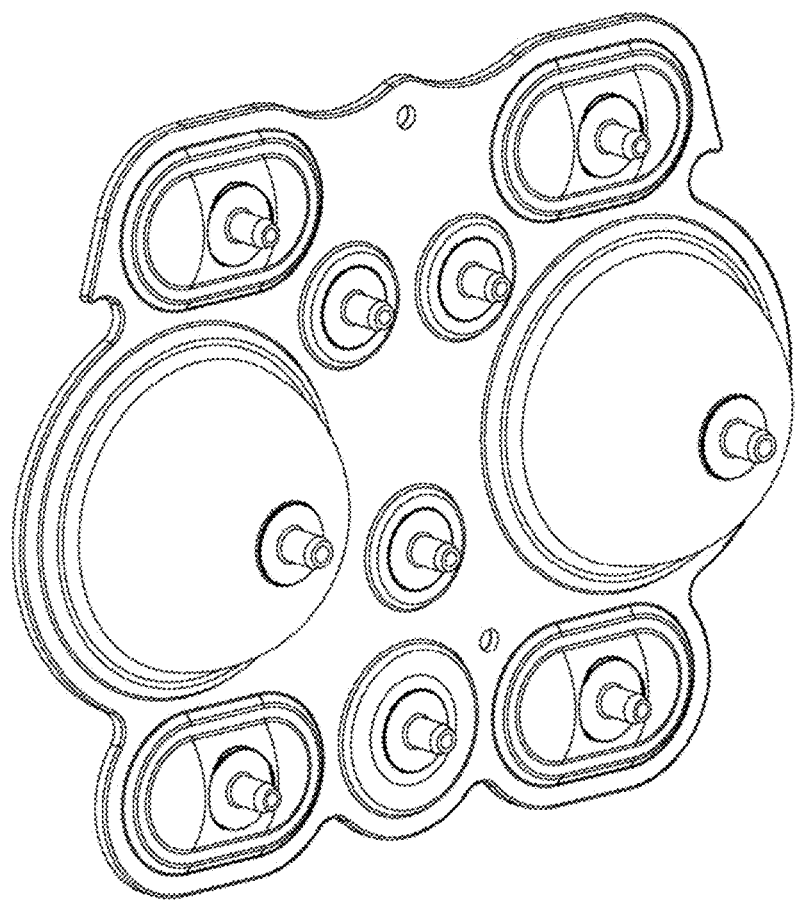
FIGS. 20C-20D show isometric and bottom views of the outer bottom according to an alternate embodiment of the cassette.
Figure 20D:
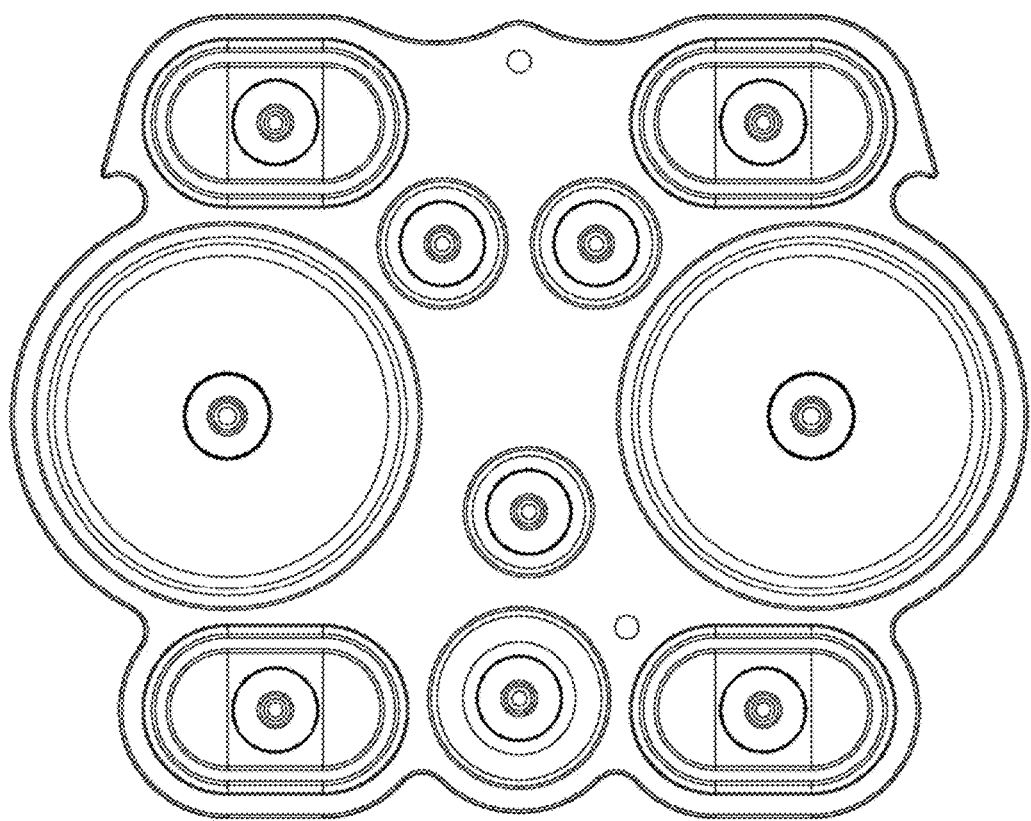
Figure 20E:
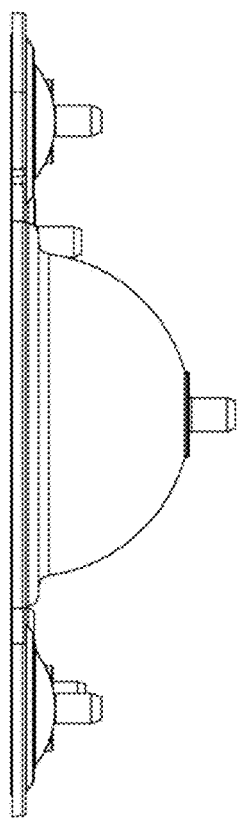
FIG. 20E shows a side view of the alternate embodiment of the bottom plate.
Figure 21A:
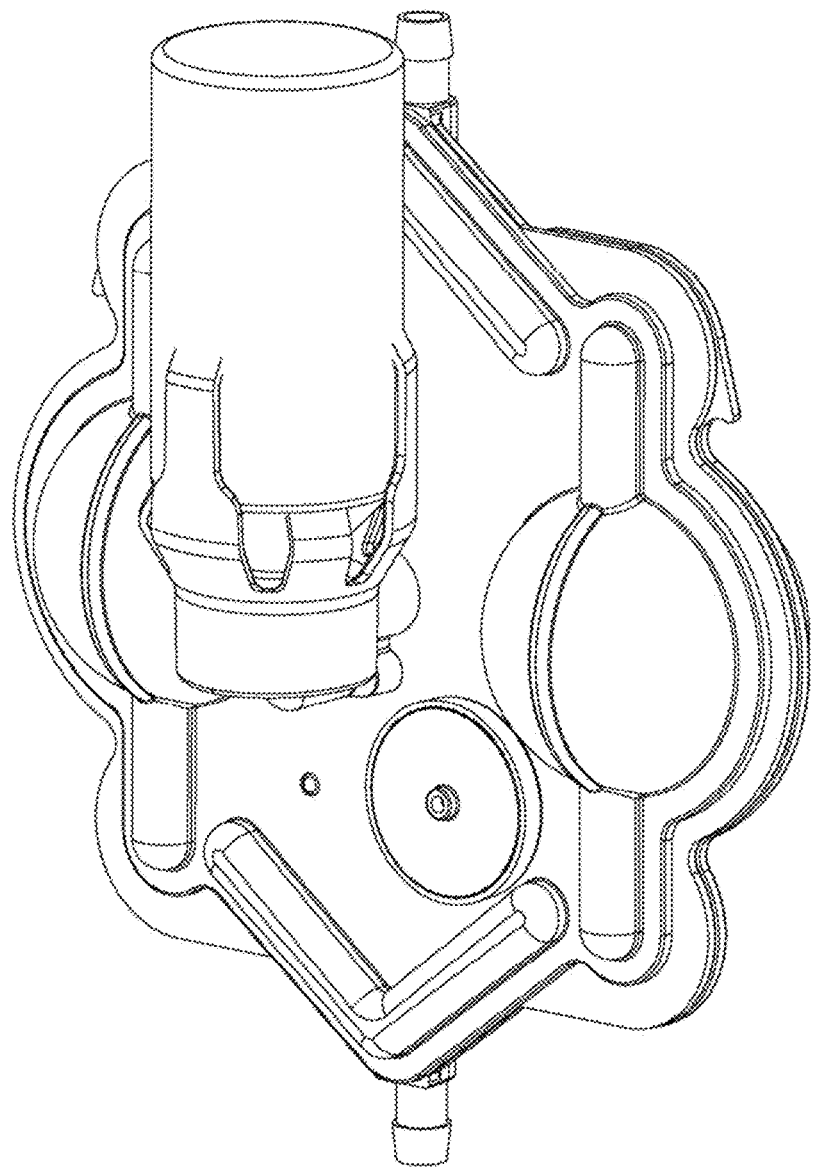
FIG. 21A is a top view of an assembled alternate embodiment of the cassette with a vial.
Figure 21B:
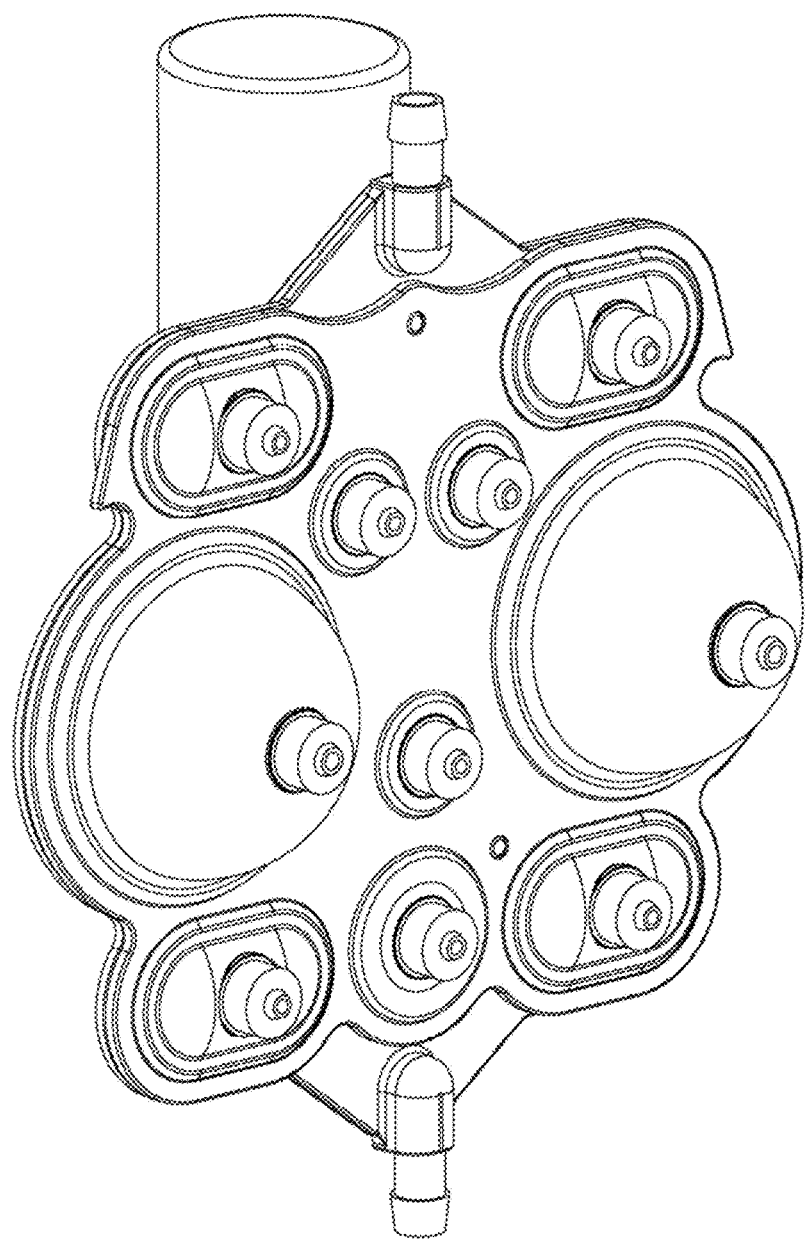
FIG. 21B is a bottom view of an assembled alternate embodiment of the cassette with a vial.
Figure 21C:
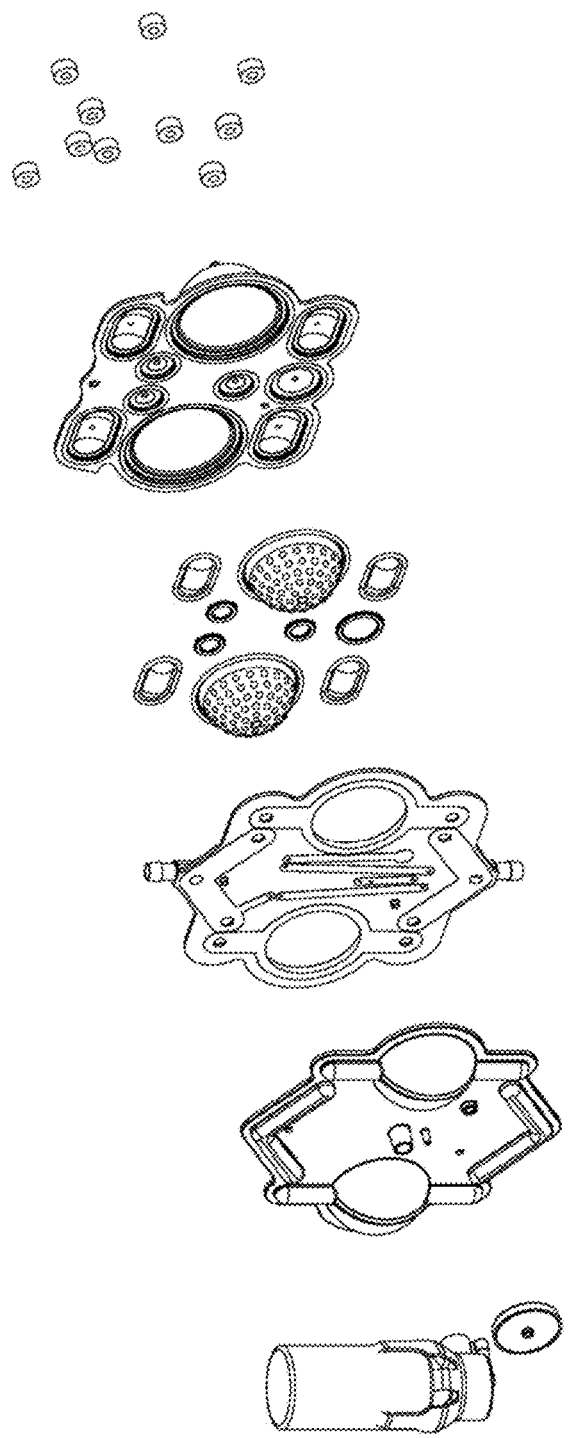
FIG. 21C is an exploded view of the assembled alternate embodiment of the cassette with a vial.
Figure 21D:
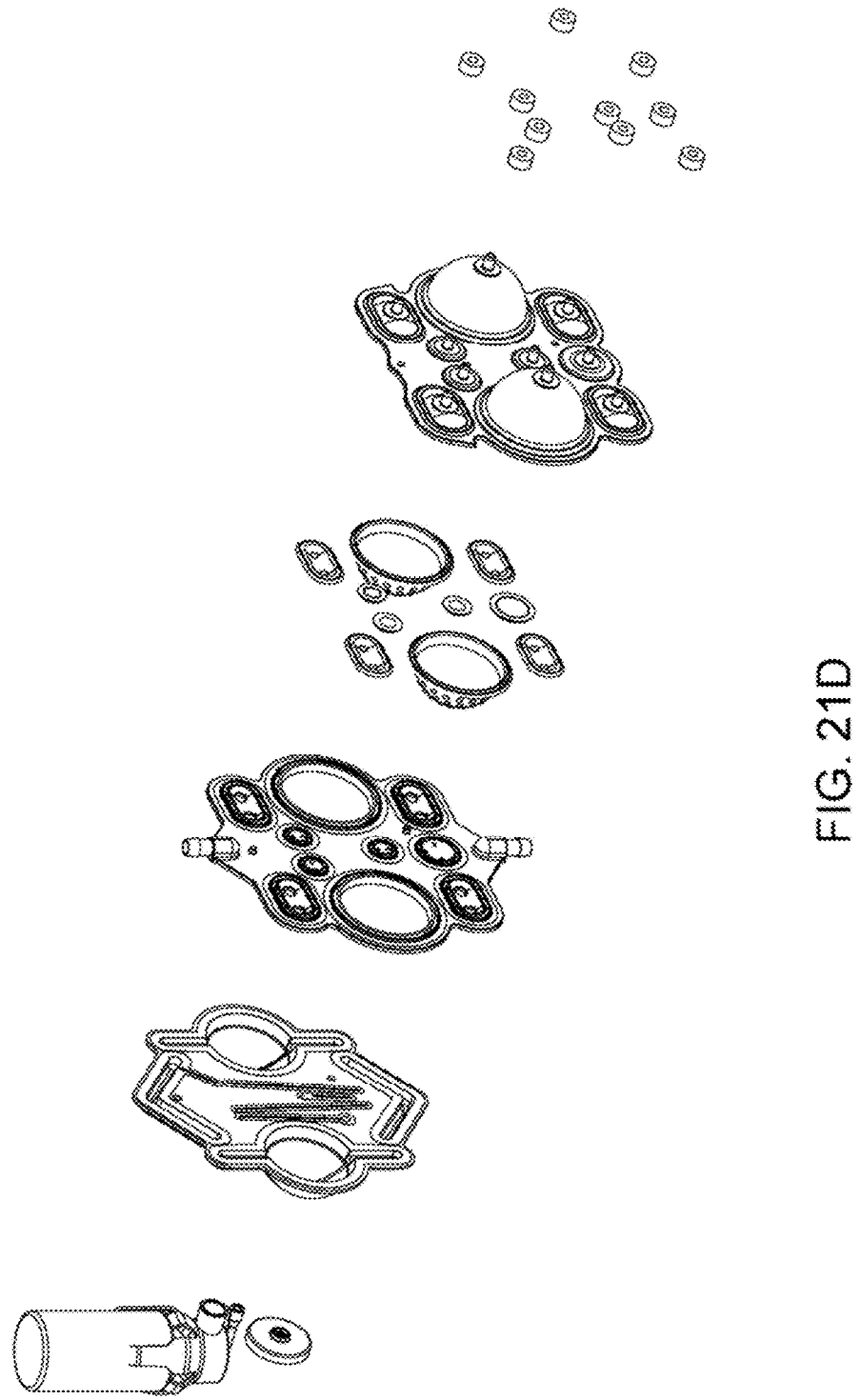
FIG. 21D is an exploded view of the assembled alternate embodiment of the cassette with a vial.
Figure 22A:
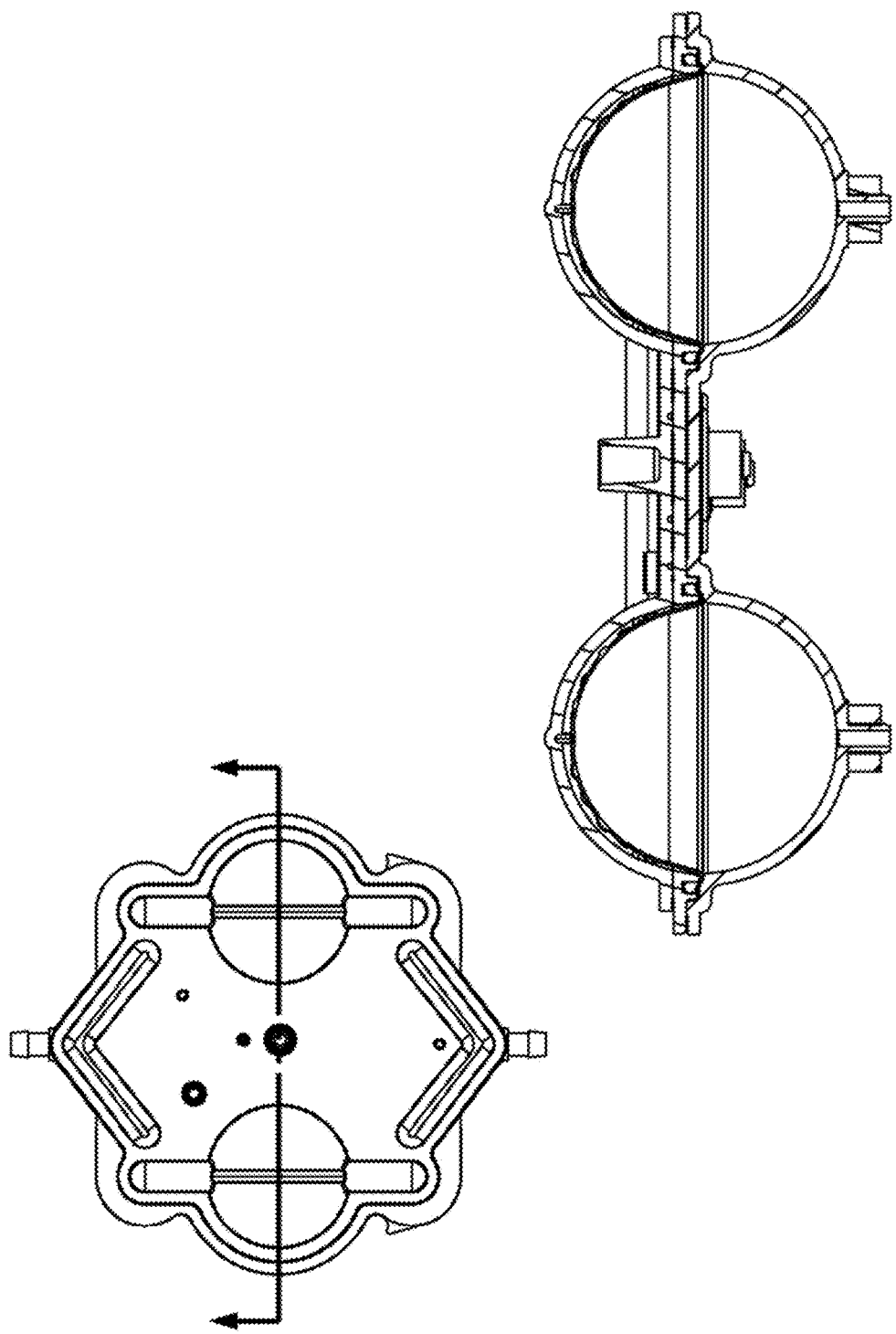
FIGS. 22A-22B show cross sectional views of an alternate embodiment of the assembled cassette.
Figure 22B:
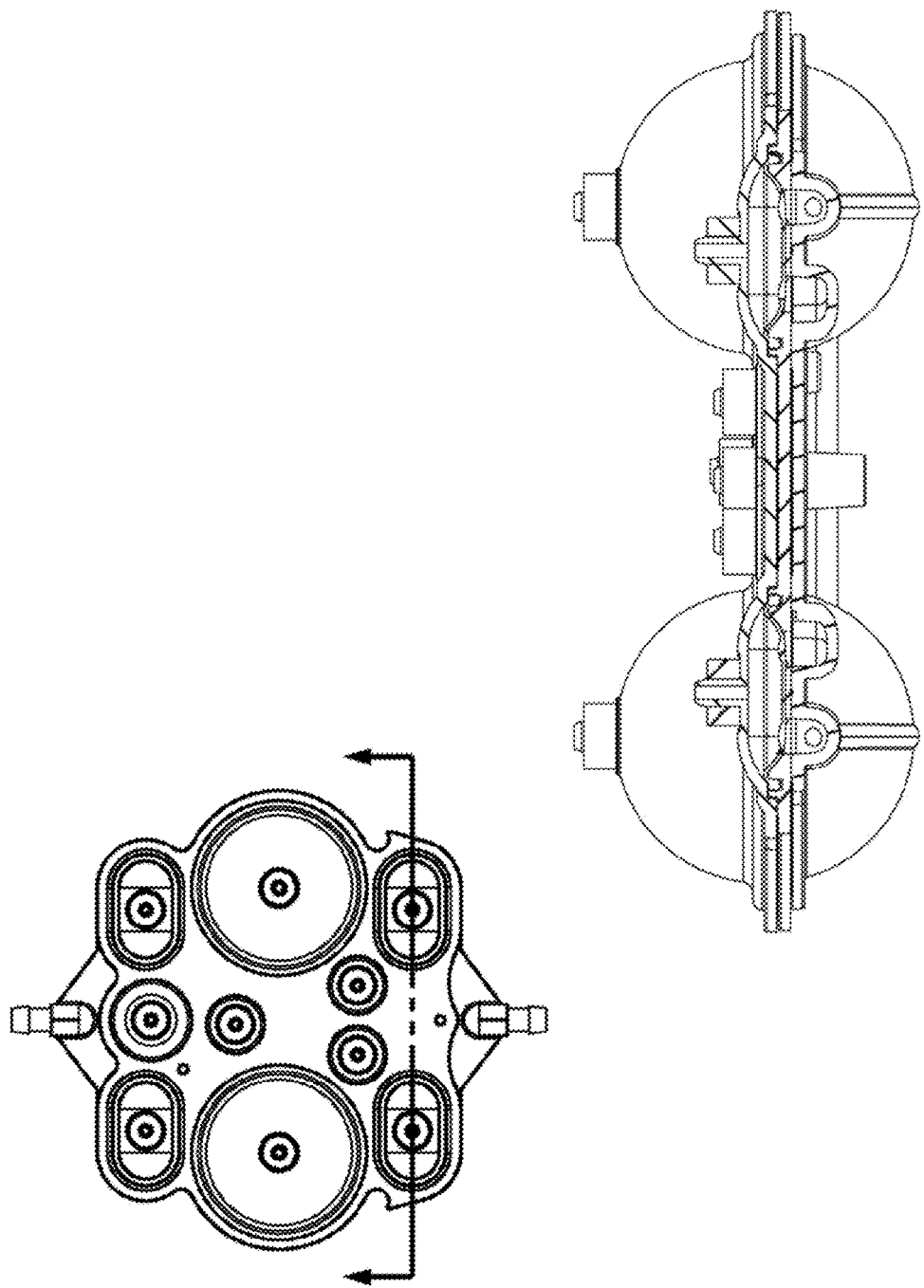

Referring now to FIGS. 3A-4B, a raised flow path 30 is shown in the pumping chamber. This raised flow path 30 allows for the fluid to continue flowing through the pod pumps after the membrane reaches the end of stroke. Thus, the raised flow path 30 minimizes the chances of the membrane causing air or fluid to be trapped in the pod pump or the membrane blocking the inlet or outlet of the pod pump which would inhibit continuous flow. Further description of the raised flow path is shown and described below with respect to FIGS. 9A-9B and FIGS. 18A-18E. The raised flow path 30 is shown in the exemplary embodiment having particular dimensions, however, in alternate embodiments, as seen in FIGS. 18A-18B, the raised flow path 30 is narrower, or in still other embodiments, the raised flow path 30 can be any dimensions as the purpose is to control fluid flow so as to achieve a desired flow rate or behavior of the fluid. Thus, the dimensions shown and described here with respect to the raised flow path, the pod pumps, the valves or any other aspect are mere exemplary and alternate embodiments. Other embodiments are readily apparent.

Thus, for example, when the fluid being pumped is whole blood, centrifugal pumps (which apply a great deal of stress on the red blood cells) can cause a large amount of hemolysis and to the detriment of the patient, whereas pod pumps of the types described above (which apply low shear forces and turbulence) tend to produce substantially lower hemolysis. Similarly, when the fluid being pumped is a surfactant or other fluid prone to foaming, the reduced shear forces and reduced turbulence of the pod pumps tend to reduce foaming.

Generally speaking, for low shear and/or low turbulence applications, it is desirable for the inlet and outlet to be configured so as to avoid sharp or abrupt changes of fluid direction. It is also generally desirable for the inlet and outlet (and the pump chamber itself) to be free of flash or burrs. The inlet and/or outlet may include rounded edges to help smooth out fluid flow. However, although this benefit has been described with respect to whole blood, this was only for example, the cassette pumps any fluid and the benefits described with respect to shear sensitive fluids or biological fluids may apply to other fluids as well.

1.3 Exemplary Balancing Pods Embodiment

Referring now to FIG. 1B, an exemplary embodiment of a balancing pod is shown. The balancing pod is constructed similar to the pod pump described above with respect to FIG. 1A. However, a balancing pod includes two fluid balancing chambers, rather than an actuation chamber and a pumping chamber, and does not include an actuation port. Additionally, each balancing chamber includes an inlet 102 and an outlet 104. In the exemplary embodiment, a groove 126 is included on each of the balancing chamber walls 120, 122. The groove 126 is described in further detail below.

The membrane 112 provides a seal between the two chambers. The balancing chambers work to balance the flow of fluid into and out of the chambers such that both chambers maintain an equal volume rate flow Although the inlets 102 and outlets 104 for each chamber are shown to be on the same side, in other embodiments, the inlets 102 and outlets 104 for each chamber are on different sides. Also, the inlets 102 and outlets 104 can be on either side, depending on the flow path in which the balancing chamber is integrated.

In one embodiment of the balancing chambers the membrane 112 includes an embodiment similar to the one described below with respect to FIGS. 6A-6G. However, in alternate embodiments, the membrane 112 can be over molded or otherwise constructed such that a double-ring seal is not applicable.

1.4 Metering Pumps and Fluid Management System

The metering pump can be any pump that is capable of adding any fluid or removing any fluid. The fluids include but are not limited to pharmaceuticals, inorganic compounds or elements, organic compounds or elements, nutraceuticals, nutritional elements or compounds or solutions, or any other fluid capable of being pumped. In one embodiment, the metering pump is a membrane pump. In the exemplary embodiment, the metering pump is a smaller volume pod pump. In the exemplary embodiment, the metering pump includes an inlet and an outlet, similar to a larger pod pump (as shown in FIG. 1A for example). However, the inlet and outlet are generally much smaller than a pod pump and, in one exemplary embodiment, includes a volcano valve-like raised ring around either the inlet or outlet. Metering pumps include a membrane, and various embodiments of a metering pump membrane are shown in FIGS. 5E-5H. The metering pump, in some embodiments, pumps a volume of fluid out of the fluid line. Once the fluid is in the pod pump, a reference chamber, located outside the cassette, using the FMS, determines the volume that has been removed.

Thus, depending on the embodiment, this volume of fluid that has been removed will not then flow to the fluid outlet, the balance chambers or to a pod pump. Thus, in some embodiments, the metering pump is used to remove a volume of fluid from a fluid line. In other embodiments, the metering pump is used to remove a volume of fluid to produce other results.

FMS may be used to perform certain fluid management system measurements, such as, for example, measuring the volume of subject fluid pumped through the pump chamber during a stroke of the membrane or detecting air in the pumping chamber, e.g., using techniques described in U.S. Pat. Nos. 4,808,161; 4,826,482; 4,976,162; 5,088,515; and 5,350,357, which are hereby incorporated herein by reference in their entireties.

Metering pumps are also used in various embodiments to pump a second fluid into the fluid line. In some embodiments, the metering pump is used to pump a therapeutic or a compound into a fluid line. One embodiment uses the metering pump to pump a volume of compound into a mixing chamber in order to constitute a solution. In some of these embodiments, the metering pumps are configured for FMS volume measurement. In other embodiments, the metering pumps are not.

For FMS measurement a small fixed reference air chamber is located outside of the cassette, for example, in the pneumatic manifold (not shown). A valve isolates the reference chamber and a second pressure sensor. The stroke volume of the metering pump may be precisely computed by charging the reference chamber with air, measuring the pressure, and then opening the valve to the pumping chamber. The volume of air on the chamber side may be computed based on the fixed volume of the reference chamber and the change in pressure when the reference chamber was connected to the pump chamber.

1.5 Valves

Figure 2A:
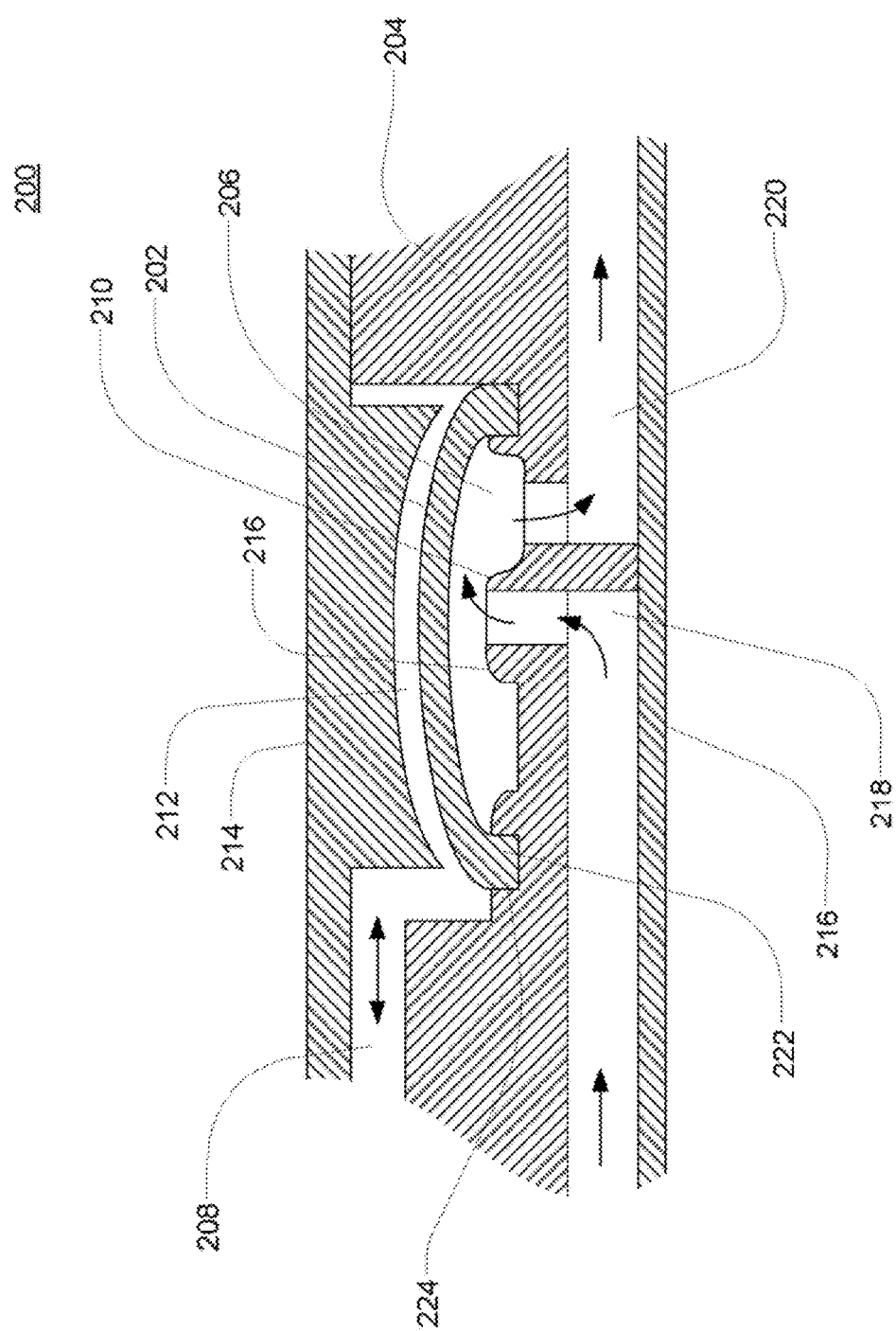
FIG. 2A is an illustrative sectional view of one embodiment of one type of pneumatically controlled valve that is incorporated into some embodiments of the cassette.
Figure 2B:
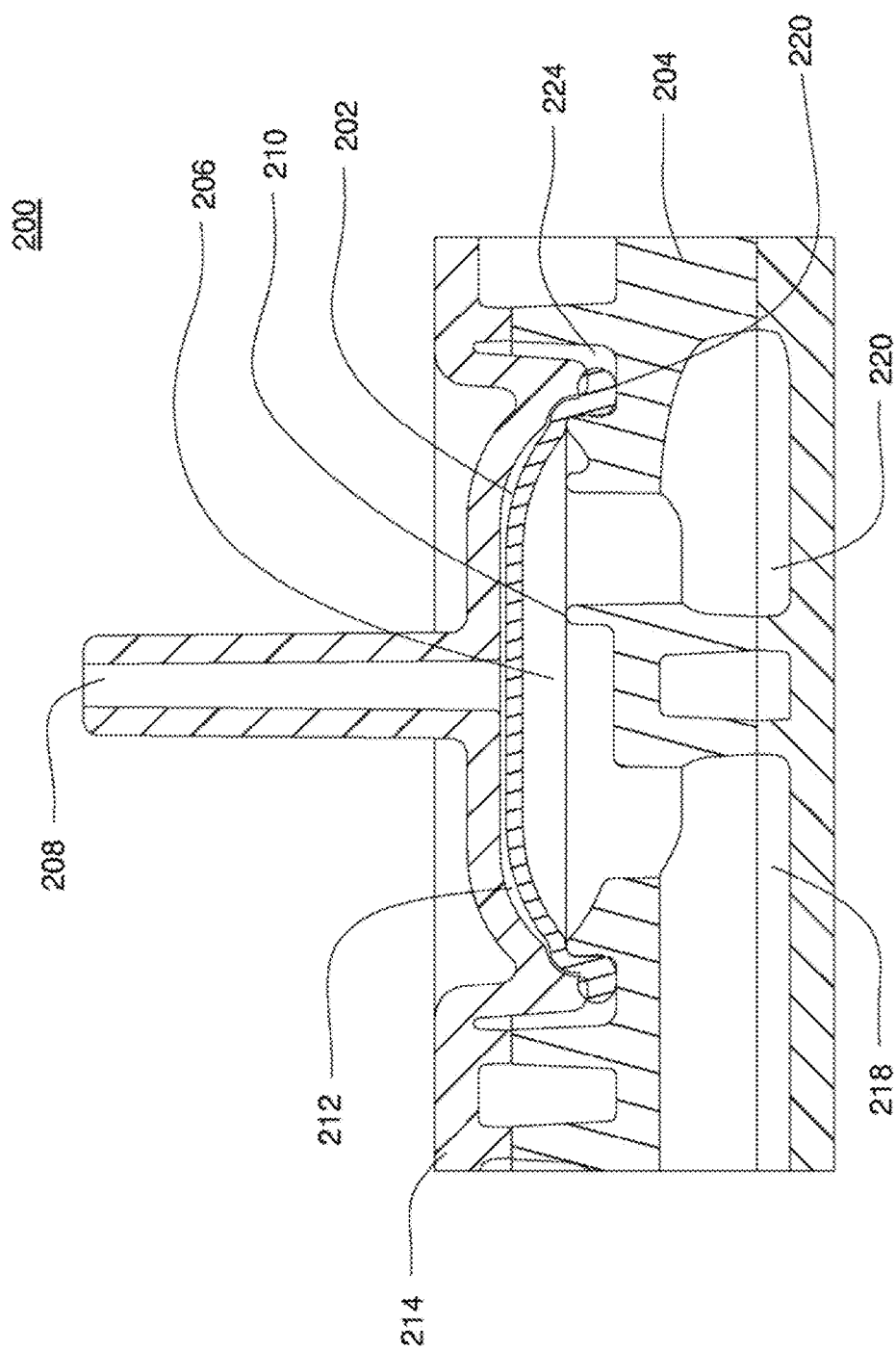
FIG. 2B is a sectional view of another embodiment of one type of pneumatically controlled valve that is incorporated into some embodiments of the cassette.

The exemplary embodiment of the cassette includes one or more valves. Valves are used to regulate flow by opening and closing fluid lines. The valves included in the various embodiments of the cassette include one or more of the following; volcano valves or smooth valves. In some embodiment of the cassette, check valves may be included. Embodiments of the volcano valve are shown in FIGS. 2A and 2B, while an embodiment of the smooth valve is shown in FIG. 2C. Additionally, FIGS. 3A-4B show cross sections of an exemplary embodiment of the pod pump in a cassette with an inlet and outlet valve.

Generally speaking, reciprocating positive-displacement pomps of the types just described may include, or may be used in conjunction with, various valves to control fluid flow through the pump. Thus, for example, the reciprocating positive-displacement pump or the balancing pods may include, or be used in conjunction with, an inlet valve and/or an outlet valve. The valves may be passive or active. In the exemplary embodiment of the reciprocating positive-displacement pump the membrane is urged back and forth by positive and negative pressurizations, or by positive and vent to atmosphere pressurizations, of a gas provided through the pneumatic port, which connects the actuation chamber to a pressure actuation system. The resulting reciprocating action of the membrane pulls fluid into the pumping chamber from the inlet (the outlet valve prevents liquid from being sucked back into the pumping chamber from the outlet) and then pushes the fluid out of the pumping chamber through the outlet (the inlet valve prevents fluid from being forced back from the inlet).

In the exemplary embodiments, active valves control the fluid flow through the pump(s) and the cassette. The active valves may be actuated by a controller in such a manner as to direct flow in a desired direction. Such an arrangement would generally permit the controller to cause flow in either direction through the pod pump. In a typical system, the flow would normally be in a first direction, e.g., from the inlet to the outlet. At certain other times, the flow may be directed in the opposite direction, e.g., from the outlet to the Inlet. Such reversal of flow may be employed, for example, during priming of the pump, to check for an aberrant line condition (e.g., a line occlusion, blockage, disconnect, or leak), or to clear an aberrant line condition (e.g., to try to dislodge a blockage).

Pneumatic actuation of valves provides pressure control and a natural limit to the maximum pressure that may be developed in a system. In the context of a system, pneumatic actuation has the added benefit of providing the opportunity to locate all the solenoid control valves on one side of the system away from the fluid paths.

Referring now to FIGS. 2A and 2B, sectional views of two embodiments of a volcano valve are shown. The volcano valves are pneumatically controlled valves that may be used in embodiments of the cassette. A membrane 202, along with the midplate 204, defines a valving chamber 206. Pneumatic pressure is provided through a pneumatic port 208 to either force, with positive gas pressure, the membrane 202 against a valve seat 210 to close the valve, or to draw, with negative gas pressure, or in some embodiments, with vent, to atmospheric pressure, the membrane away from the valve seat 210 to open the valve, A control gas chamber 212 is defined by the membrane 202, the top plate 214, and the midplate 204. The midplate 204 has an indentation formed on it, into which the membrane 202 is placed so as to form the control gas chamber 212 on one side of the membrane 202 and the valving chamber 206 on the other side.

The pneumatic port 208 is defined by a channel formed in the top plate 214. By providing pneumatic control of several valves in a cassette, valves can be ganged together so that all the valves ganged together can be opened or closed at the same time by a single source of pneumatic pressure. Channels formed on the midplate 204, corresponding with fluid paths along with the bottom plate 216, define the valve inlet 218 and the valve outlet 220. Holes formed through the midplate 204 provide communication between the inlet 218 and the valving chamber 206 and between the valving chamber 206 and the outlet 220.

The membrane 202 is provided with a thickened rim 222, which fits tightly in a groove 224 in the midplate 204. Thus, the membrane 202 can be placed in and held by the groove 224 before the top plate 214 is connected to the midplate 204. Thus, this valve design may impart benefits in manufacture. As shown in FIGS. 2B and 2C, the top plate 214 may include additional material extending into control gas chamber 212 so as to prevent the membrane 202 from being urged too much in a direction away from the groove 224, so as to prevent the membrane's thickened rim 222 from popping out of the groove 224. The location of the pneumatic port 208 with respect to the control gas chamber 212 varies in the two embodiments shown in FIGS. 2A and 2B.

Figure 2D:
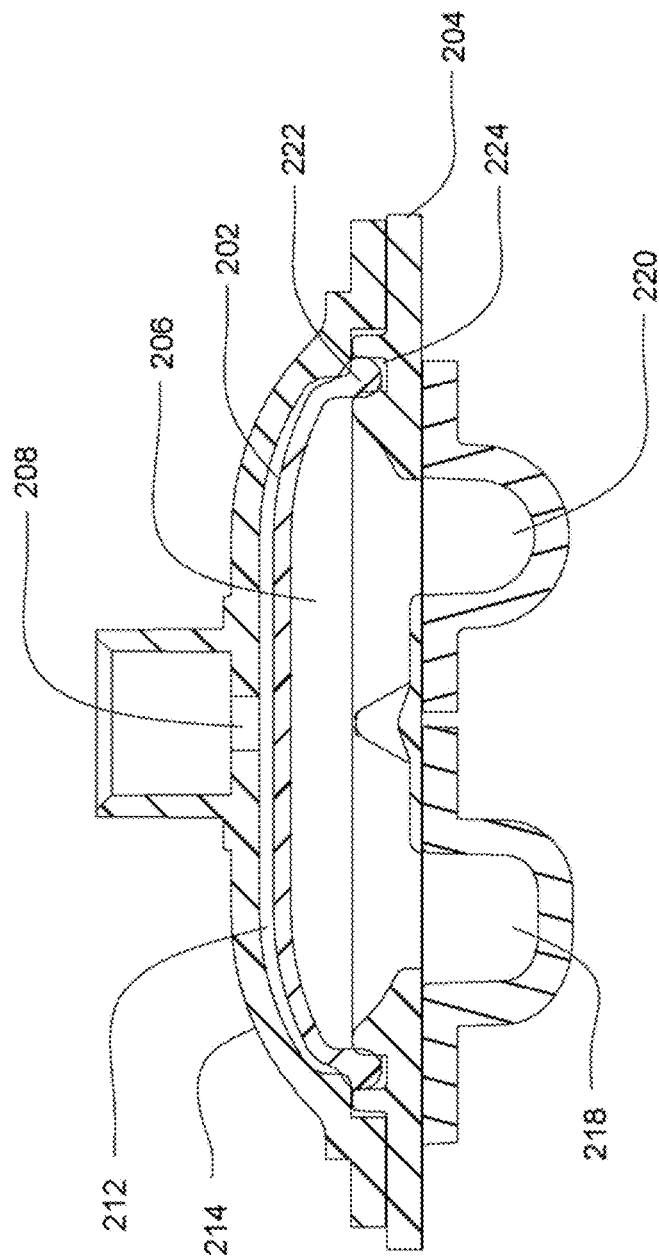
FIG. 2D is a sectional view of another embodiment of one type of pneumatically controlled valve that is incorporated into some embodiments of the cassette.
Figure 2E:
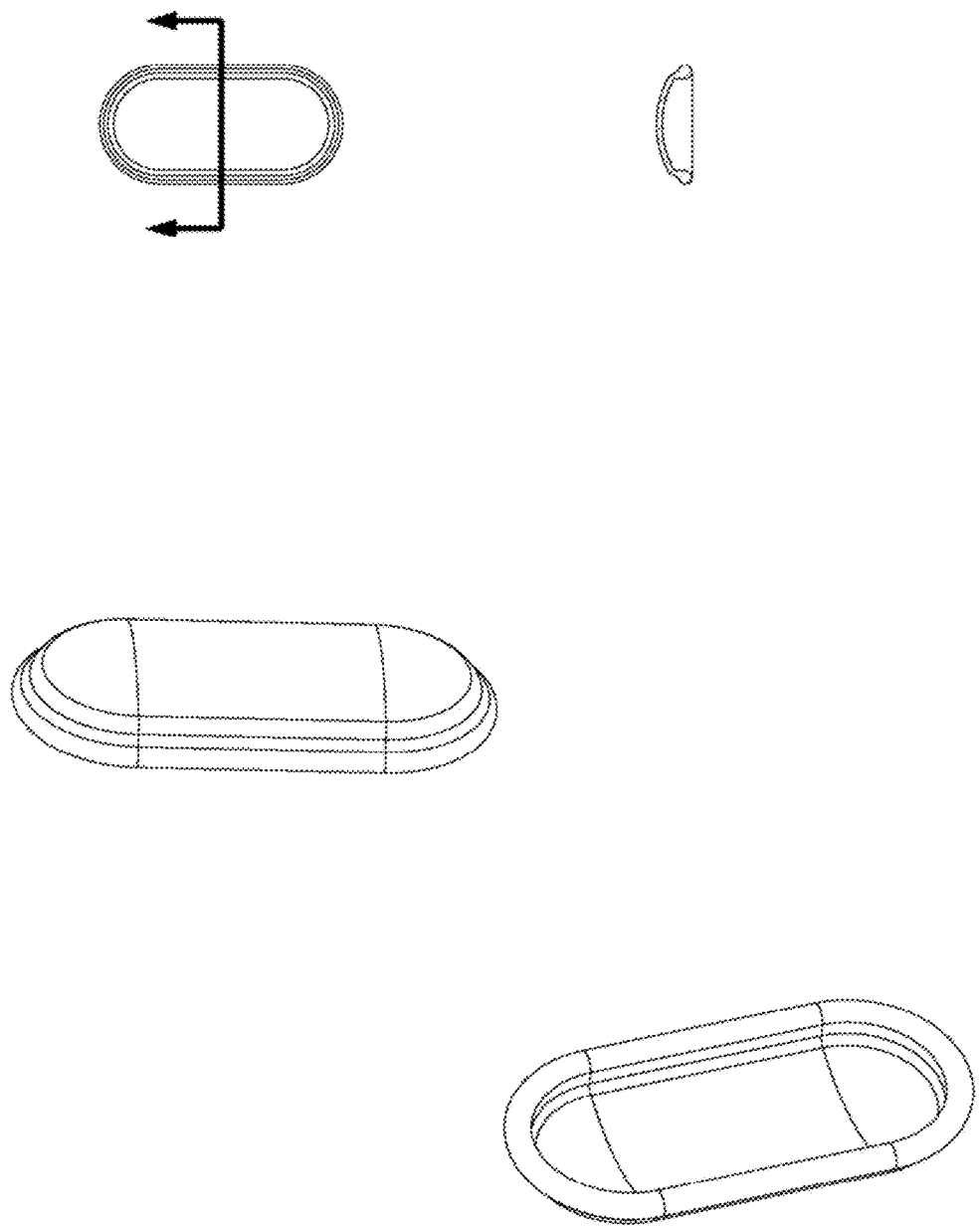

FIG. 2C shows an embodiment in which the valving chamber lacks a valve seat feature. Rather, in FIG. 2C, the valve in this embodiment does not include any volcano features and thus, the valving chamber 206, i.e., the fluid side, does not include any raised features and thus is smooth. This embodiment is used in cassettes used to pump fluid sensitive to shearing. FIG. 2D shows an embodiment in which the valving chamber has a raised area to aid in the sealing of the valving membrane. Referring now to FIGS. 2E-2G, various embodiments of the valve membrane are shown. Although some exemplary embodiments have been shown and described, in other embodiments, variations of the valve and valving membrane may be used.

1.6 Exemplary Embodiments of the Pod Membrane

In some embodiments, the membrane has a variable cross-sectional thickness, as shown in FIG. 4. Thinner, thicker or variable thickness membranes may be used to accommodate the strength, flexural and other properties of the chosen membranes materials. Thinner, thicker or variable membrane wall thickness may also be used to manage the membrane thereby encouraging it to flex more easily in some areas than in other areas, thereby aiding in the management, of pumping action and flow of subject, fluid in the pump chamber. In this embodiment the membrane is shown having its thickest cross-sectional area closest to its center. However in other embodiments having a membrane with a varying cross-sectional, the thickest and thinnest areas may be in any location on the membrane. Thus, for example, the thinner cross-section may be located near the center and the thicker cross-sections located closer to the perimeter of the membrane. Still other configurations are possible. Referring to FIGS. 5A-5D, one embodiment of a membrane is shown having various surface embodiments, these include smooth (FIG. 5A), rings (FIG. 5D), ribs (FIG. 5C), dimples or dots (FIG. 5B) of variable thickness and or geometry located at various locations on the actuation and or pumping side of the membrane. In one embodiment of the membrane, the membrane has a tangential slope in at least one section, but in other embodiments, the membrane is completely smooth or substantially smooth.

Figure 4C:
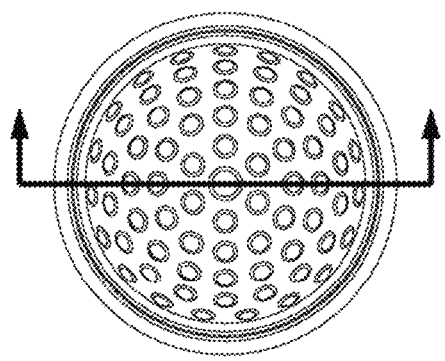
FIGS. 4C and 4D are top and section views respectively of a pod pump within a cassette having a dimpled/variable membrane.
Figure 4D:
Figure 4E:
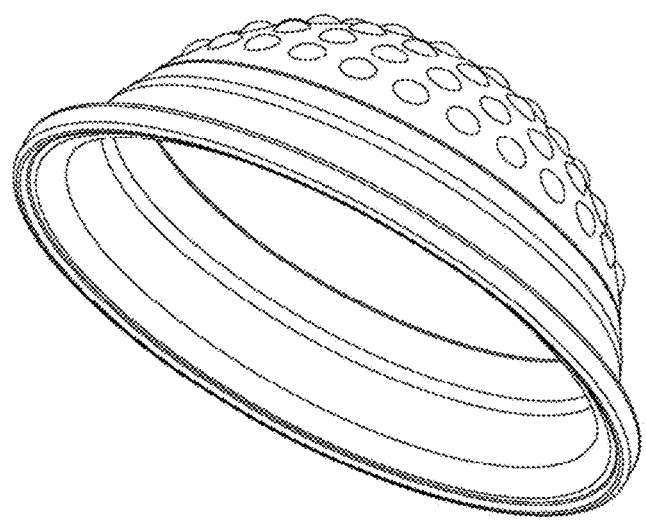
FIGS. 4E and 4F are pictorial views of a single ring membrane with a variable surface.
Figure 4F:
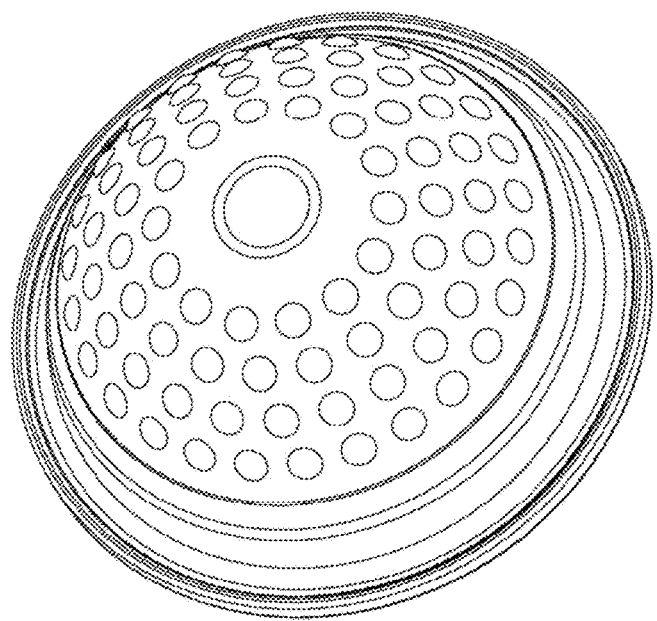
Figure 5A:
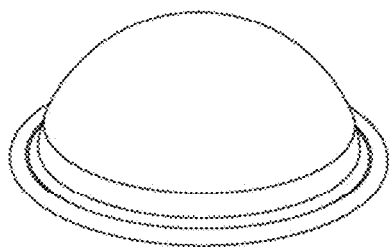
FIGS. 5A-5D are pictorial views of various embodiments of variable membranes.
Figure 5B:
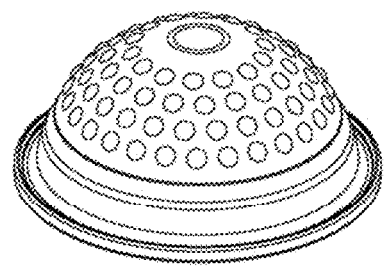
Figure 5C:
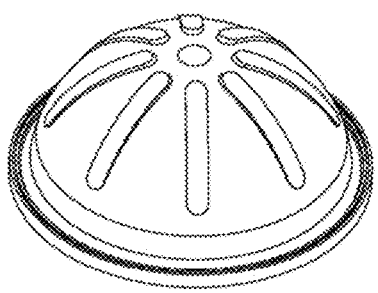
Figure 5D:
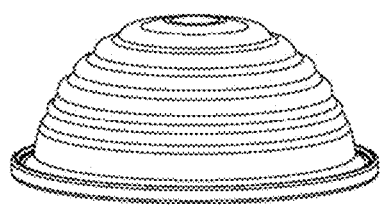
Figure 5E:
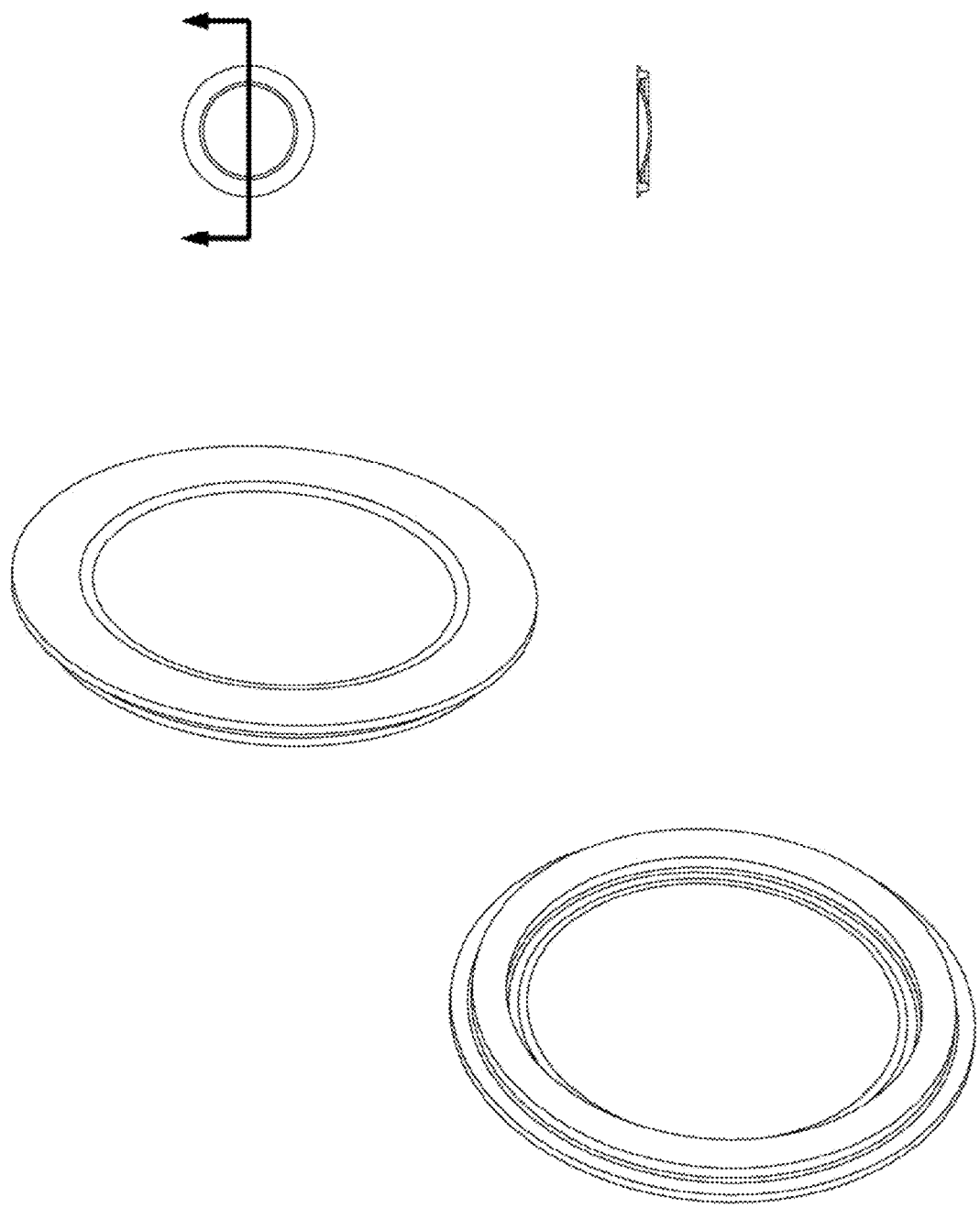
Figure 5G:
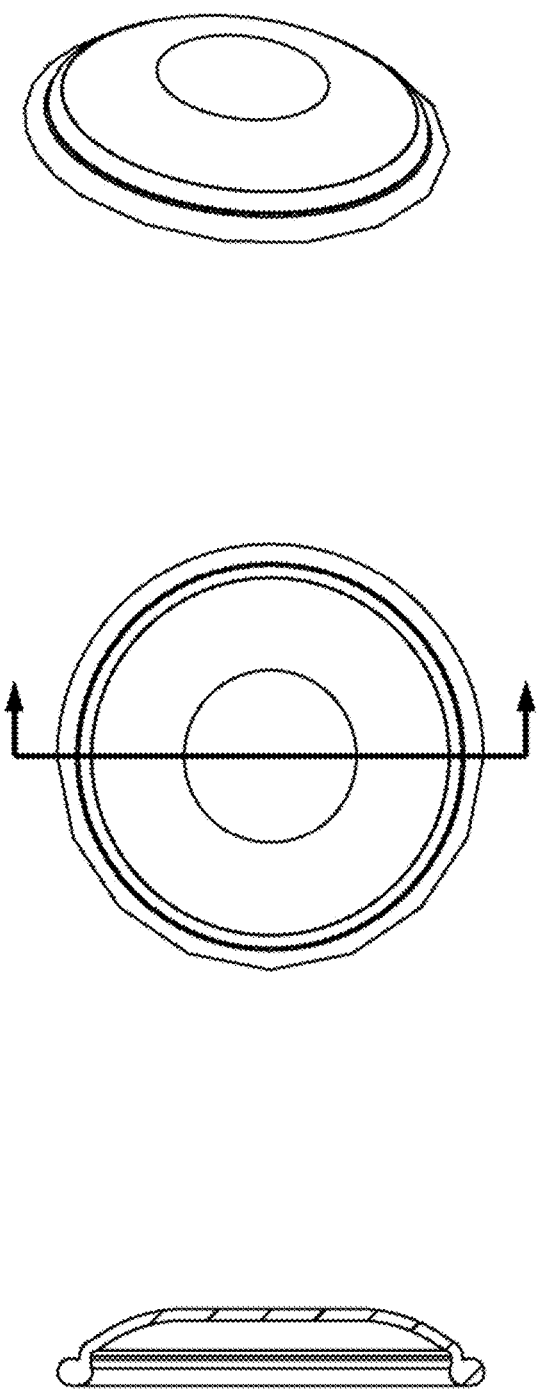
Figure 5H:
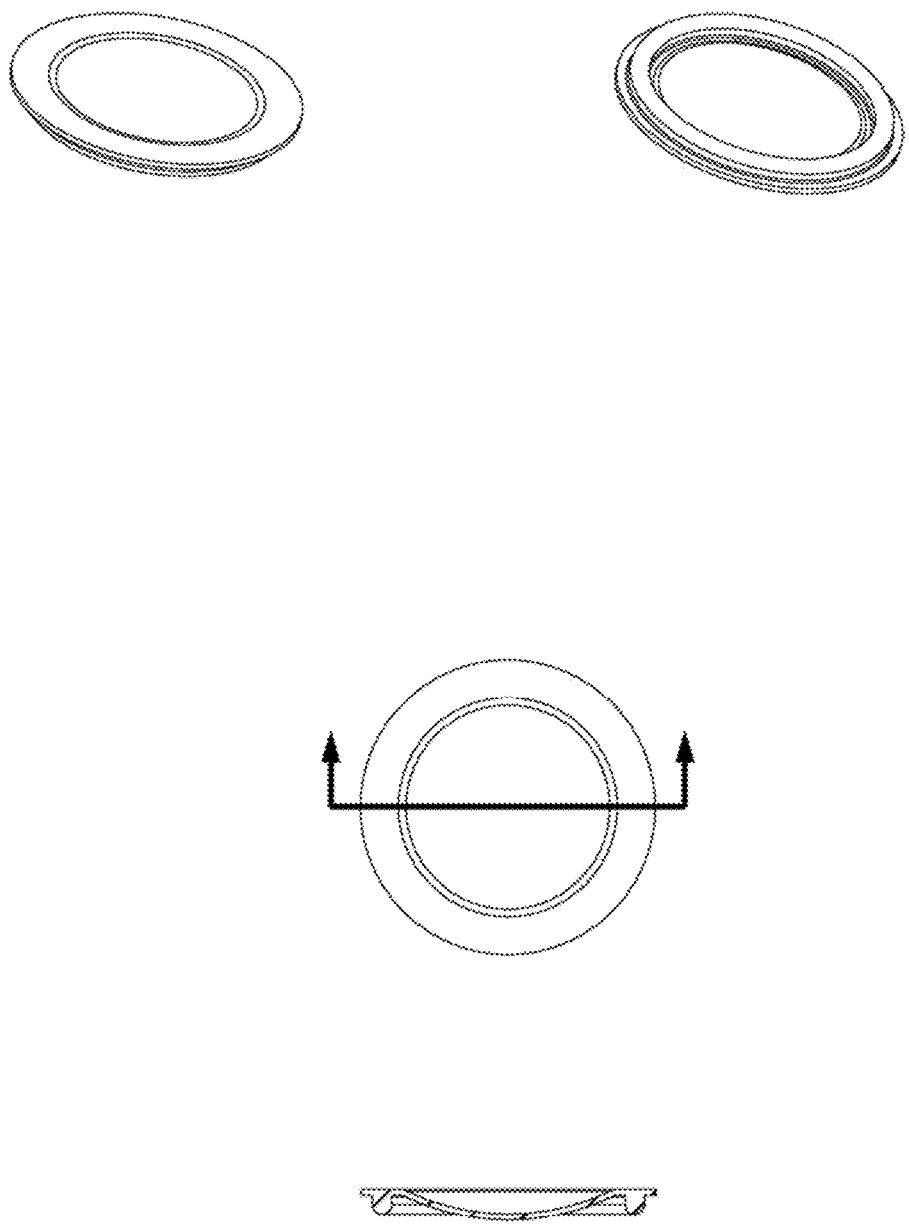
Figure 6A:
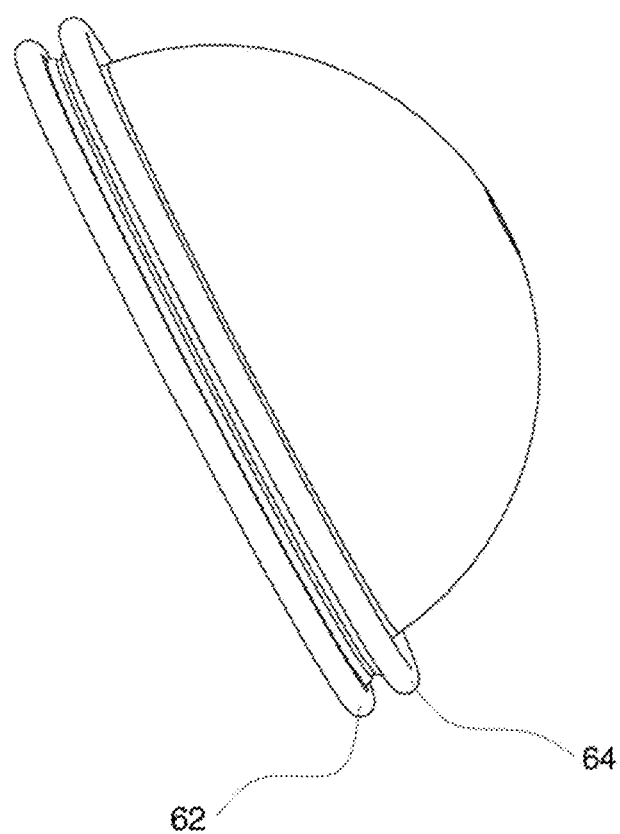
FIGS. 6A and 6B are pictorial views of a double ring membrane with a smooth surface.
Figure 6B:
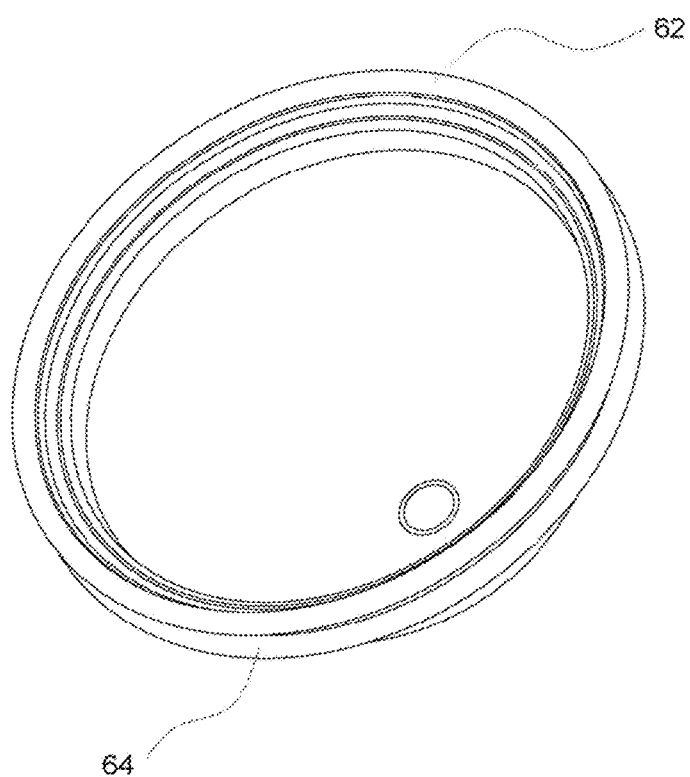
Figure 6C:
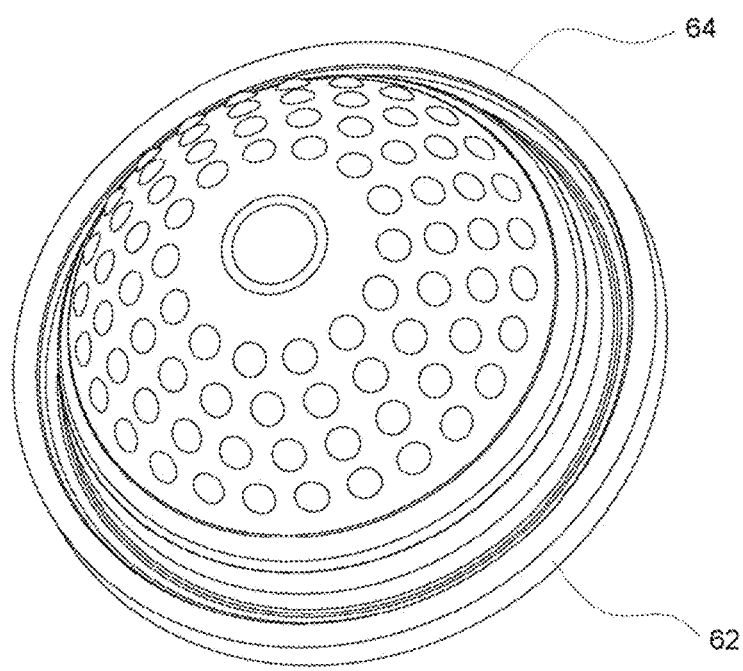
FIGS. 6C and 6D are pictorial views of a double ring membrane with a dimple surface.
Figure 6D:
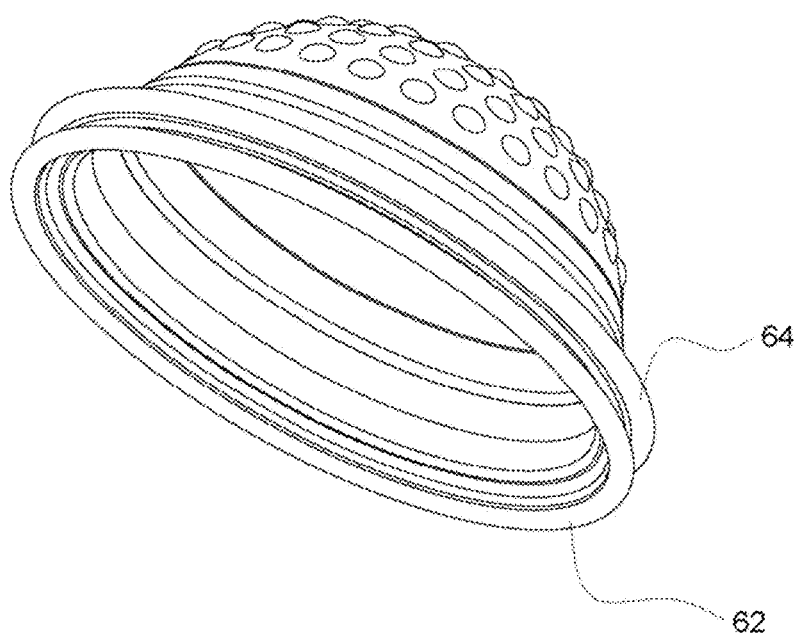
Figure 6E:
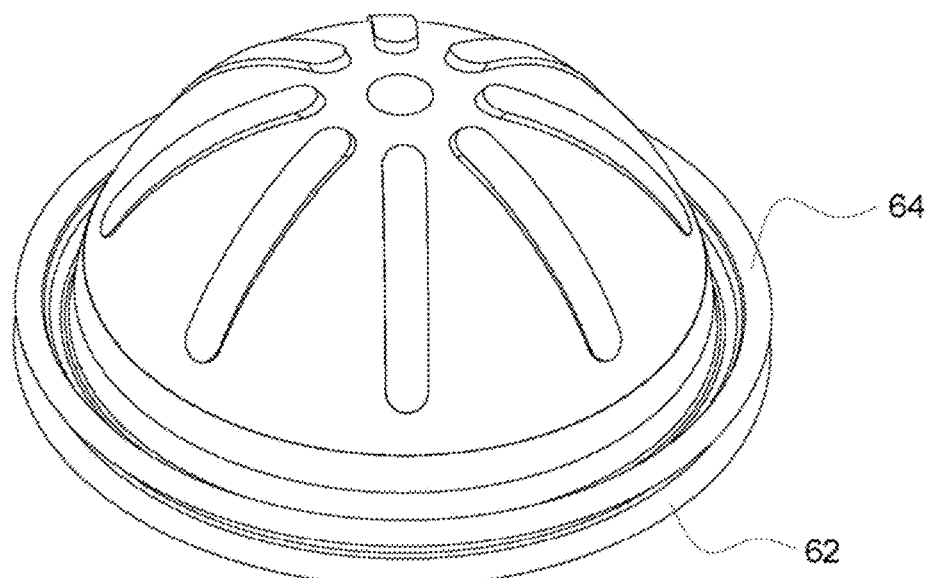
FIGS. 6E and 6F are pictorial views of double ring membranes with variable surfaces.
Figure 6F:
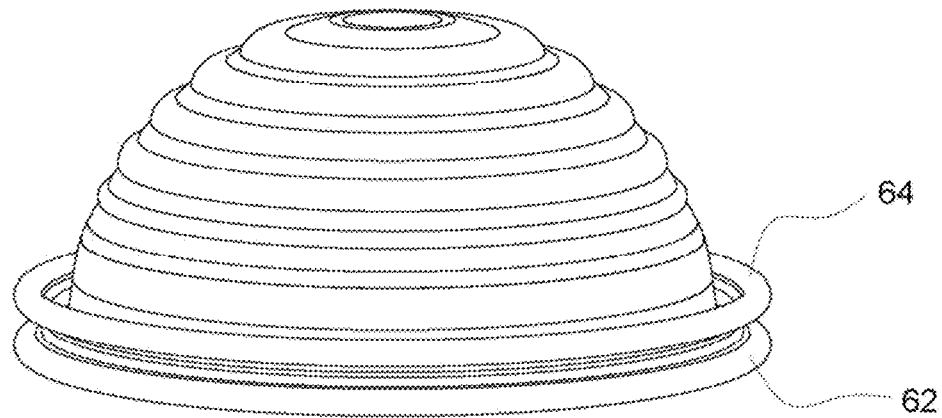

Referring now to FIGS. 4C, 4E and 4F, an alternate embodiment of the membrane is shown. In this embodiment, the membrane has a dimpled or dotted surface.

The membrane may be made of any flexible material having a desired durability and compatibility with the subject fluid. The membrane can be made from any material that may flex in response to fluid, liquid or gas pressure or vacuum applied to the actuation chamber. The membrane material may also be chosen for particular bio-compatibility, temperature compatibility or compatibility with various subject fluids that may be pumped by the membrane or introduced to the chambers to facilitate movement of the membrane. In the exemplary embodiment, the membrane is made from high elongation silicone. However, in other embodiments, the membrane is made from any elastomer or rubber, including, but not limited to, silicone, urethane, nitrile, EPDM or any other rubber, elastomer or flexible material, The shape of the membrane is dependent on multiple variables. These variables include, but are not limited to: the shape of the chamber; the size of the chamber; the subject fluid characteristics; the volume of subject fluid pumped per stroke; and the means or mode of attachment of the membrane to the housing. The size of the membrane is dependent on multiple variables. These variables include, but are not limited to: the shape of the chamber; the size of the chamber; the subject fluid characteristics; the volume of subject fluid pumped per stroke; and the means or mode of attachment of the membrane to the housing. Thus, depending on these or other variables, the shape and size of the membrane may vary in various embodiments.

The membrane can have any thickness. However, in some embodiments, the range of thickness is between 0.002 inches to 0.125 inches. Depending on the material used for the membrane, the desired thickness may vary. In one embodiment, high elongation silicone is used in a thickness ranging from 0.015 inches to 0.050 inches. However in other embodiments, the thickness may vary.

In the exemplary embodiment, the membrane is pre-formed to include a substantially dome-shape in at least part of the area of the membrane. One embodiment of the dome-shaped membrane is shown in FIGS. 4E and 4F. Again, the dimensions of the dome may vary based on some or more of the variables described above. However, in other embodiments, the membrane may not include a pre-formed dome shape.

In the exemplary embodiment, the membrane dome is formed using liquid injection molding. However, in other embodiments, the dome may be formed by using compression molding. In alternate embodiments, the membrane is substantially flat. In other embodiments, the dome size, width or height may vary.

In various embodiments, the membrane may be held in place by various means and methods. In one embodiment, the membrane is clamped between the portions of the cassette, and in some of these embodiments, the rim of the cassette may include features to grab the membrane. In others of this embodiment, the membrane is clamped to the cassette using at least one bolt or another device. In another embodiment, the membrane is over-molded with a piece of plastic and then the plastic is welded or otherwise attached to the cassette. In another embodiment the membrane is pinched between the mid plate described with respect to FIGS. 1A and 1B and the bottom plate. Although some embodiments for attachment of the membrane to the cassette are described, any method or means for attaching the membrane to the cassette can be used. The membrane, in one alternate embodiment, is attached directly to one portion of the cassette. In some embodiments, the membrane Is thicker at the edge, where the membrane is pinched by the plates, than in other areas of the membrane. In some embodiments, this thicker area is a gasket, in some embodiments an O-ring, ring or any other shaped gasket. Referring again to 6A-6D, one embodiment of the membrane is shown with two gaskets 62, 64. In some of these embodiments, the gasket(s) 62, 64 provides the attachment point of the membrane to the cassette. In other embodiments, the membrane includes more than two gaskets. Membranes with one gasket are also included in some embodiments (see FIGS. FIGS. 4C-4F).

In some embodiments of the gasket, the gasket is contiguous with the membrane. However, in other embodiments, the gasket is a separate part of the membrane, hi some embodiments, the gasket is made from the same material as the membrane. However, in other embodiments, the gasket is made of a material different from the membrane. In some embodiments, the gasket is formed by over-molding a ring around the membrane. The gasket can be any shape ring or seal desired so as to complement the pod pump housing embodiment. In some embodiments, the gasket is a compression type gasket.

1.7 Mixing Pods

Some embodiments of the cassette include a mixing pod. A mixing pod includes a chamber for mixing. In some embodiments, the mixing pod is a flexible structure, and in some embodiments, at least a section of the mixing pod is a flexible structure. The mixing pod can include a seal, such as an o-ring, or a membrane. The mixing pod can be any shape desired. In the exemplary embodiment, the mixing pod is similar to a pod pump except it does not include a membrane and does not include an actuation port. Some embodiments of this embodiment of the mixing pod include an o-ring seal to seal the mixing pod chamber. Thus, in the exemplary embodiment, the mixing pod is a spherical hollow pod with a fluid inlet and a fluid outlet. As with the pod pumps, the chamber size can be any size desired.

2. Pressure Pump Actuation System

Figure 7:
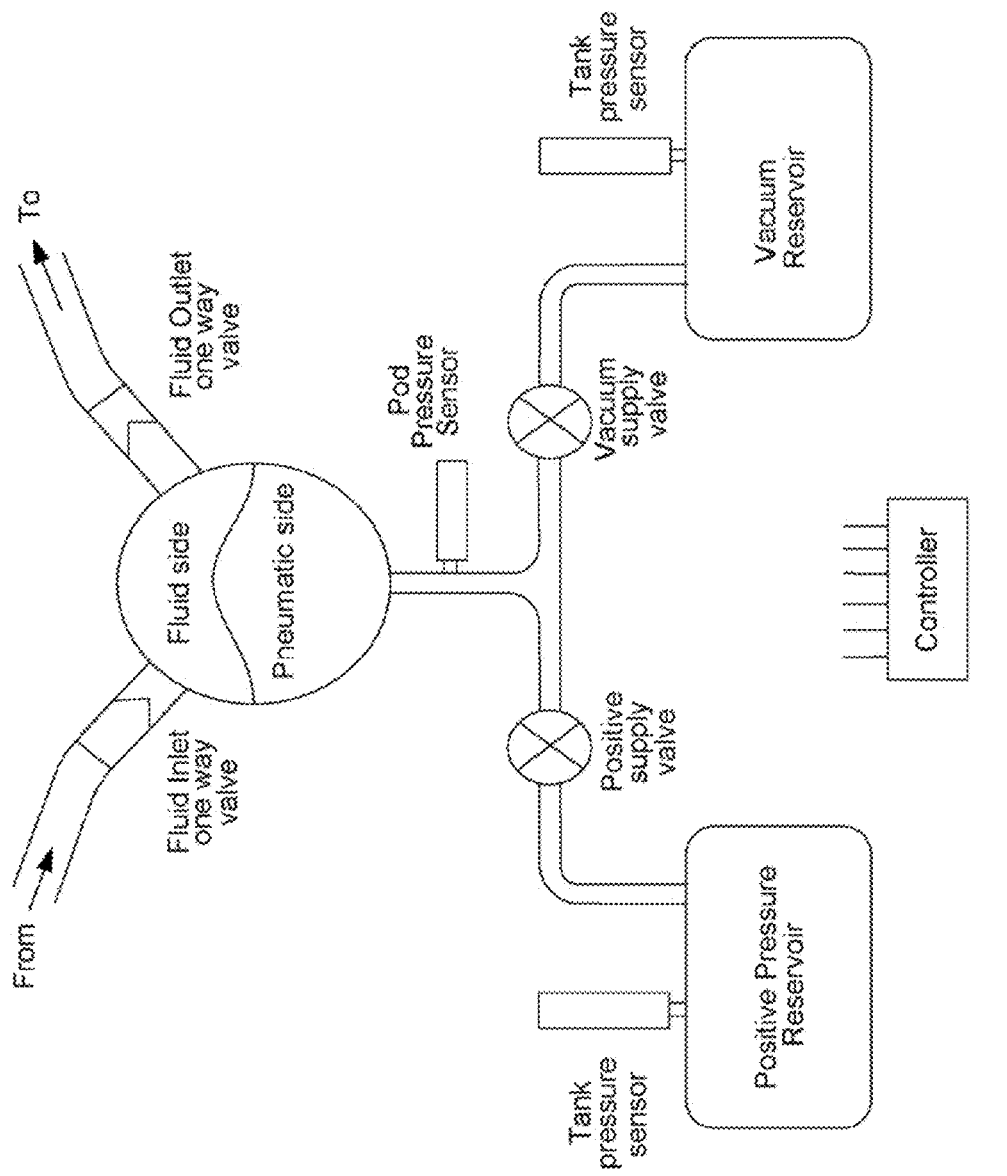
FIG. 7 is a schematic showing a pressure actuation system that may be used to actuate a pod pump.

FIG. 7 is a schematic showing one embodiment of a pressure actuation system that may be used to actuate a pod pump with both positive and negative pressure, such as the pod pump shown in FIG. 1A. The pressure actuation system is capable of intermittently or alternately providing positive and negative pressurizations to the gas in the actuation chamber of the pod pump. However, in some embodiments, FIG. 7 does not apply for in these embodiments, actuation of the pod pump is accomplished by applying positive pressure and vent to atmosphere (again, not shown in FIG. 7). The pod pump—including the flexible membrane, the inlet, the outlet, the pneumatic port, the pumping chamber, the actuation chamber, and possibly including an inlet check valve and an outlet check valve or other valves—is part of a larger disposable system. The pneumatic actuation system—including an actuation-chamber pressure transducer, a positive-supply valve, a negative-supply valve, a positive-pressure gas reservoir, a negative-pressure gas reservoir, a positive-pressure-reservoir pressure transducer, a negative-pressure-reservoir pressure transducer, as well as an electronic controller including, in some embodiments, a user interface console (such as a touch-panel screen)—may be part of a base unit.

The positive-pressure reservoir provides to the actuation chamber the positive pressurization of a control gas to urge the membrane towards a position where the pumping chamber is at its minimum volume (i.e., the position where the membrane is against the rigid pumping-chamber wail). The negative-pressure reservoir provides to the actuation chamber the negative pressurization of the control gas to urge the membrane in the opposite direction, towards a position where the pumping chamber is at its maximum volume (i.e., the position where the membrane is against the rigid actuation-chamber wall).

A valving mechanism is used to control fluid communication between each of these reservoirs and the actuation chamber. As shown in FIG. 7, a separate valve is used for each of the reservoirs; a positive-supply valve controls fluid communication between the positive-pressure reservoir and the actuation chamber, and a negative-supply valve controls fluid communication between the negative-pressure reservoir and the actuation chamber. These two valves are controlled by the controller. Alternatively, a single three-way valve may be used in lieu of the two separate valves. The valves may be binary on-off valves or variable-restriction valves.

The controller also receives pressure information from the three pressure transducers: an actuation-chamber pressure transducer, a positive-pressure-reservoir pressure transducer, and a negative-pressure-reservoir pressure transducer. As their names suggest, these transducers respectively measure the pressure in the actuation chamber, the positive-pressure reservoir, and the negative-pressure reservoir. The actuation-chamber-pressure transducer is located in a base unit but is in fluid communication with the actuation chamber through the pod pump pneumatic port. The controller monitors the pressure in the two reservoirs to ensure they are properly pressurized (either positively or negatively). In one exemplary embodiment, the positive-pressure reservoir may be maintained at around 750 mmHg, while the negative-pressure reservoir may be maintained at around −450 mmHg.

Still referring to FIG. 7, a compressor-type pump or pumps (not shown) may be used to maintain the desired pressures in these reservoirs. For example, two independent compressors may be used to respectively service the reservoirs. Pressure in the reservoirs may be managed using a simple bang-bang control technique in which the compressor servicing the positive-pressure reservoir is turned on if the pressure in the reservoir falls below a predetermined threshold and the compressor servicing the negative-pressure reservoir is turned on if the pressure in the reservoir is above a predetermined threshold. The amount of hysteresis may be the same for both reservoirs or may be different. Tighter control of the pressure in the reservoirs can be achieved by reducing the size of the hysteresis band, although this will generally result in higher cycling frequencies of the compressors. If very tight control of the reservoir pressures is required or otherwise desirable for a particular application, the bang-bang technique could be replaced with a PID control technique and could use PWM signals on the compressors.

The pressure provided by the positive-pressure reservoir is preferably strong enough—under normal conditions—to urge the membrane all the way against the rigid pumping-chamber wall. Similarly, the negative pressure (i.e., the vacuum) provided by the negative-pressure reservoir is preferably strong enough—under normal conditions—to urge the membrane all the way against the actuation-chamber wall. In a further preferred embodiment, however, these positive and negative pressures provided by the reservoirs are within safe enough limits that even with either the positive-supply valve or the negative-supply valve open all the way, the positive or negative pressure applied against the membrane is not so strong as to damage the pod pump or create unsafe fluid pressures (e.g., that, may harm a patient receiving pumped blood or other fluid).

It will be appreciated that other types of actuation systems may be used to move the membrane back and forth instead of the two-reservoir pneumatic actuation system shown in FIG. 7, although a two-reservoir pneumatic actuation system is generally preferred. For example, alternative pneumatic actuation systems may include either a single positive-pressure reservoir or a single negative-pressure reservoir along with a single supply valve and a single tank pressure sensor, particularly in combination with a resilient membrane. Such pneumatic actuation systems may intermittently provide either a positive gas pressure or a negative gas pressure to the actuation chamber of the pod pump. In embodiments having a single positive-pressure reservoir, the pump may be operated by intermittently providing positive gas pressure to the actuation chamber, causing the membrane to move toward the pumping chamber wall and expel the contents of the pumping chamber, and releasing the gas pressure, causing the membrane to return to its relaxed position and draw fluid into the pumping chamber. In embodiments having a single negative-pressure reservoir, the pump may be operated by intermittently providing negative gas pressure to the actuation chamber, causing the membrane to move toward the actuation chamber wall and draw fluid into the pumping chamber, and releasing the gas pressure, causing the membrane, to return to its relaxed position and expel fluid from the pumping chamber.

3. Fluid Handling

As shown and described with respect to FIGS. 2A-2D, a fluid valve in the exemplary embodiment consists of a small chamber with a flexible membrane or membrane across the center dividing the chamber into a fluid half and a pneumatic half. The fluid valve, in the exemplary embodiment, has three entry/exit ports, two on the fluid half of the chamber and one the pneumatic half of the chamber. The port on the pneumatic half of the chamber can supply either positive pressure or vacuum (or rather than vacuum, in some embodiments, there is a vent to atmosphere) to the chamber. When a vacuum is applied to the pneumatic portion of the chamber, the membrane is pulled towards the pneumatic side of the chamber, clearing the fluid path and allowing fluid to flow into and out of the fluid side of the chamber. When positive pressure is applied to the pneumatic portion of the chamber, the membrane is pushed towards the fluid side of the chamber, blocking the fluid path and preventing fluid flow. In the volcano valve embodiment (as shown in FIGS. 2A-2B) on one of the fluid ports, that port seals off first when closing the valve and the remainder of any fluid in the valve is expelled through the port without the volcano feature. Additionally, in one embodiment of the valves, shown in FIG. 2D, the raised feature between the two ports allows for the membrane to seal the two ports from each other earlier in the actuation stroke (i.e., before the membrane seals the ports directly).

Referring again to FIG. 7, pressure valves are used to operate the pumps located at different points in the flow path. This architecture supports pressure control by using two variable-orifice valves and a pressure sensor at each pump chamber which requires pressure control. In one embodiment, one valve is connected to a high-pressure source and the other valve is connected to a low-pressure sink. A high-speed control loop monitors the pressure sensor and controls the valve positions to maintain the necessary pressure in the pump chamber.

Pressure sensors are used to monitor pressure in the pneumatic portion of the chambers themselves. By alternating between positive pressure and vacuum on the pneumatic side of the chamber, the membrane is cycled back and forth across the total chamber volume. With each cycle, fluid is drawn through the upstream valve of the inlet fluid port when the pneumatics pull a vacuum on the pods. The fluid is then subsequently expelled through the outlet port and the downstream valve when the pneumatics deliver positive pressure to the pods.

In many embodiments, pressure pumps consist of a pair of chambers. When the two chambers are run 180 degrees out of phase from one another the flow is essentially continuous.

4. Volume Measurement

These flow rates in the cassette are controlled using pressure pod pumps which can detect end-of-stroke. An outer control loop determines the correct pressure values to deliver the required flow. Pressure pumps can run an end of stroke algorithm to detect when each stroke completes. While the membrane is moving, the measured pressure in the chamber tracks a desired sinusoidal pressure. When the membrane contacts a chamber wall, the pressure becomes constant, no longer tracking the sinusoid. This change in the pressure signal is used to detect when the stroke has ended, i.e., the end-of-stroke.

The pressure pumps have a known volume. Thus, an end of stroke indicates a known volume of fluid is in the chamber. Thus, using the end-of-stroke, fluid flow may be controlled using rate equating to volume.

As described above in more detail, FMS may be used to determine the volume of fluid pumped by the metering pumps. In some embodiments, the metering pump may pump fluid without using the FMS volume measurement system, however, in the exemplary embodiments, the FMS volume measurement system is used to calculate the exact volume of fluid pumped.

5. Exemplary Embodiment, of the Pumping Cassette:

The terms inlet and outlet as well as fluid paths are used for description purposes only. In other embodiments, an inlet can be an outlet. The denotations simply refer to separate entrance areas into the cassette.

The designations give for the fluid inlets (which can also be fluid outlets), for example, first fluid outlet, second fluid outlet, merely indicate that a fluid may travel out of or into the cassette via that inlet/outlet. In some cases, more than one inlet/outlet on the schematic is designated with an identical name. This merely describes that all of the inlet/outlets having that designation are pumped by the same metering pump or set of pod pumps (which in alternate embodiments, can be a single pod pump).

Figure 8:
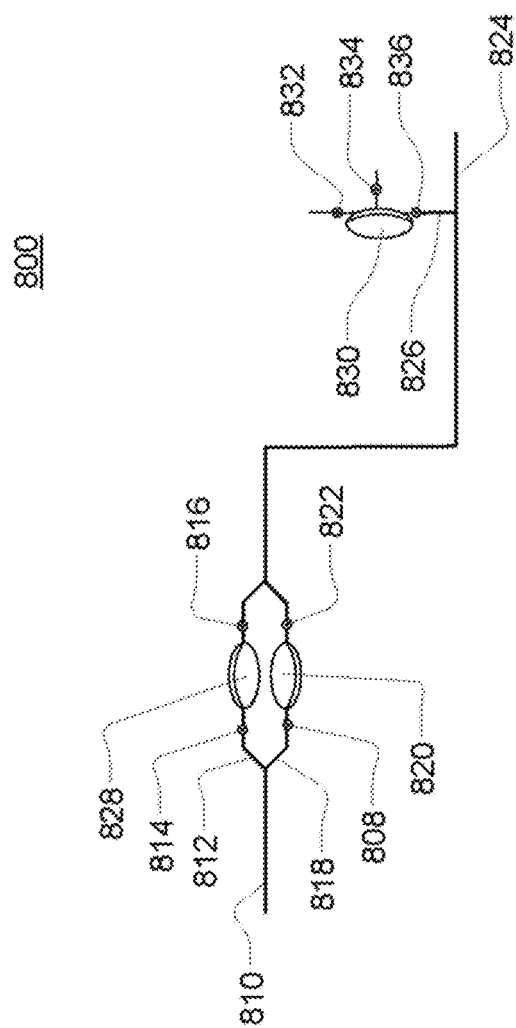
FIG. 8 is one embodiment of the fluid flow-path schematic of the cassette.

Referring now to FIG. 8, an exemplary embodiment of the fluid schematic of the pumping cassette 800 is shown. Other schematics are readily discernable. The cassette 800 includes at least one pod pump 820, 828 and at least one metering pump 830. The cassette 800 also includes a fluid inlet one 810, where fluid enters the cassette from a source. The fluid includes a flow rate provided by the at least one pod pump 820, 828. The cassette 800 also includes a fluid outlet one 824 where the fluid exits the cassette 800 having a flow rate provided by one of the at least one pod pump 820, 828.

The exemplary embodiment includes two pod pumps 820, 828, however, in alternate embodiments, one or more pod pumps are included in the cassette. In the exemplary embodiment, two pod pumps provide for steady flow. The metering pump 830 pumps a volume of second fluid from a second fluid source into the fluid line prior to the fluid exiting fluid outlet one 824.

The fluid schematic of the cassette 800 shown in FIG. 8 may be embodied into various cassette apparatus. Thus, the various embodiments of the cassette 800 that include a fluid flow-path represented by the fluid schematic shown in FIG. 8 are not the only cassette embodiments that may incorporate this or an alternate embodiment of this fluid schematic. Additionally, the types of valves, the order of actuation of the valves, and the number of pumps may vary in various cassette embodiments of this fluid schematic.

Still referring to FIG. 8, the fluid enters the cassette through fluid inlet one 810 and is pumped to either a first pump fluid path 812 or a second pump fluid path 818. In one embodiment, pump inlet valves 814, 808 alternately open and close, and the valve 814, 808 that is open at any given time allows the fluid into its respective fluid path 812, 818 and into the respective pod pump 828, 820. The respective pump inlet valve 814, 808 then closes, and the corresponding pump outlet valve 816, 822 opens. The fluid is pumped out of the pod pump and though fluid outlet one 824. However, in other embodiments, both valves 808, 814 open and close at the same time. In some embodiments, no valves are in the cassette.

A metering pump 830 pumps a volume of second fluid from a source connected to the cassette 800. The metering pump 830 is actuated separately from the pod pumps 820, 828, thus, the metering pump 830 can pump at different rates than the pod pumps 820, 828. The metering pump 830 pumps a volume of second fluid from a second fluid source into the fluid line at point 826, prior to the fluid exiting fluid outlet one 824 The source is connected to the metering pump through a fluid line which intersects the main fluid path at point 826. Valves 832, 836 work to pump fluid from the second source and into the fluid line at point 826.

In some embodiments, the metering pump 830 is either not used or has a very different pumping pattern from the pod pumps 820, 828. In the exemplary embodiment, the metering pump includes fluid management system (FMS) volumetric measurement capacity. The reference chamber is located outside the cassette. In the exemplary embodiment, the second fluid source is a vial of liquid connected directly to a spike in the cassette. The spike is directly connected to the fluid line. In other embodiments, the spike is connected to a tube that is connected to the second fluid source. The vial can contain any liquid, but in some embodiments, contains a therapeutic liquid such as heparin. However, in other embodiments, the second fluid is a chemotherapy agent, a nutritional supplement, antibiotic or any other therapeutic whether nutritional or non-nutritive liquid.

The fluid is pumped into the fluid inlet one 810 and to the fluid outlet, one 824. In some embodiments, the fluid is pumped from a source to a treatment area, which is part of a continuous flow circuit, and then flows back to the source. In one embodiment, the cassette is used to pump blood from a patient, through the fluid outlet one 824 which is connected to a dialyzer. The blood then flows through the dialyzer and back to the patient through a tube, The embodiments of the fluid flow-path schematic shown in FIG. 8 can be embodied into a structure. In the exemplary embodiment, the structure is a three plate cassette with actuating membranes. Alternate embodiments of the cassette are also described below.

Figure 9A:
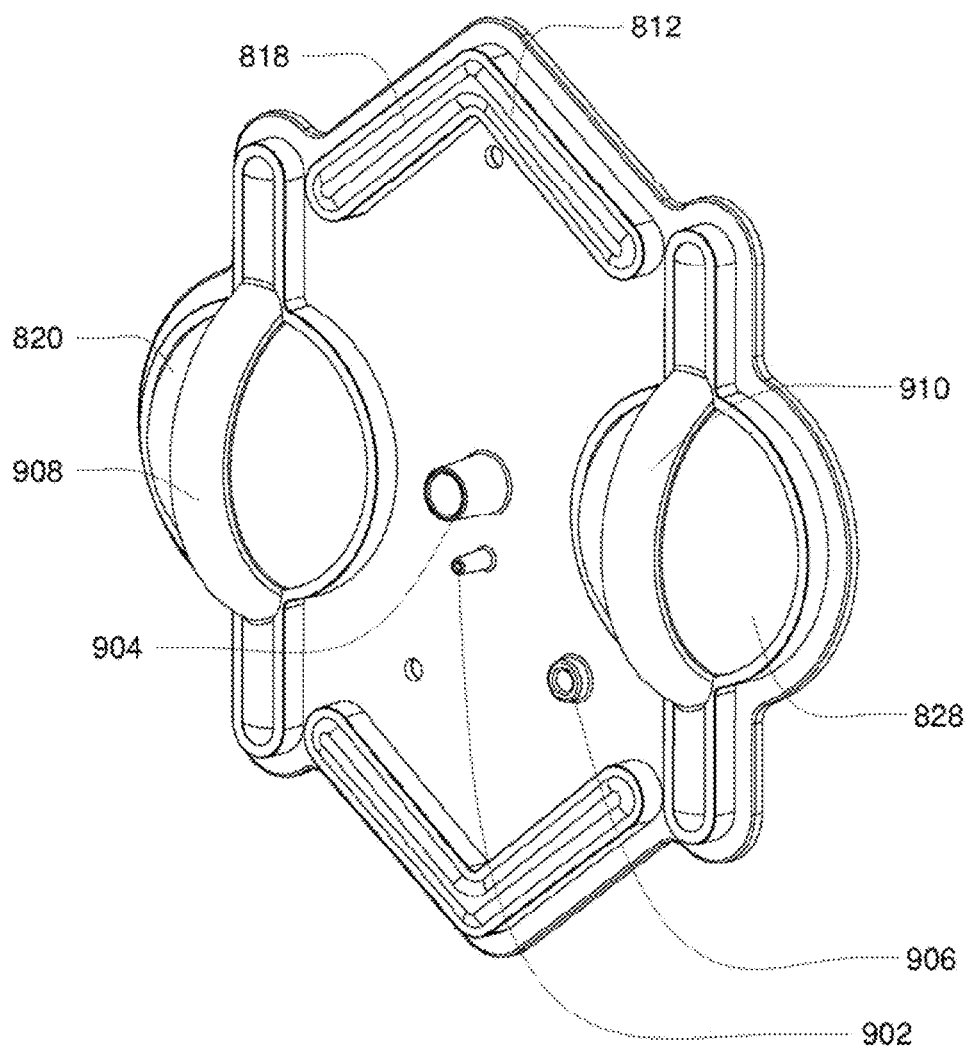
FIGS. 9A and 9B are isometric and top views of the outer top plate of the exemplary embodiment of the cassette.
Figure 9B:
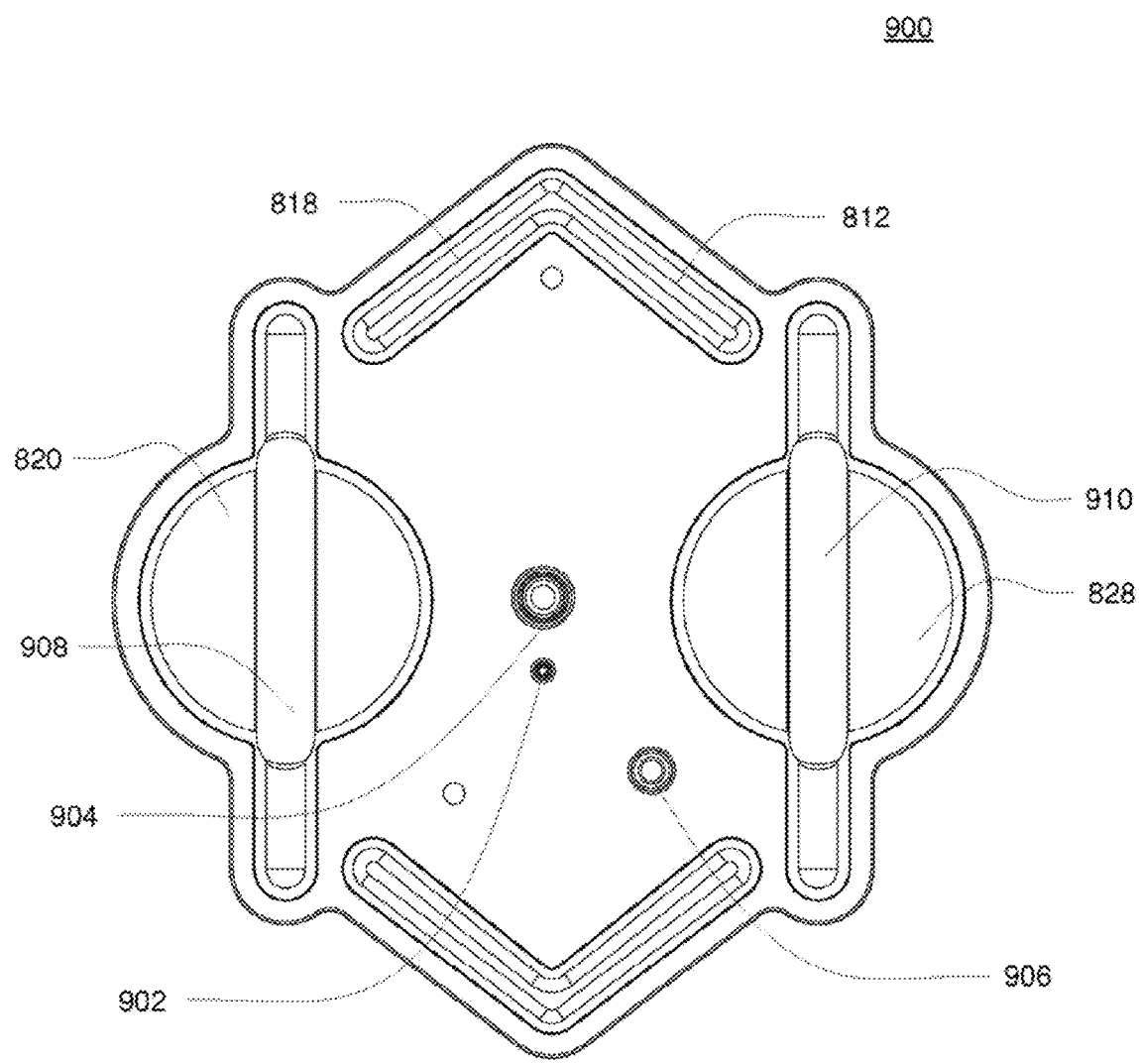

Referring now to FIGS. 9A and 9B, the outer side of the top plate 900 of the exemplary embodiment of the cassette is shown. The top plate 900 includes one half of the pod pumps 820, 828. This half is the liquid half where the source fluid will flow through. The two fluid paths 818, 812 are shown. These fluid paths lead to their respective pod pumps 820, 828.

The pod pumps 820, 828 include a raised flow path 908, 910. The raised flow path 908, 910 allows for the fluid to continue to flow through the pod pumps 820, 828 after the membrane (not shown) reaches the end of stroke. Thus, the raised flow path 908, 910 minimizes the membrane causing air or fluid to be trapped in the pod pump 820, 828 or the membrane blocking the inlet or outlet of the pod pump 820, 828, which would inhibit continuous flow. The raised flow path 908, 910 is shown in the exemplary embodiment having particular dimensions, and in the exemplary embodiment, the dimensions are equivalent to the fluid flow paths 818, 812. However, in alternate embodiments, as seen in FIGS. 18A-18E, the raised flow path 908, 910 is narrower, or in still other embodiments, the raised flow path 908, 910 can be any dimensions as the purpose is to control fluid flow so as to achieve a desired flow rate or behavior of the fluid. In some embodiments, the raised flow path 908, 910 and the fluid flow paths 818, 812 have different dimensions. Thus, the dimensions shown and described here with respect to the raised flow path, the pod pumps, the valves or any other aspect are mere exemplary and alternate embodiments. Other embodiments are readily apparent.

In the exemplary embodiment of the cassette, the top plate includes a spike 902 as well as a container perch 904. The spike 902 is hollow and is fluidly connected to the flow path. In some embodiments, a needle is attached into the spike. In other embodiments, a needle is connected to the container attachment (see FIG. 12C, 1206).

Figure 9C:
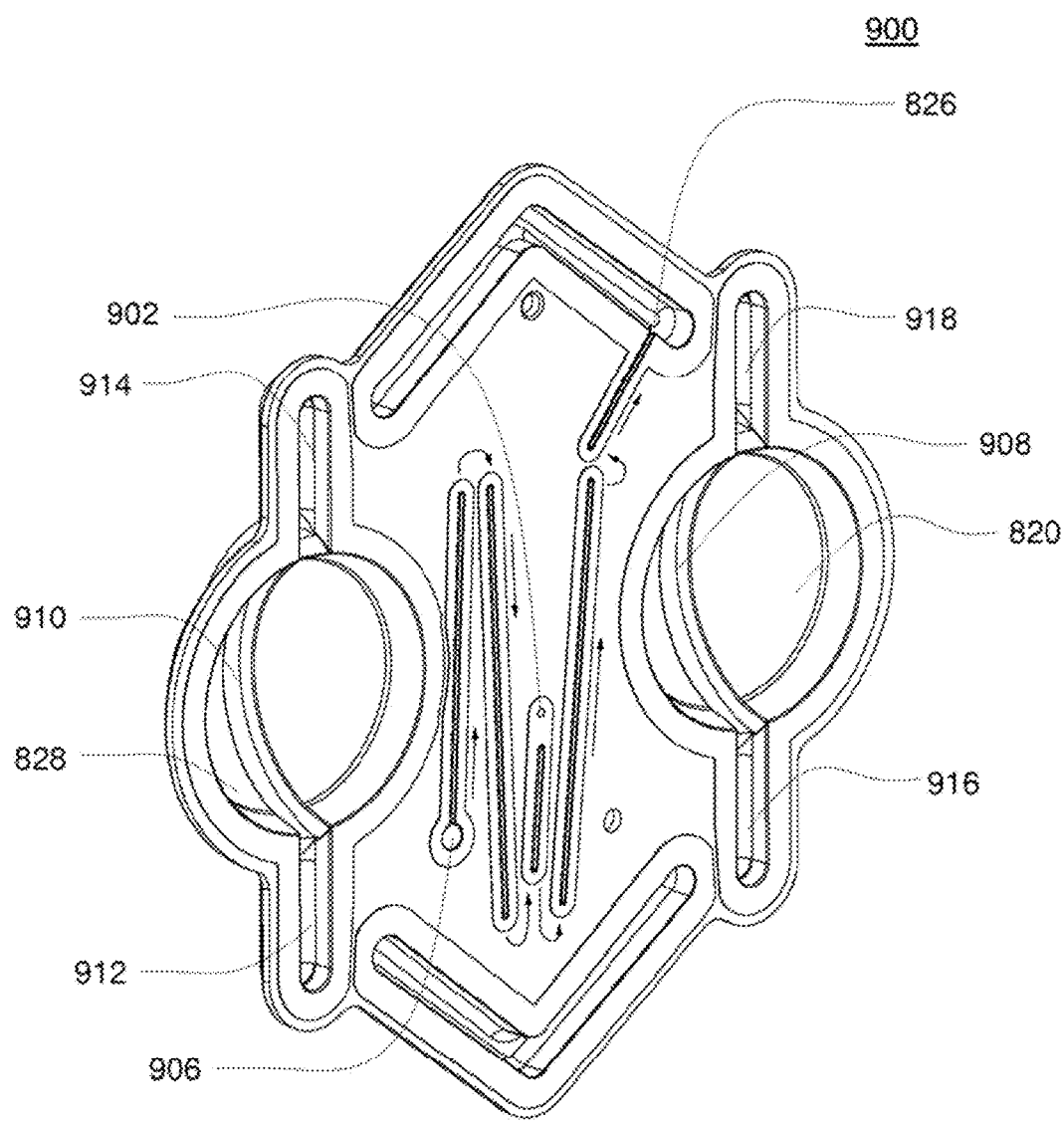
FIGS. 9C and 9D are isometric and top views of the inner top plate of the exemplary embodiment of the cassette.
Figure 9D:
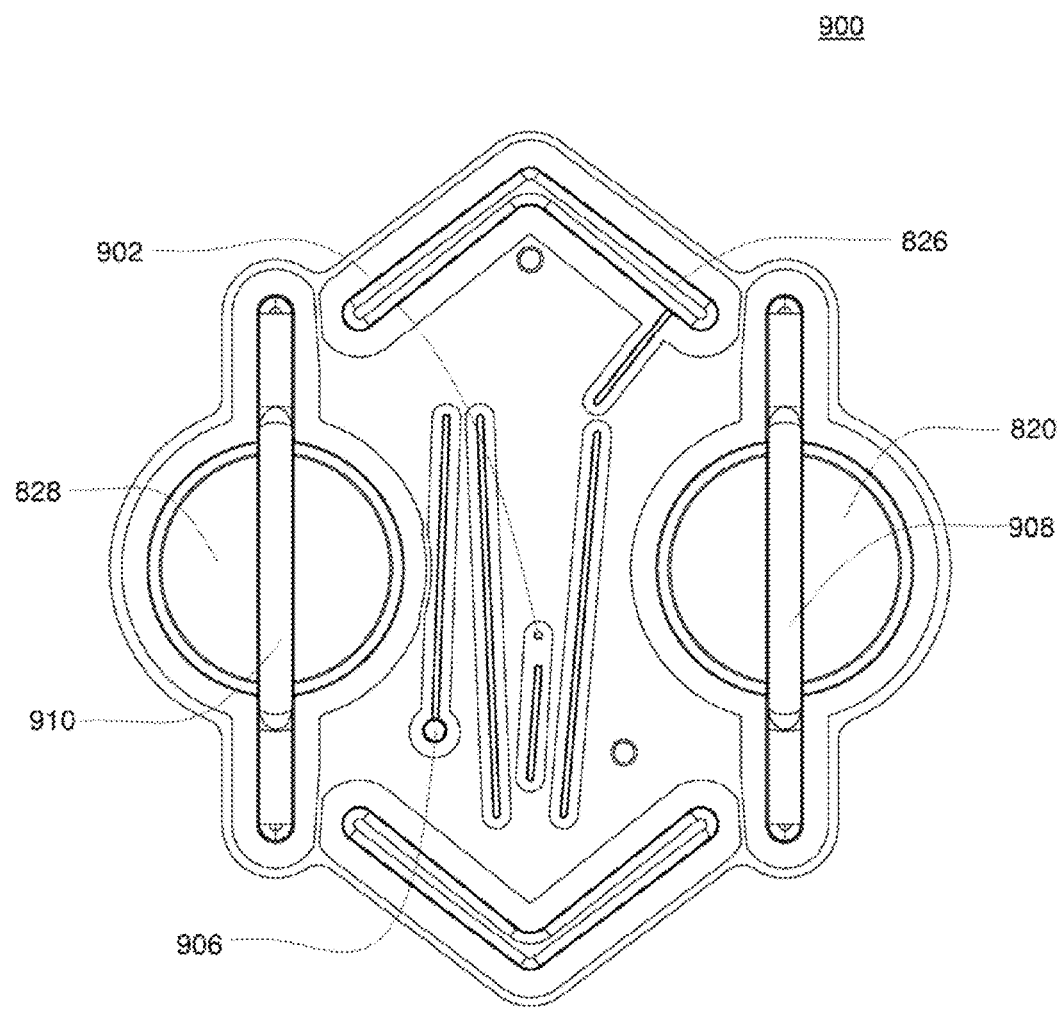
Figure 9E:
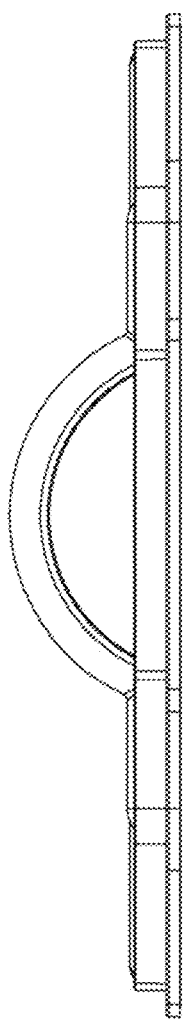
FIG. 9E is a side view of the top plate of the exemplary embodiment of the cassette.

Referring now to FIGS. 9C and 9D, the inside of the top plate 900 is shown. The raised flow paths 908, 910 connects to the inlet flow paths 912, 916 and outlet flow paths 914, 918 of the pod pumps 820, 828. The raised flow paths are described in more detail above.

The metering pump (not shown, shown in FIGS. 10C and 10D) includes connection to an air vent 906 as well as connection to the spike's hollow path 902. In the exemplary embodiment, the air vent 906 includes an air filter (not shown). In the exemplary embodiment, the air filter is a particle air filter. In the exemplary embodiment, the filter is a somicron hydrophobic air filter. In various embodiments, the size of the filter may vary, in some instances the size will depend on desired outcome. The metering pump works by taking air in through the air vent 906, pumping the air to the container of second fluid (not shown) through the spike's hollow path 902 and then pumping a volume of second fluid out of the container (not shown) through the spike's hollow path 902 and into the fluid line at point 826. This fluid flow path for the metering pump is shown with arrows on FIG. 9C.

Figure 10A:
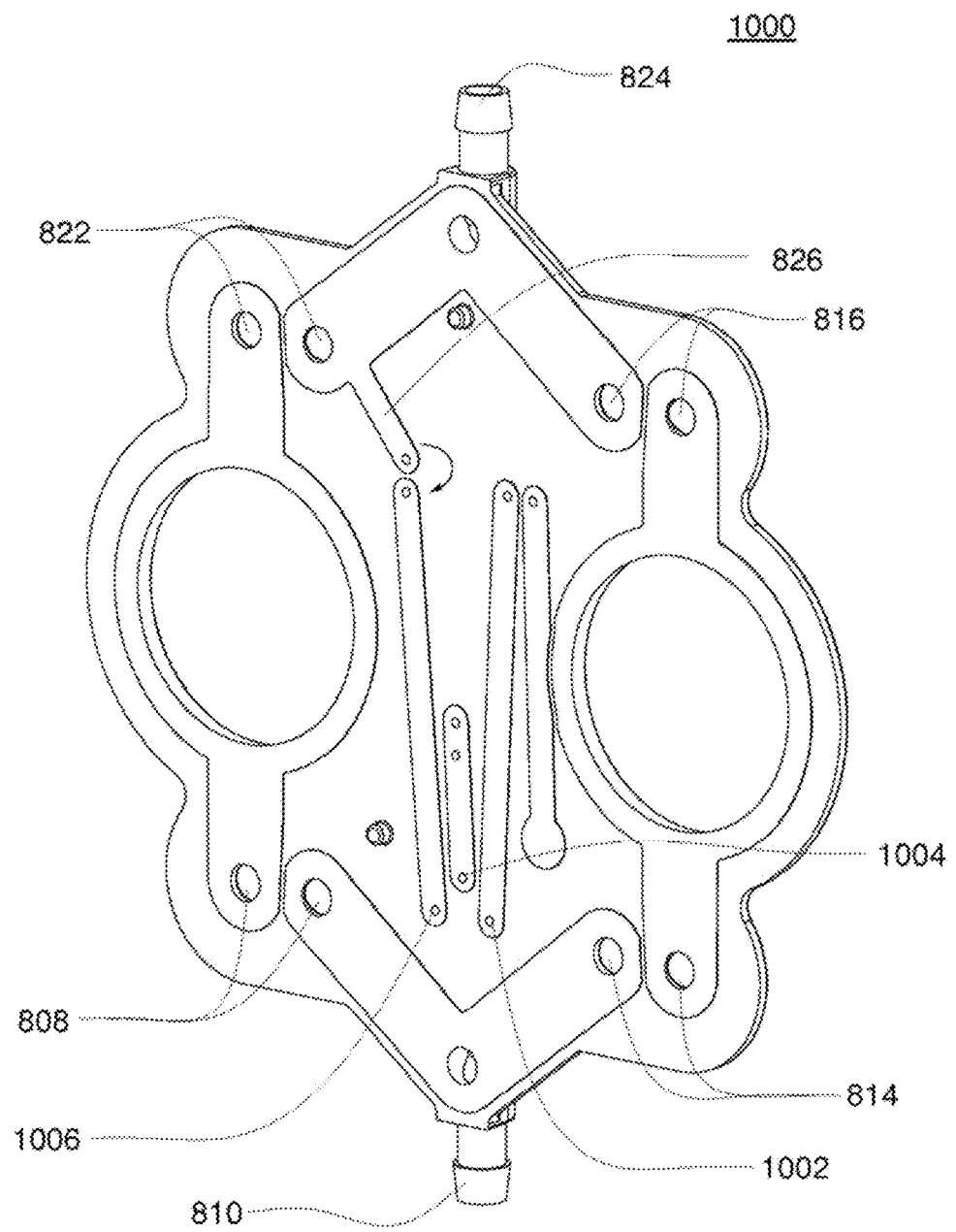
FIGS. 10A and 10B are isometric and top views of the liquid side of the midplate according to the exemplary embodiment of the cassette.
Figure 10B:
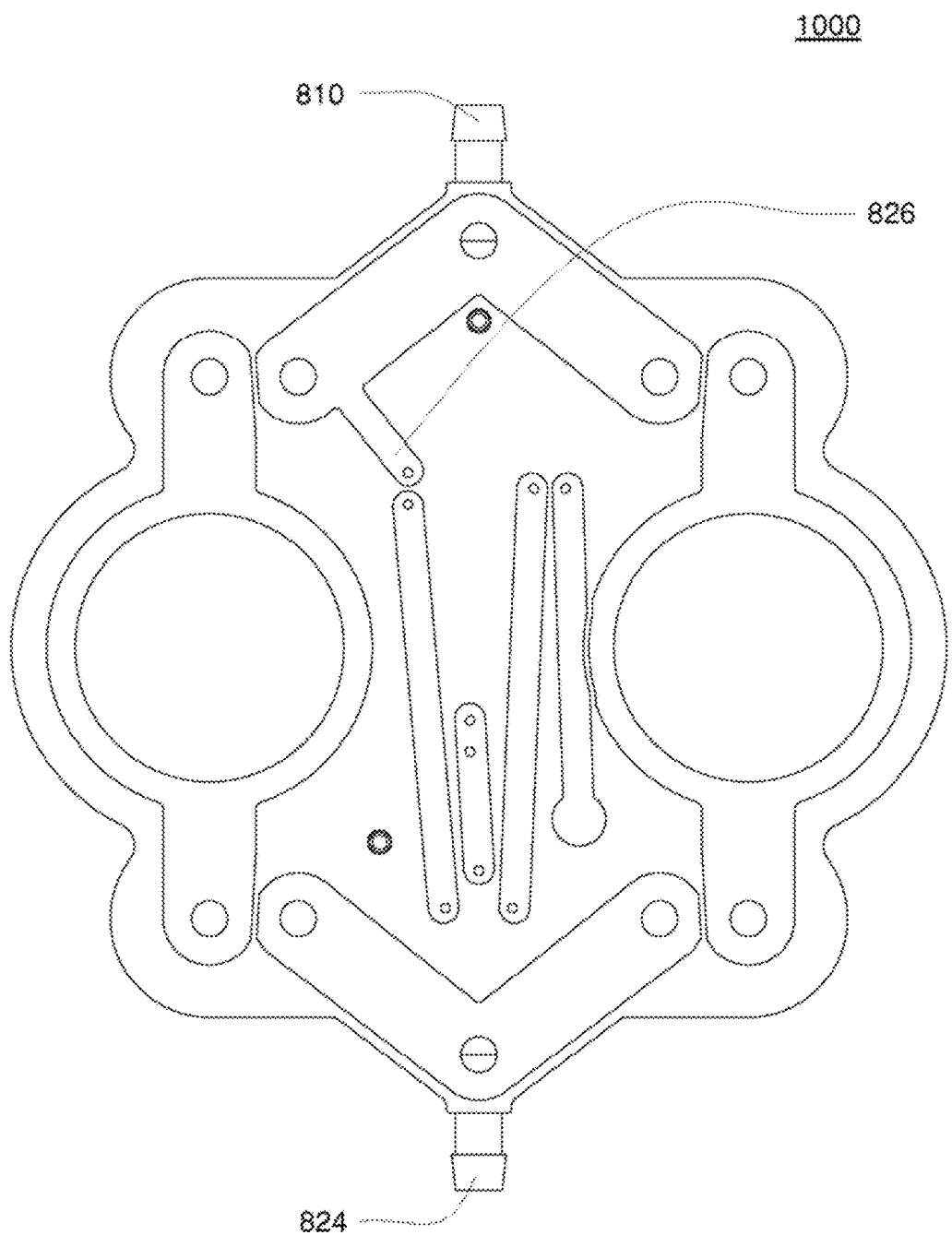
Figure 10C:
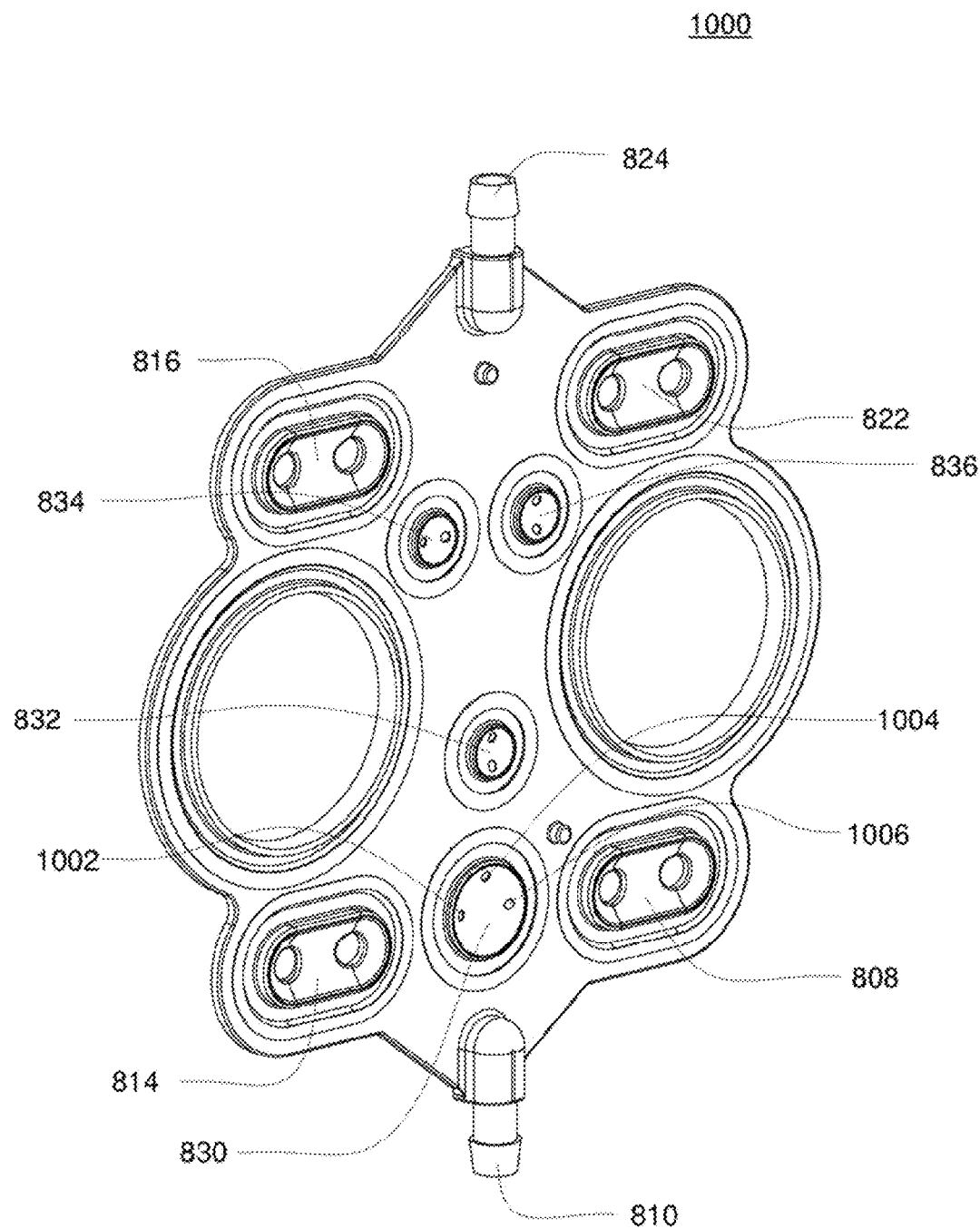
FIGS. 10C and 10D are isometric and top views of the air side of the midplate according to the exemplary embodiment of the cassette.
Figure 10D:
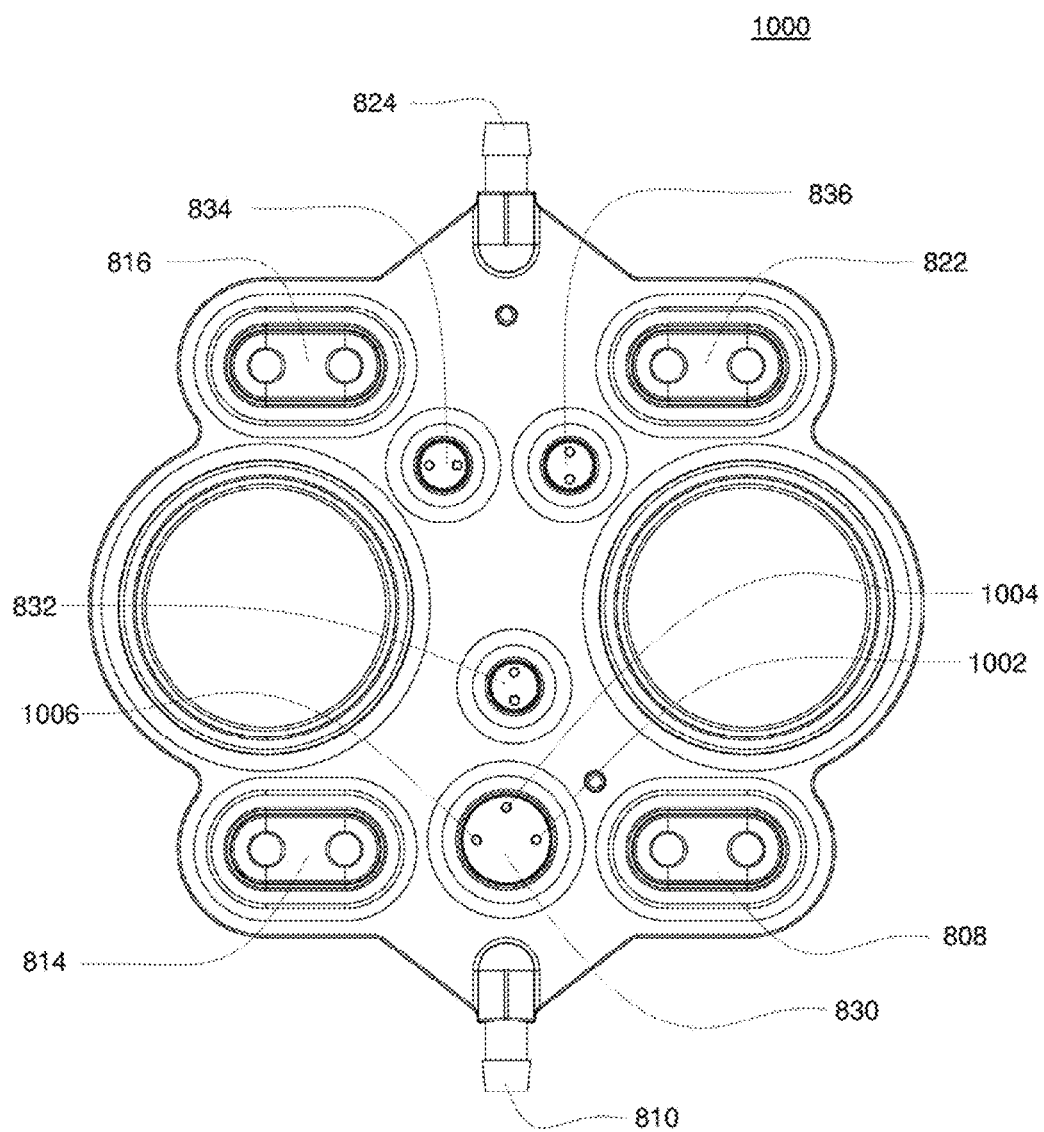

Referring now to FIGS. 10A and 10D, the liquid side of the midplate 1000 is shown. The areas complementary to the fluid paths on the inner top plate are shown. These areas are slightly raised tracks that present a surface finish that is conducive to laser welding, which is the mode of manufacture in the exemplary embodiment. The fluid inlet 810 and fluid outlet 824 are also shown in this view.

Referring next to FIGS. 10C and 10D, the air side of the midplate 1000 is shown according to the exemplary embodiment. The air side of the valve holes 808, 814, 816, 822 correspond to the holes in the fluid side of the midplate (shown in FIG. 10A). As seen in FIGS. 12C and 12D, membranes 1220 complete valves 808, 814, 816, 822 while membranes 1226 complete pod pumps 820, 828. One embodiment of the valve membrane is shown in FIG. 2E. Additional embodiments of the valve membrane are shown in FIGS. 2F-2G. The metering pump 830 is completed by membrane 1224. One embodiment of the metering pump membrane is shown in FIG. 5F. Other embodiments of the metering pump membrane are shown in FIGS. 5E-5H. The valves 808, 814, 816, 822, 832, 834, 836 are actuated pneumatically, and as the membrane is pulled away from the holes, liquid is drawn in, as the membrane is pushed toward the holes. The fluid flow is directed by the opening and closing of the valves 808, 814, 816, 822, 832, 834, 836.

Referring to FIGS. 10A and 10C, the metering pump includes three holes, 1002, 1004, 1006 One hole 1002 pulls air into the metering pump, the second hole 1004 pushes air to the spike/source container and also, draws liquid from the source container, and the third hole 1006 pushes the second fluid from the metering pump 830 to the fluid line to point 826.

Valves 832, 834, 836 actuate the second fluid metering pump. Valve 832 is the second fluid/spike valve, valve 834 is the air valve and valve 836 is the valve that controls the flow of fluid to the fluid line to area 826.

Figure 11A:
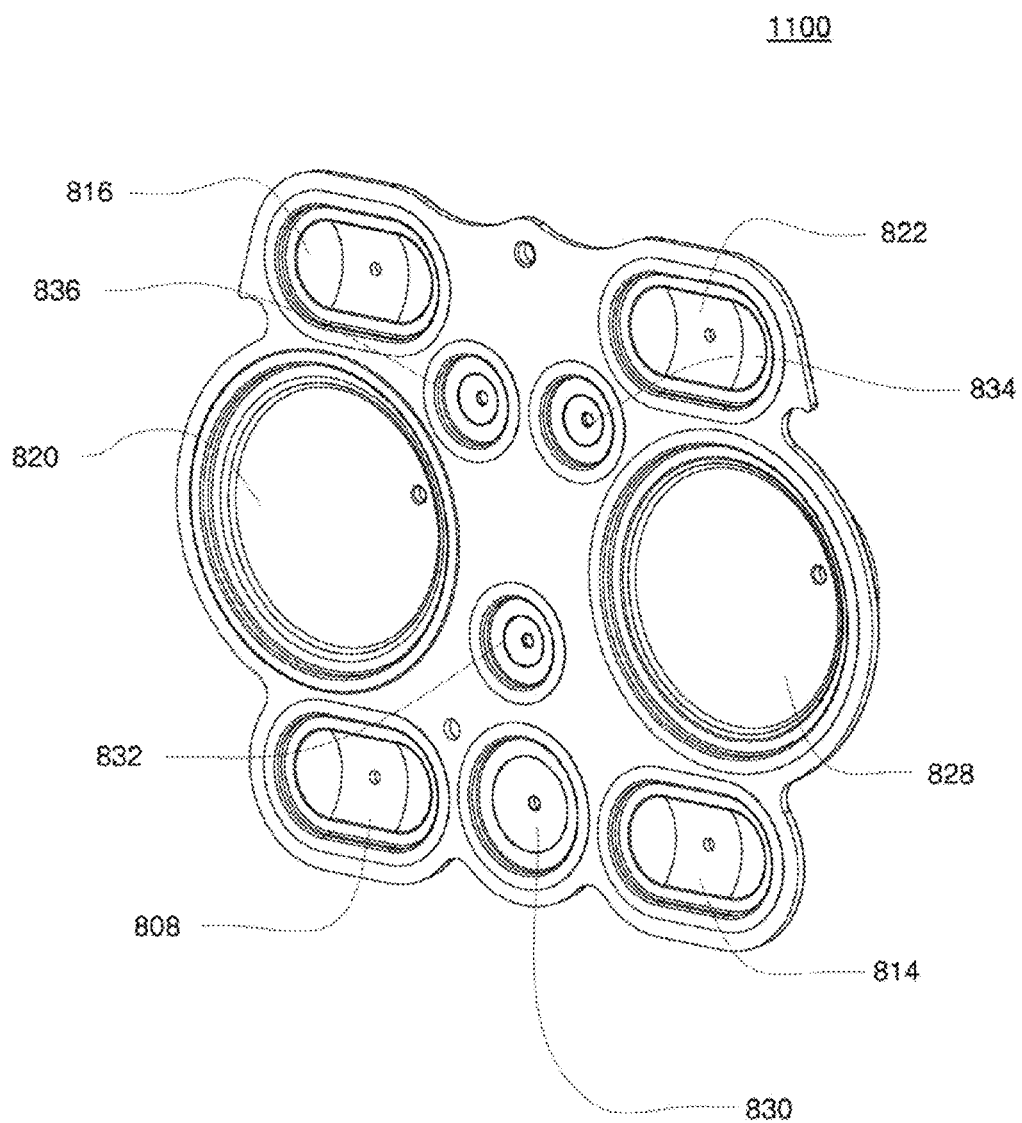
FIGS. 11A and 11B are isometric and top views of the inner side of the bottom plate according to the exemplary embodiment of the cassette.
Figure 11B:
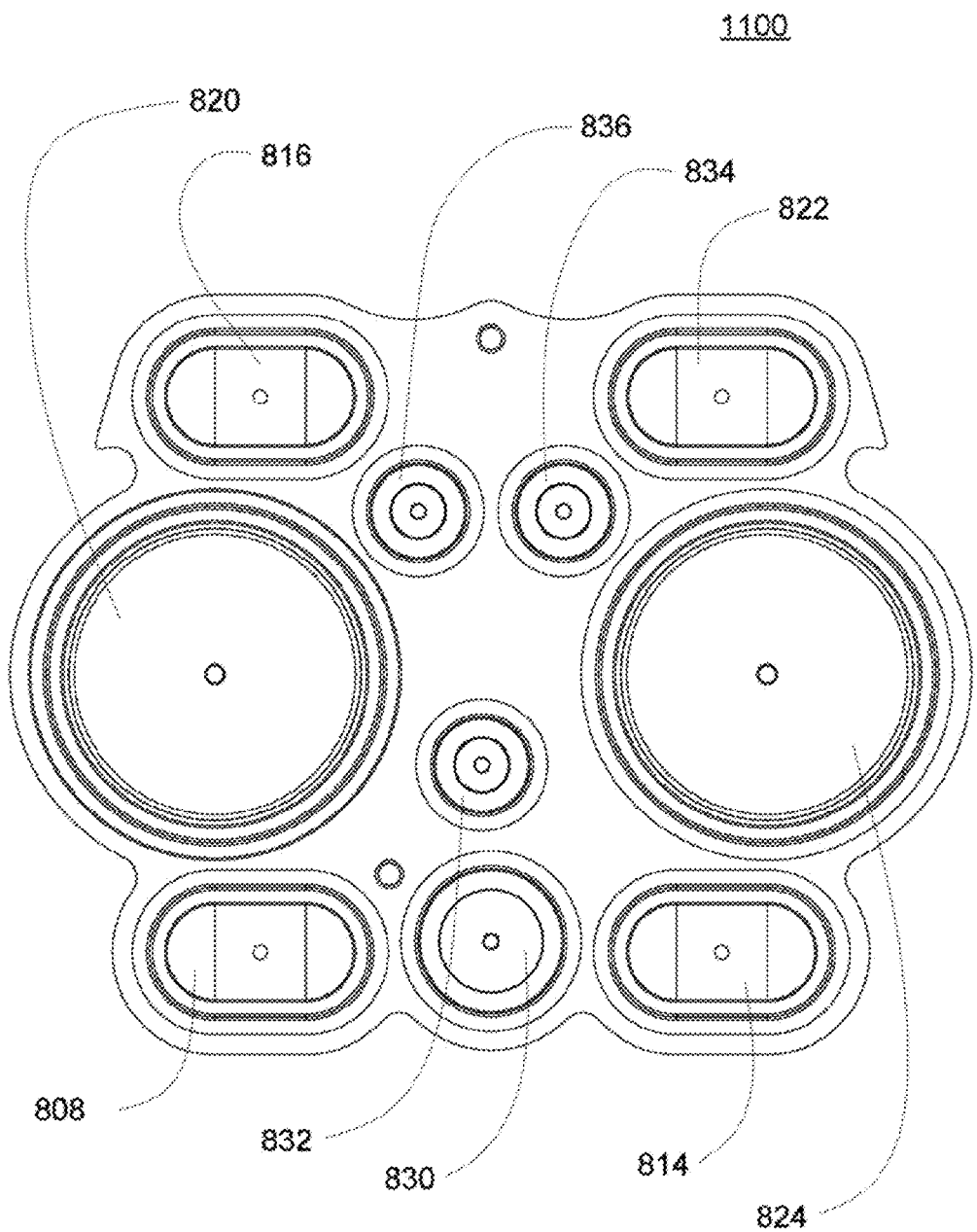
Figure 11C:
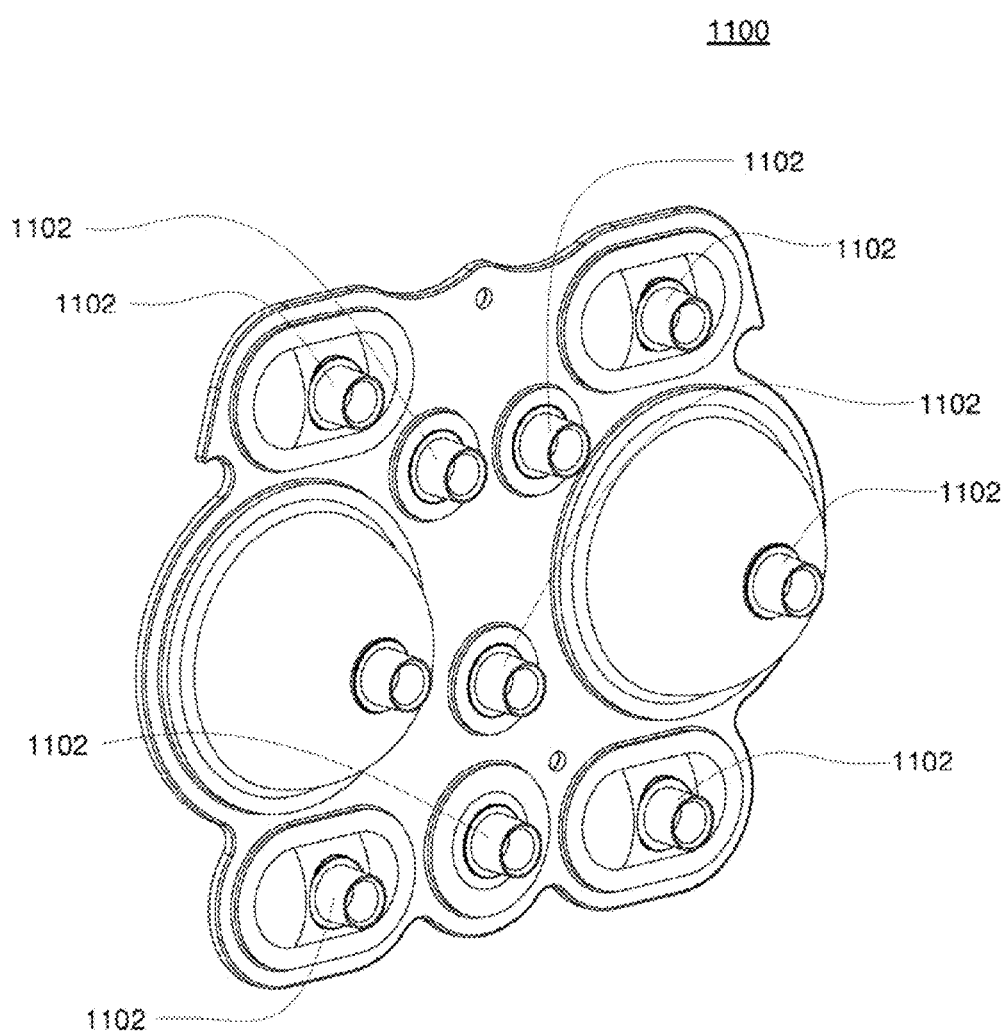
FIGS. 11C and 11D are isometric and top views of the outer side of the bottom plate according to the exemplary embodiment of the cassette.
Figure 11D:
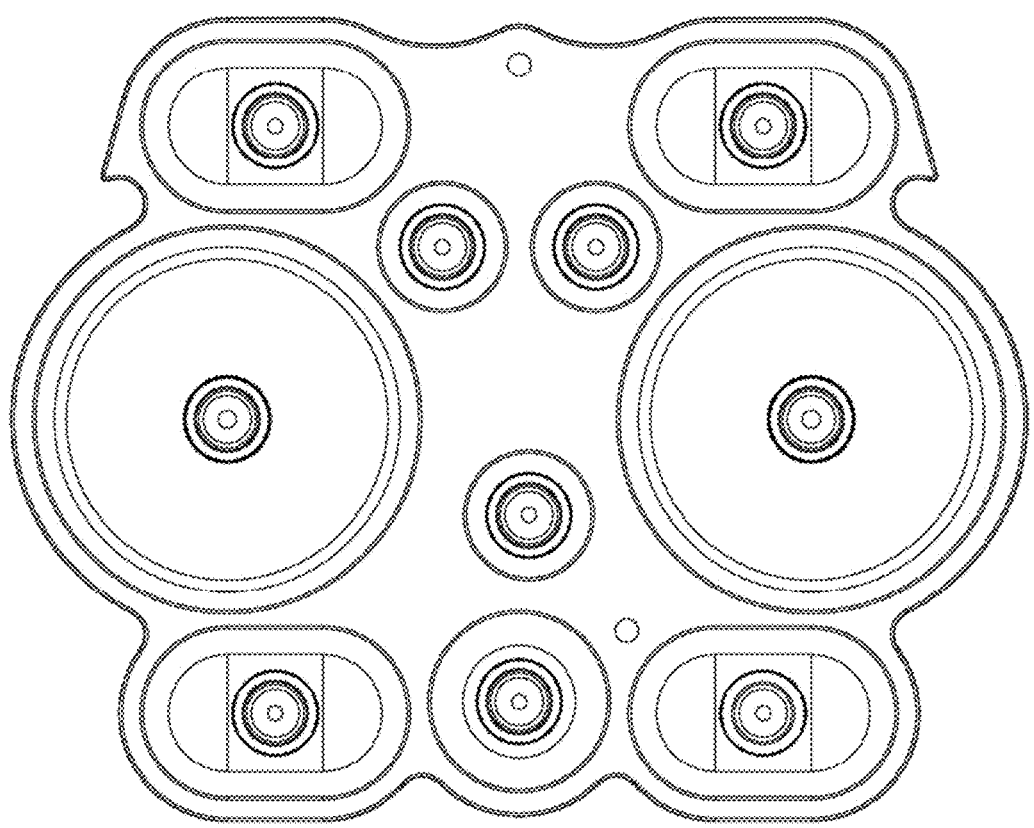
Figure 11E:
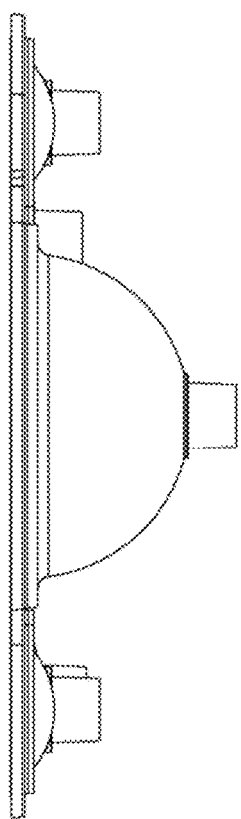
FIG. 11E is a side view of the bottom plate according to the exemplary embodiment of the cassette.

Referring next to FIGS. 11A and 11B, the inner view of the bottom plate 1100 is shown. The inside view of the pod pumps 820, 828, the metering pump 830 and the valves 808, 814, 816, 822, 832, 834, 836 actuation/air chamber is shown. The pod pumps 820, 828, metering pump 830 and the valves 808, 814, 816, 822, 832, 834, 836 are actuated by a pneumatic air source. Referring now to FIGS. 11C and 11D, the outer side of the bottom plate 1100 is shown. The source of air is attached to this side of the cassette. In one embodiment, tubes connect to the features on the valves and pumps 1102. In some embodiments, the valves are ganged, and more than one valve is actuated by the same air line.

Figure 12A:
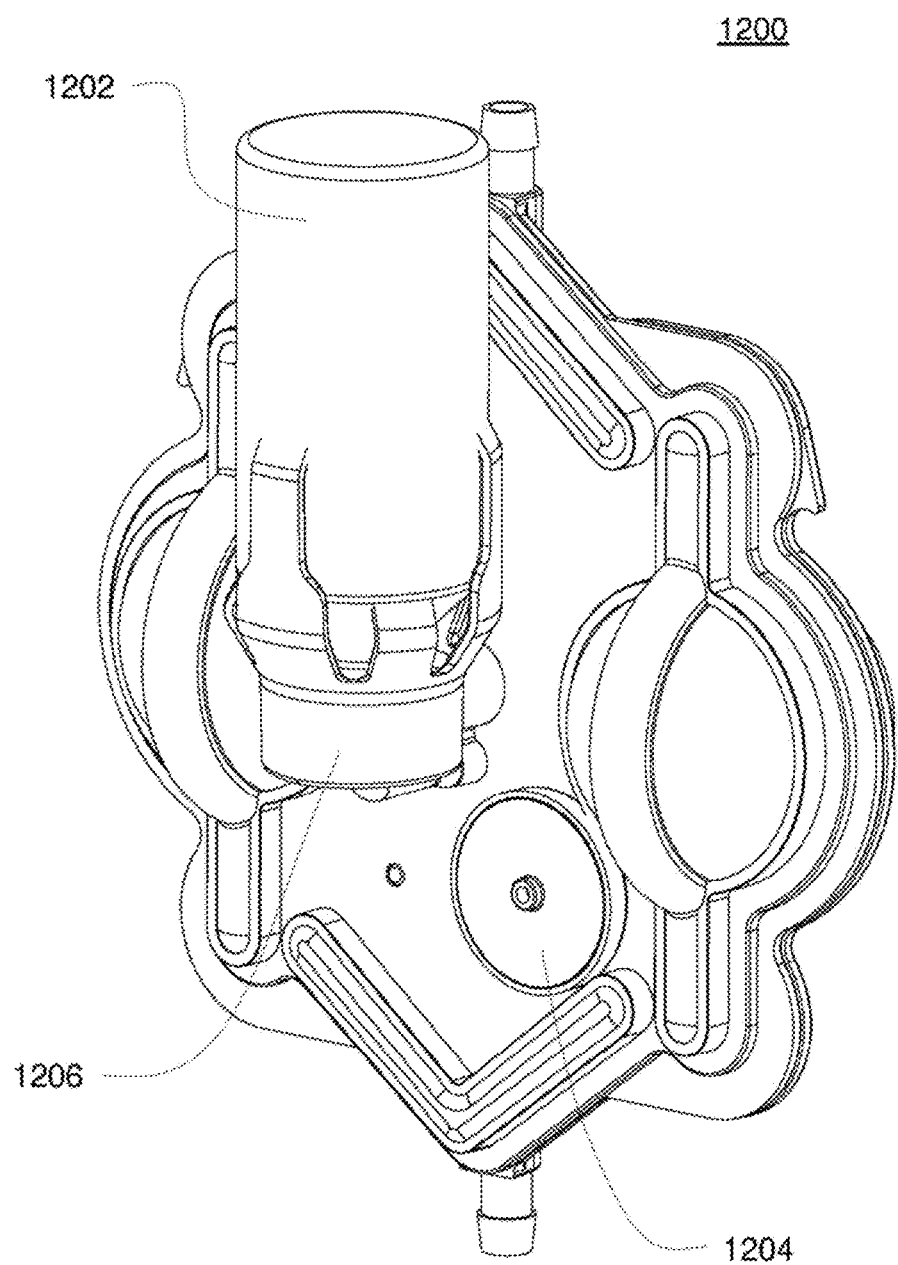
FIG. 12A is a top view of the assembled exemplary embodiment of the cassette with a vial attached.
Figure 12B:
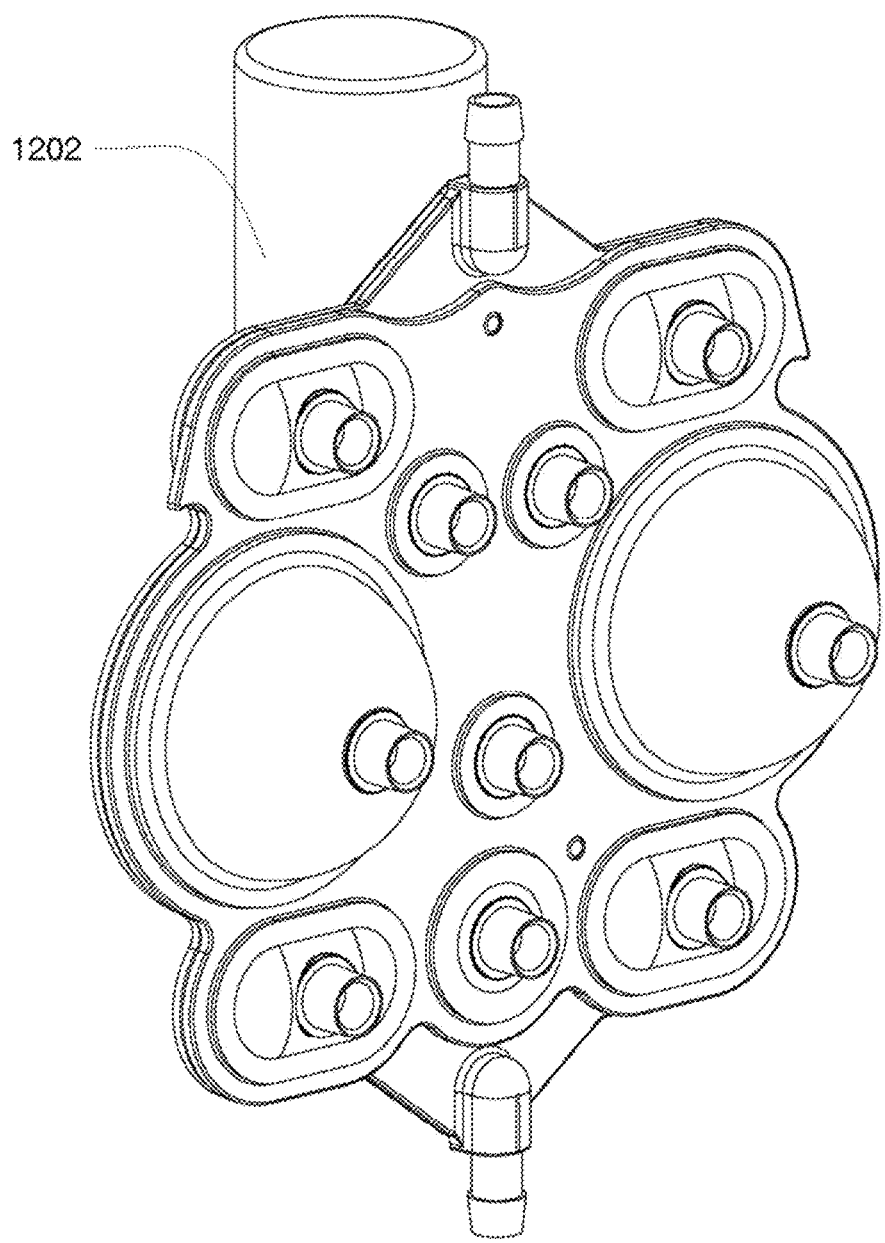
FIG. 12B is a bottom view of the assembled exemplary embodiment of the cassette with a vial attached.
Figure 12C:
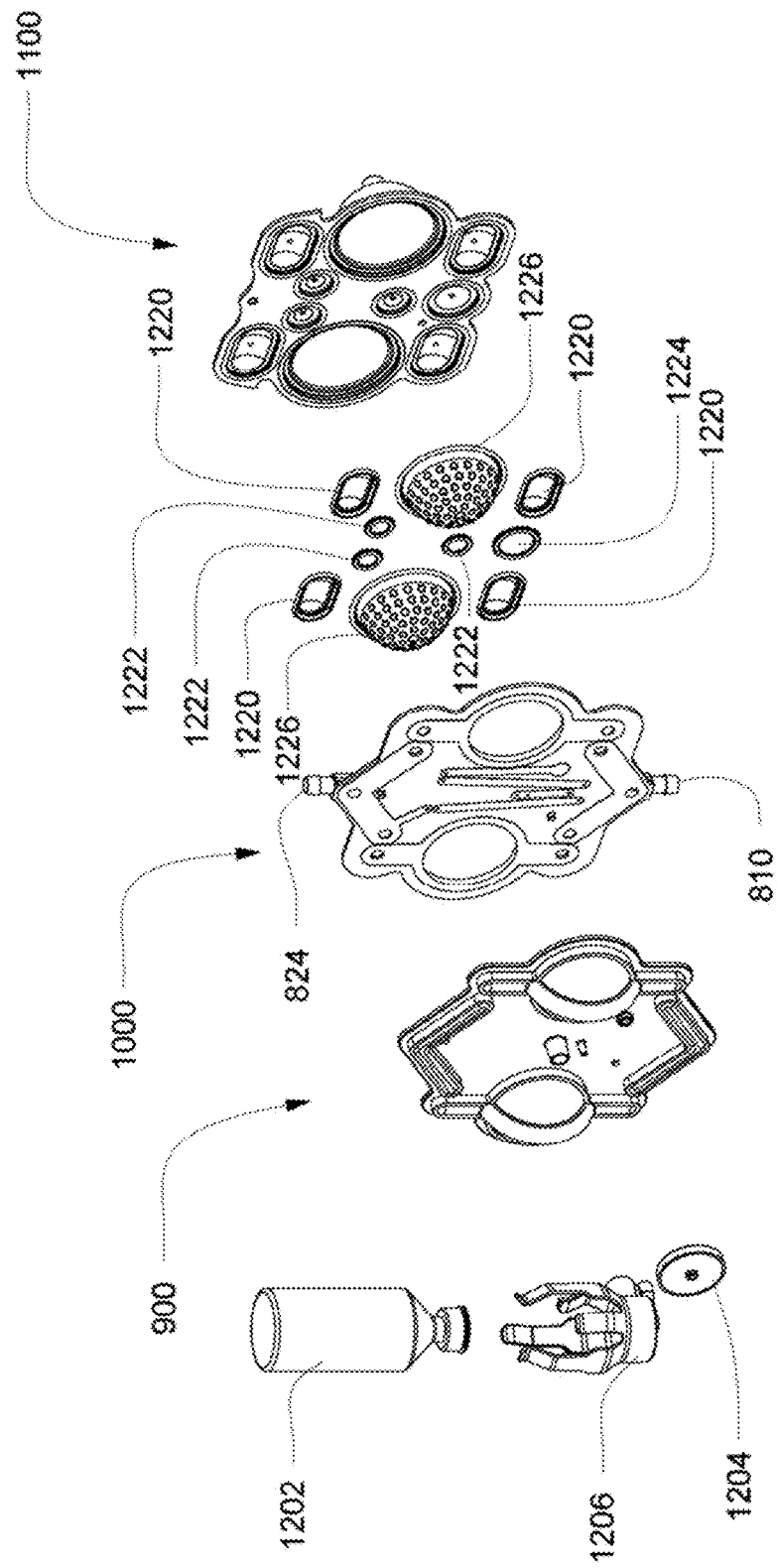
FIG. 12C is an exploded view of the assembled exemplary embodiment of the cassette with a vial.

Referring now to FIGS. 12A and 12B, an assembled cassette 1200 with a container/source of second fluid 1202 attached is shown. The container 1202 contains the source of the second fluid and is attached to the spike (not shown) by a container attachment 1206. The air filter 1204 is shown attached to the air vent (not shown, shown in FIG. 9A as 906). Although not visible in FIG. 12A, the container perch (shown in FIG. 9A as 904) is under the container attachment 1206. An exploded view of the assembled cassette 1200 shown in FIGS. 12A and 12B is shown in FIGS. 12C and 12D. In these views, the exemplary embodiment of the pod pump membranes 1226 is shown. The exemplary embodiment includes membranes shown in FIGS. 4E and 4F. The gasket of the membrane provides a seal between the liquid chamber (in the top plate 900) and the air/actuation chamber (in the bottom plate 1100). The dimpled texture on the dome of the membranes 1226 provide, amongst other features, additional space for air and liquid to escape the chamber at the end of stroke. In other embodiments of the cassette, the membranes shown in FIG. 5A, 5C or 5D may be used. In alternate embodiments of the cassette, the membranes shown in FIGS. 6A-6G may be used. As discussed in greater detail above, these membranes include a double gasket 62, 64. The double gasket 62, 64 feature would be preferred in embodiments where both sides of the pod pump include liquid or in applications where sealing both chambers is desired. In these embodiments, a rim complementary to the gasket or other feature (not shown) would be added to the inner bottom plate 1100 for the gasket 62 to seal the pod pump chamber in the bottom plate 1100.

Figure 13A:
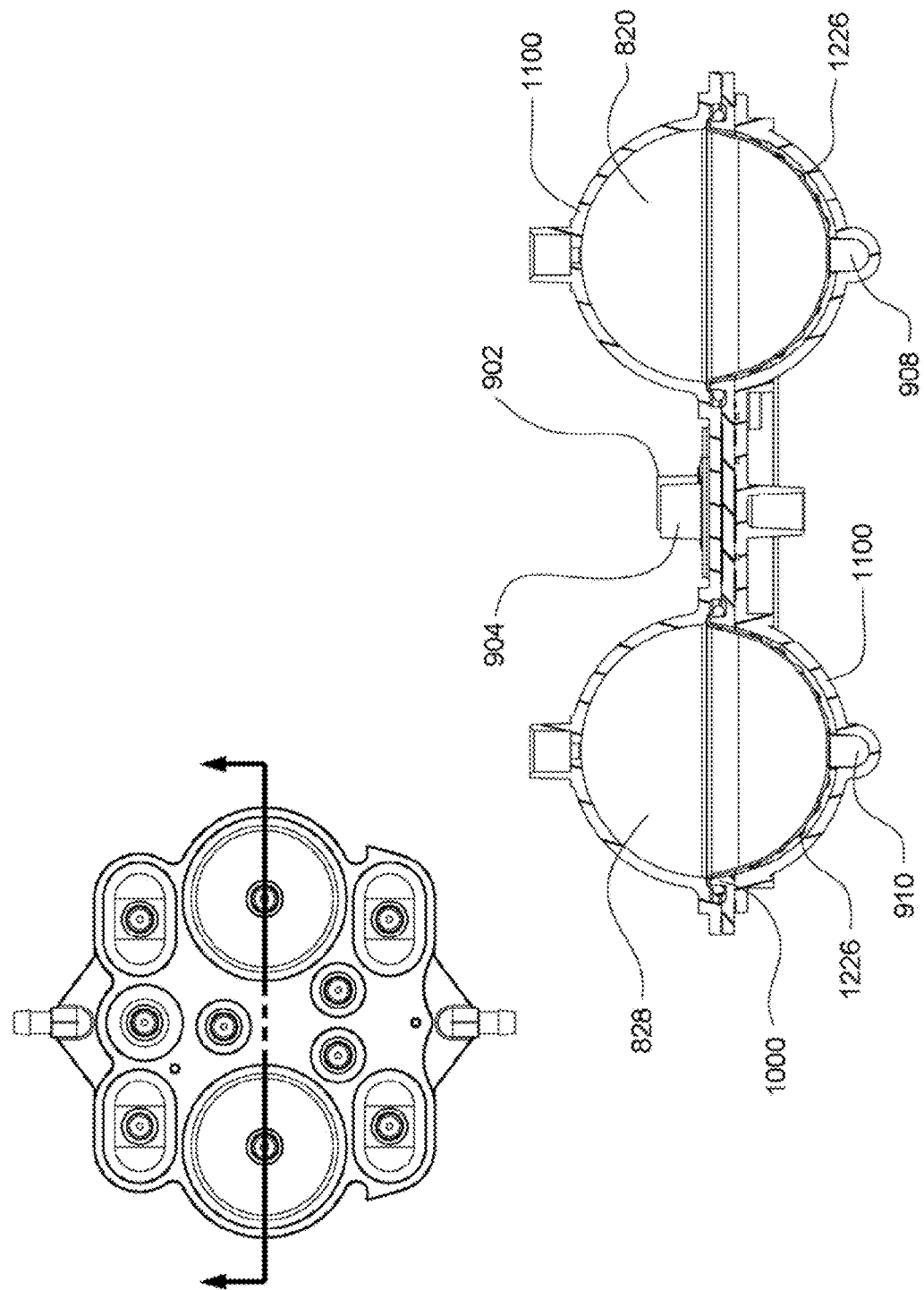
FIGS. 13A-13C show cross sectional views of the exemplary embodiment of the assembled cassette.

Referring now to FIG. 13A, a cross sectional view of the pod pumps 820, 828 in the cassette is shown. The details of the attachment of the membrane 1226 can be seen in this view. Again, in the exemplary embodiment, the membrane 1226 gasket is pinched by the midplate 1000 and the bottom plate 1100. A rim on the midplate 1000 provides a feature, for the gasket to seal the pod pump 820, 828 chamber located in the top plate 900.

Figure 13B:
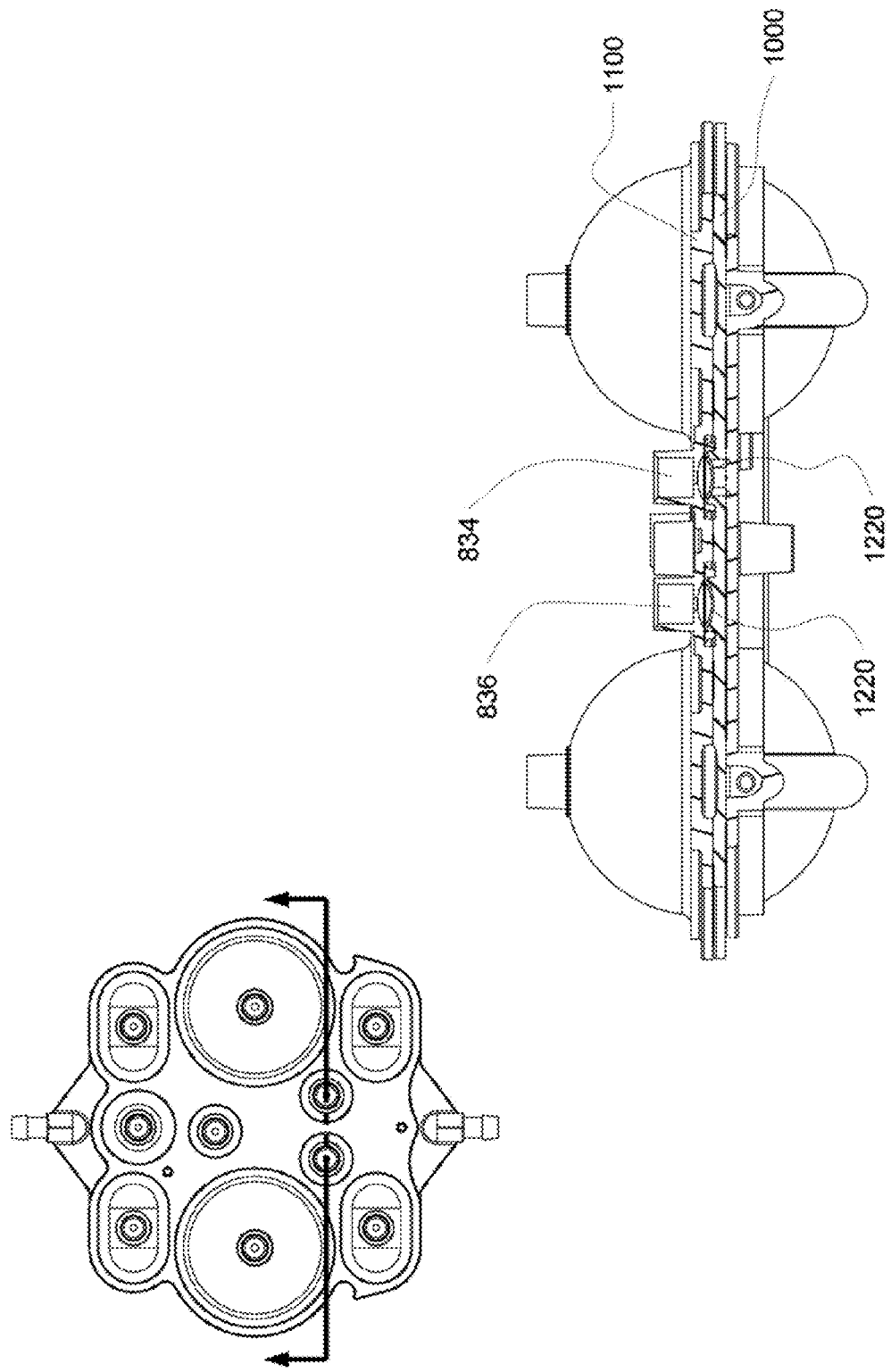

Referring next to FIG. 13B, this cross sectional view shows the valves 834, 836 in the assembled cassette. The membranes 1220 are shown assembled and are held in place, in the exemplary embodiment, by being sandwiched between the midplate 1000 and the bottom plate 1100.

Figure 13C:
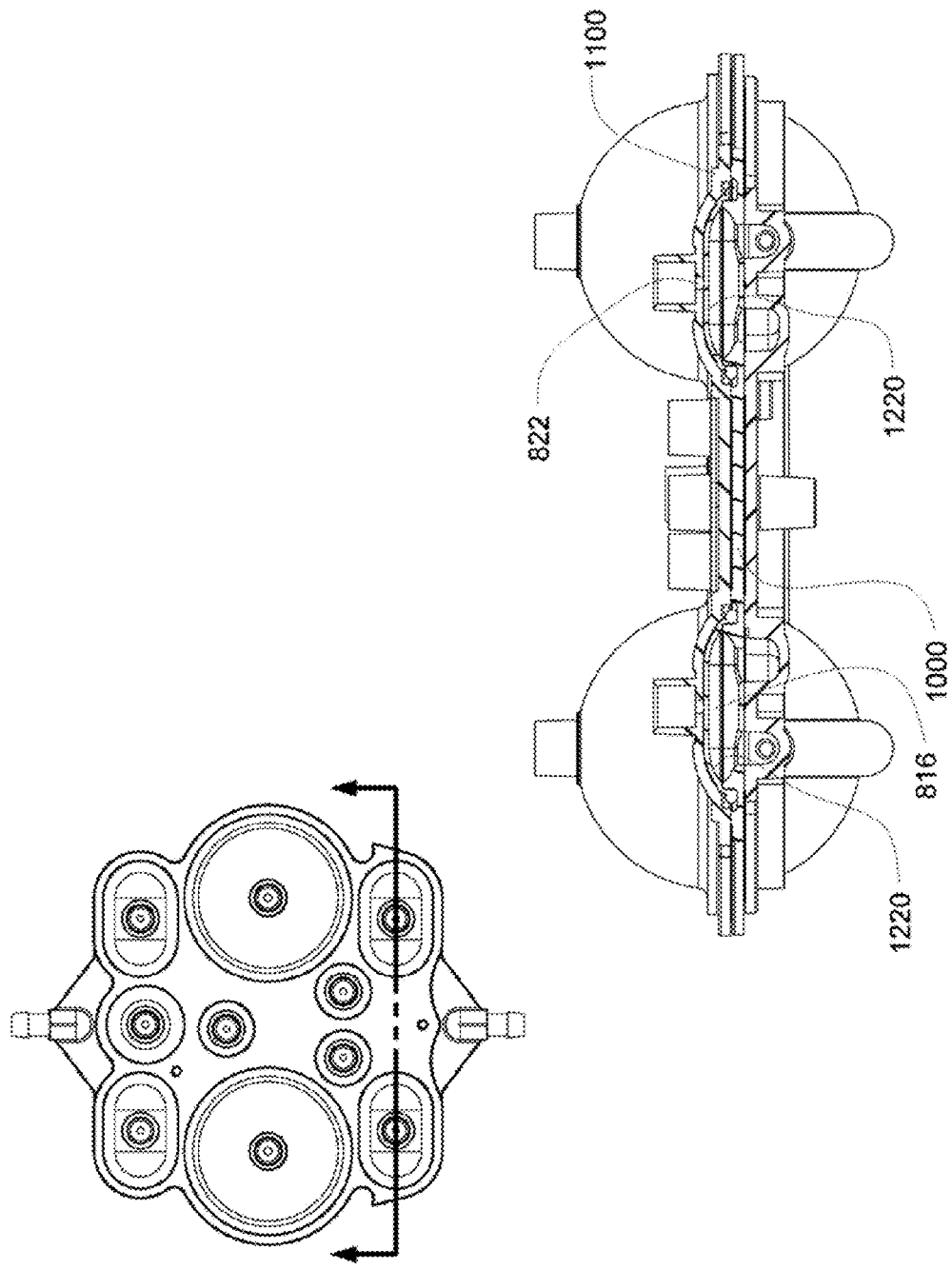

Referring next to FIG. 13C, this cross sectional view shows the valves 816, 822 in the assembled cassette. The membranes 1220 are shown assembled and are held in place, in the exemplary embodiment, by being sandwiched between the midplate 1000 and the bottom plate 1100.

Figure 14A:
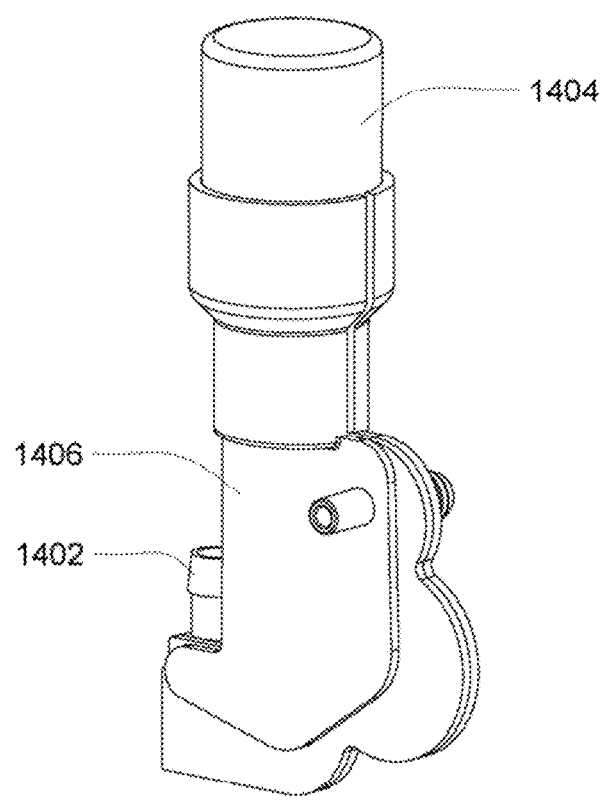
FIGS. 14A-14B show an assembled alternate embodiment of the metering pump.
Figure 14B:
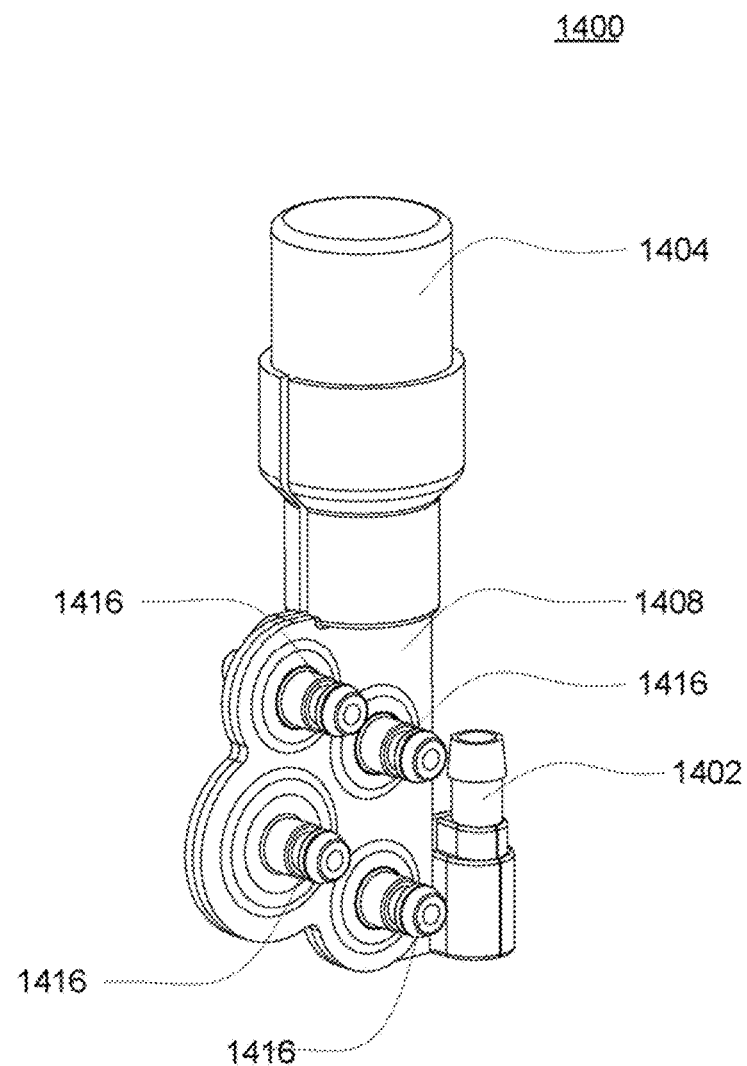

Referring now to FIGS. 14A-14B, an assembled alternate embodiment of the metering pump 1400 is shown. In this embodiment, the metering pump 1400 connects to the cassette (not shown), thus it is not integral with the cassette. Referring to FIG. 14A, the metering pump 1400 includes a top plate 1406 and a fluid connection to the cassette 1402. A container 1404 is shown in the metering pump 1400. The container 1404 contains a liquid second fluid and will be fluidly connected to the cassette fluid paths via the fluid connection to the cassette 1402.

Figure 14D:
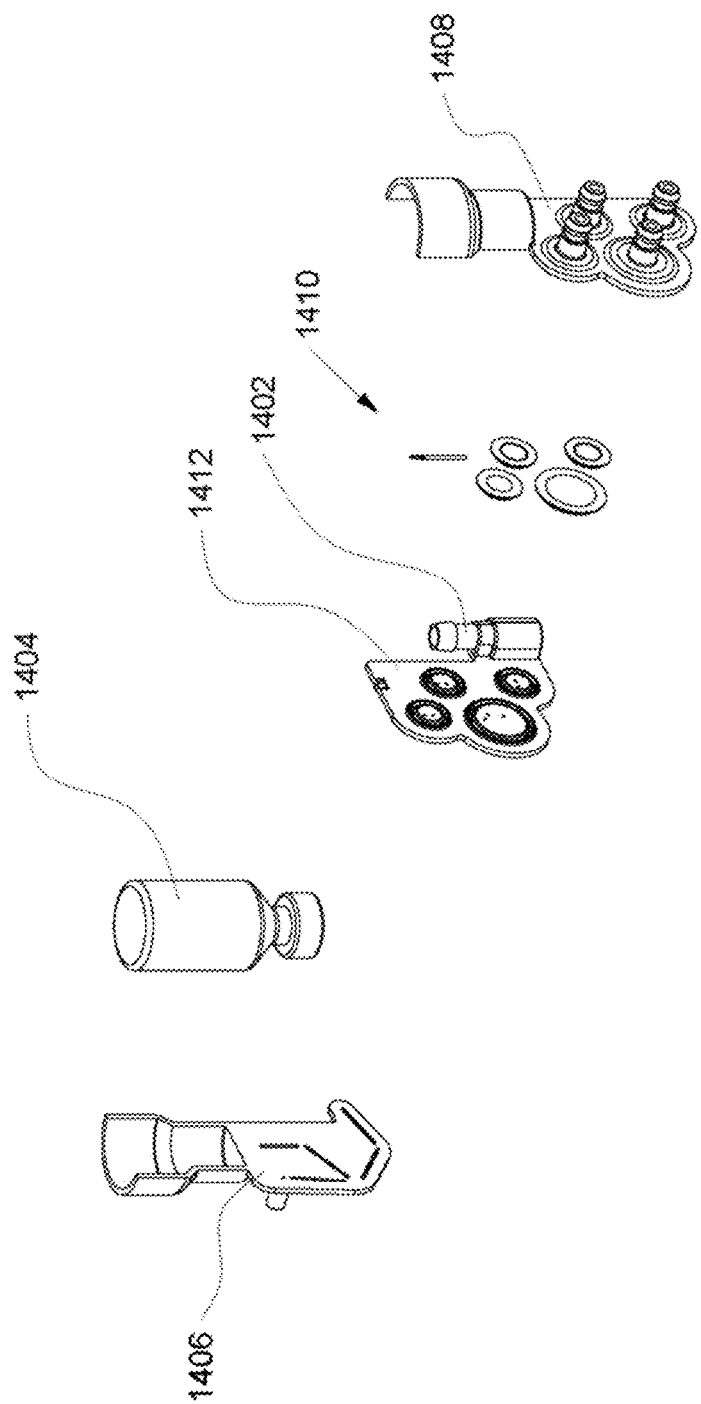
Figure 14E:
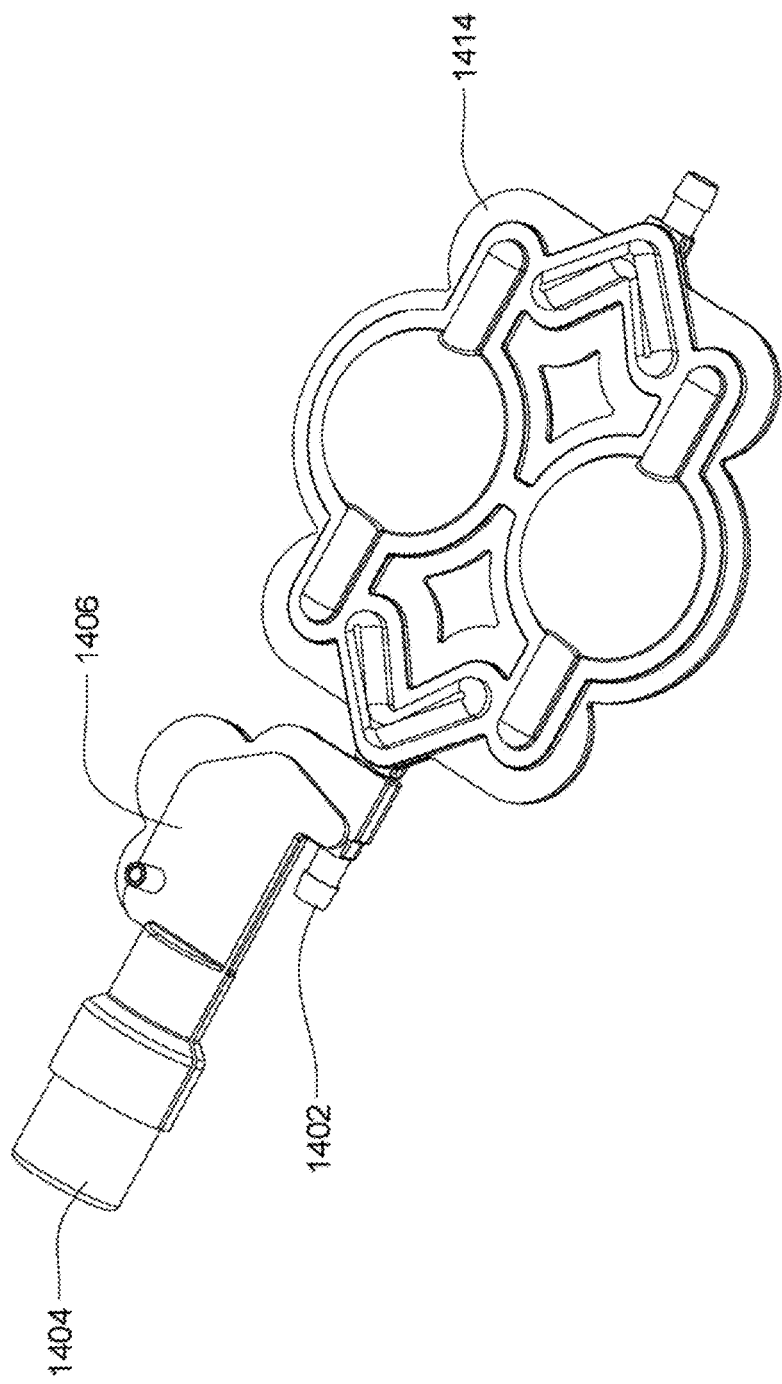
FIG. 14E show an assembled alternate embodiment of the metering pump connected to a cassette.
Figure 14F:
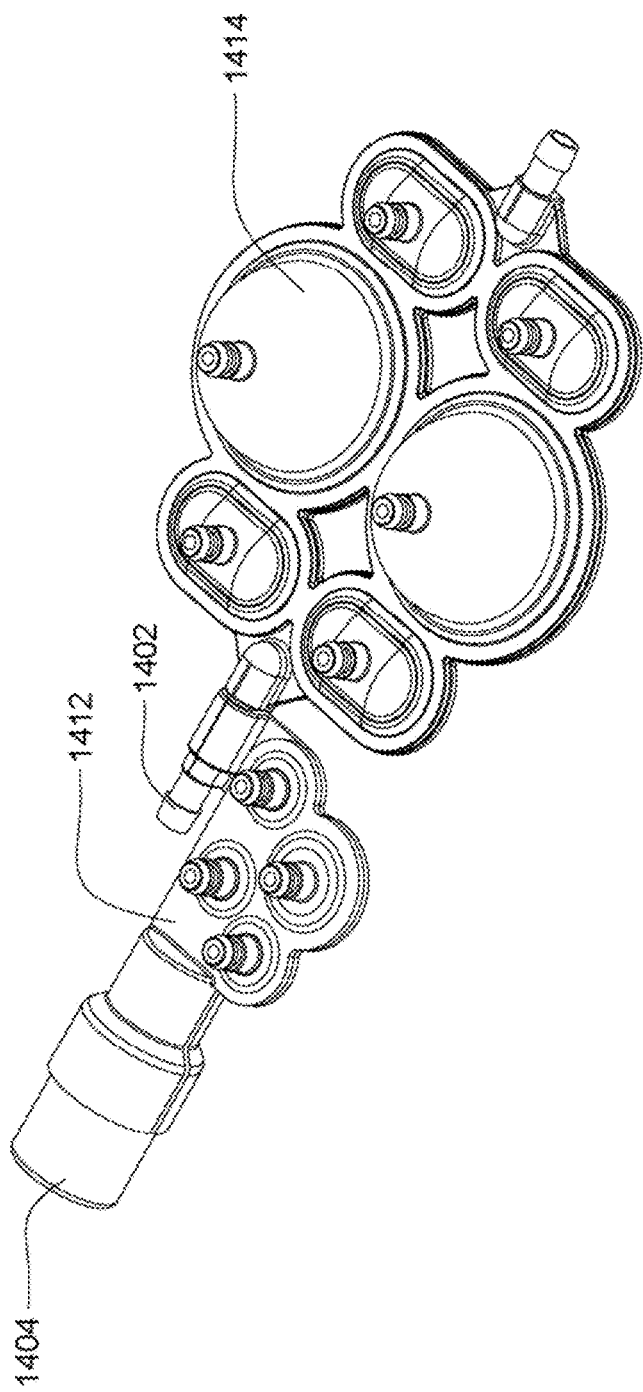
FIG. 14F shows a partially assembled alternate embodiment of the metering pump connected to a cassette.

Referring next to FIG. 14B, the metering pump 1400 also includes a bottom plate 1408 that includes air actuation ports 1416. Referring next to FIGS. 14C and 14D, exploded views of the metering pump is shown. The membranes 1410 that complete the valves in the midplate 1412 are shown. The assembled metering pump on a cassette 1414 is shown in FIG. 14E. FIG. 14F shows a partially assembled metering pump on a cassette 1414, where the midplate 1408 is not covered by the top plate 1406.

Figure 15A:
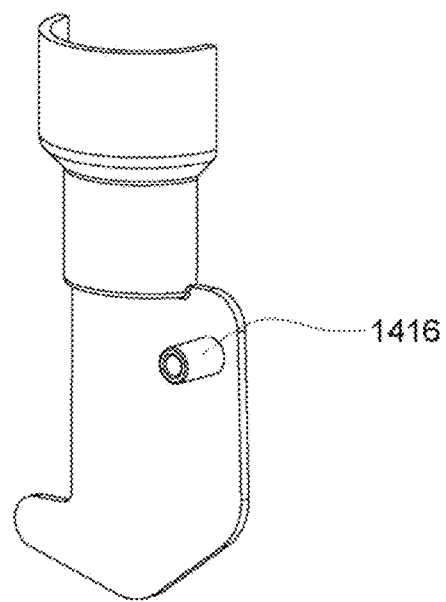
FIGS. 15A-15B show isometric and top views of outer top plate according to an alternate embodiment of the metering pump.
Figure 15B:
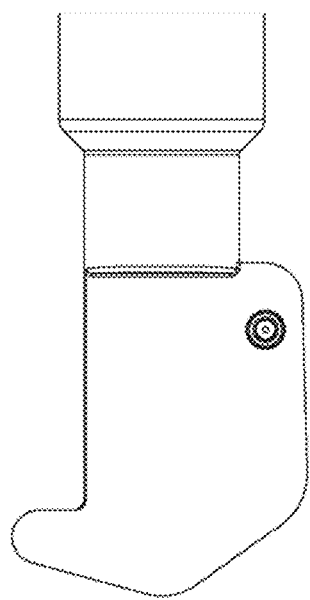
Figure 15C:
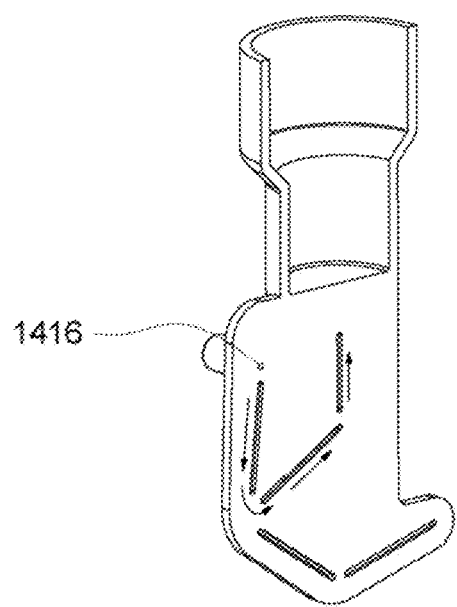
FIGS. 15C-15D show bottom views of the inner top plate according to an alternate embodiment of the metering pump.
Figure 15D:
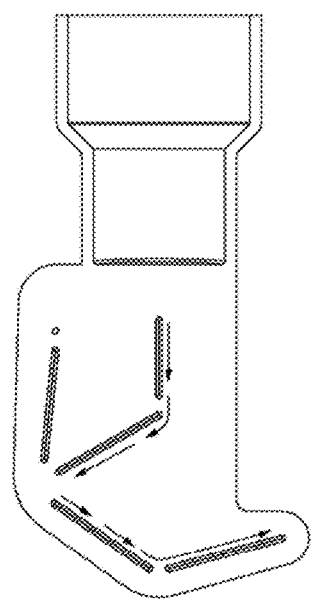

Referring now to FIGS. 15A-15D, the top plate of the alternate embodiment of the metering pump contains many of the same features as seen in the top plate of the exemplary embodiment of the cassette described above with respect to the metering pump in FIGS. 9C-9D. The air inlet 1416 in some embodiments includes an air filter, similar to the embodiments described above. Referring now to FIG. 15C, the air flow fluid path is shown with arrows. The air is taken in through the air inlet and then pushed towards the container (not shown). Referring now to FIG. 15D, the second fluid flow path is shown with arrows. The second fluid is pumped from the container (not shown) and out to the cassette at point 836. Thus, the alternate embodiment of the metering pump shown in FIGS. 14A-17D is another structural implementation of the fluid flow-path schematic shown in FIG. 8, only the metering pump component is not integral with the cassette, rather, attached to the cassette.

Figure 16A:
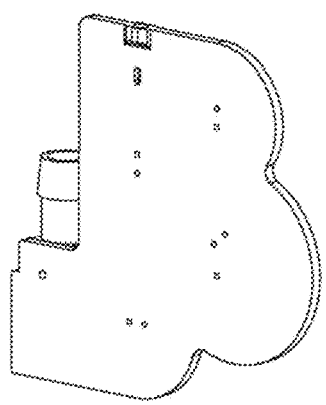
FIGS. 16A-16B show isometric and top views of the liquid side midplate according to an alternate embodiment of the metering pump.
Figure 16B:
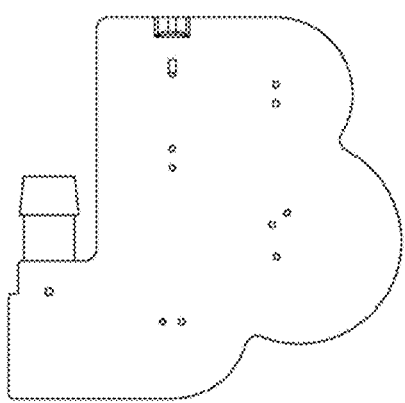
Figure 16C:
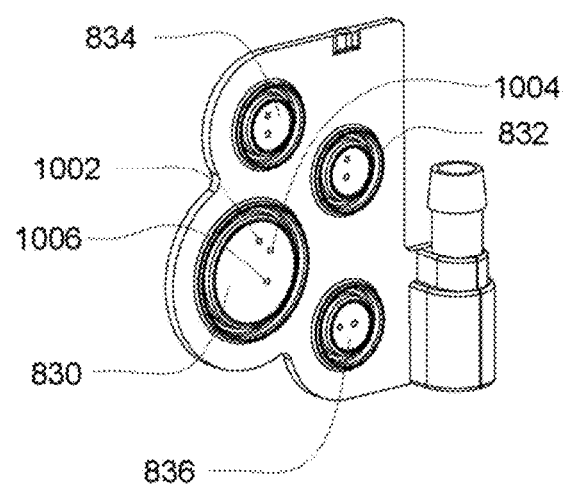
FIGS. 16C-16D show isometric and bottom views of the air side midplate according to an alternate embodiment of the metering pump.
Figure 16D:
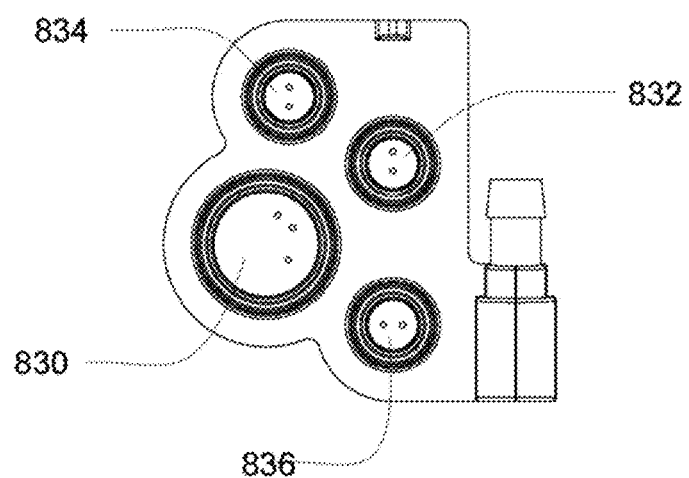

Referring now to FIGS. 16A-16B, the holes indicating the flow path of the fluid are shown. Referring now to FIGS. 16C and 16D, the air side of the midplate 1412 is shown. The air side of the valves 832, 834, 836, including the metering pump 830 are shown. The holes in the valves 832, 834, 836, and the metering pump 830 correspond to the valves around the metering pump in the schematic shown in FIG. 8, and also in the exemplary embodiment of the midplate of the cassette shown in FIGS. 10A-10C. Thus, although the metering pump and the corresponding valves and fluid lines are outside of the cassette in this embodiment, the valves and fluid lines are similar. Thus, much of the description above with respect to the exemplary embodiment metering pump features is applicable to the alternate embodiment of the metering pump.

Figure 17A:
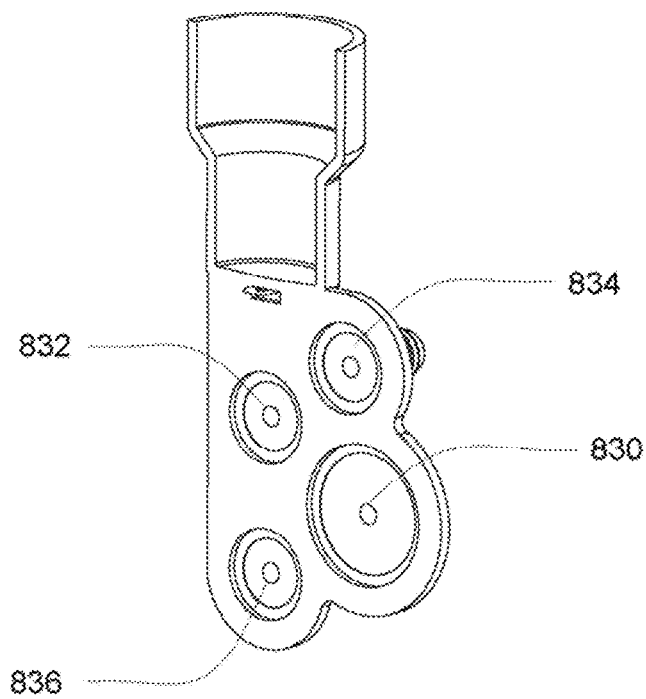
FIGS. 17A-17B show isometric and top views of the inner bottom plate according to an alternate embodiment of the metering pump.
Figure 17B:
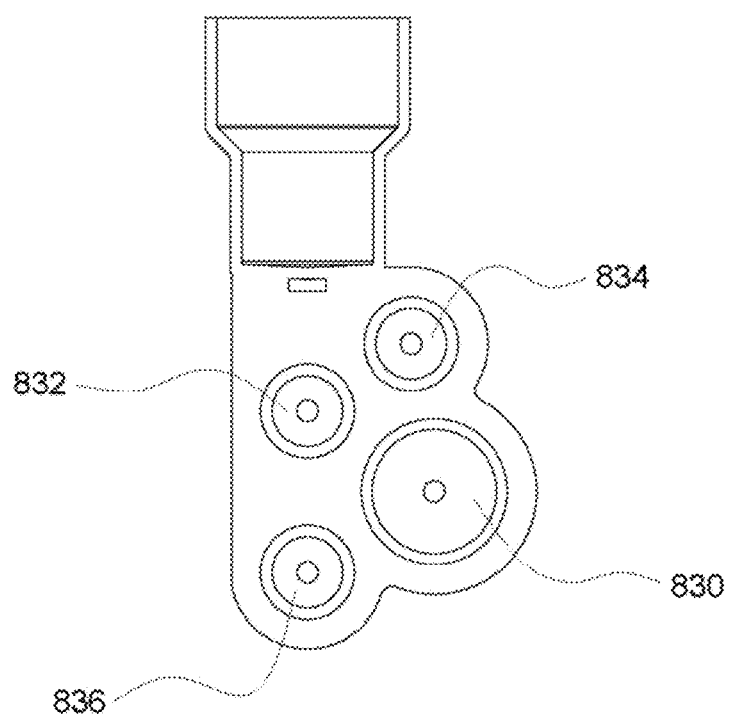
Figure 17C:
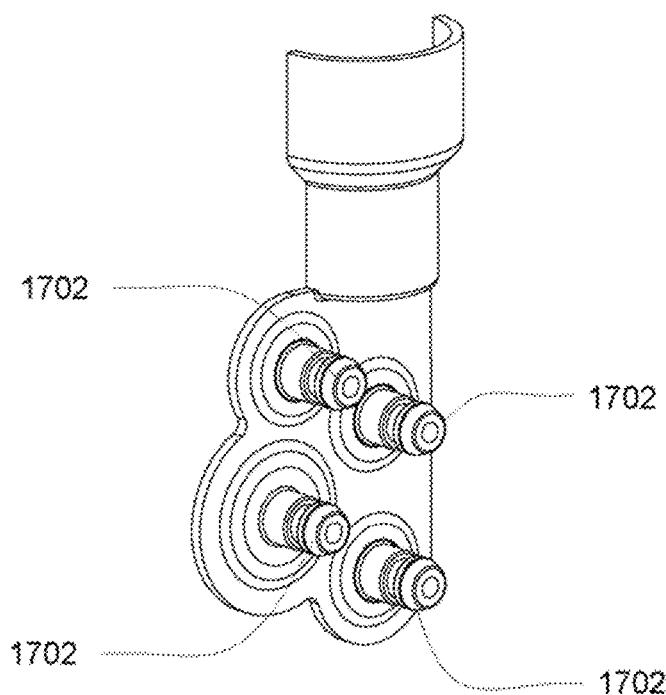
FIGS. 17C-17D show isometric and bottom views of the outer bottom according to an alternate embodiment of the metering pump.
Figure 17D:
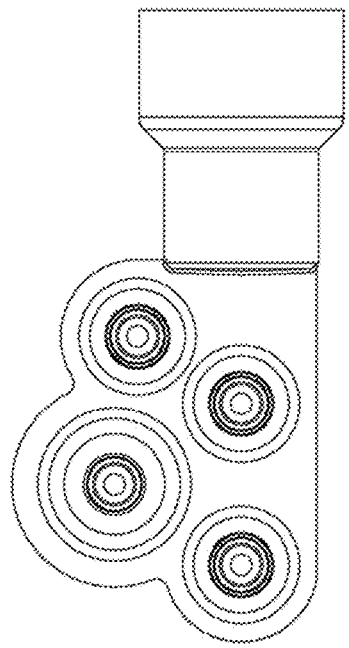

Referring now to FIGS. 17A and 17B, the inner bottom plate 1408 is shown. The corresponding actuation sides of the valves 832, 834, 836 and metering pump 830 are shown. Referring now to FIGS. 17C and 17D, the outer bottom plate 1408 is shown with the actuation ports 1702 which providing access for the air to actuate the metering pump and the valves.

As described above, the exemplary embodiment is one cassette embodiment that incorporates the exemplary fluid flow-path schematic shown in FIG. 8. However, there are alternate embodiments of the cassette that incorporate many of the same features of the exemplary embodiment, but with a slightly different structural design. One of these alternate embodiments is the embodiment shown in FIGS. 18A-22B.

In the alternate embodiment shown in FIGS. 18A-22B, the corresponding numbering of the elements used with respect to FIGS. 9A-12D apply. The cross sections views of FIGS. 22A and 22B correspond to FIGS. 13A and 13C respectively. The two embodiments vary only slightly and this variation can best be seen in FIGS. 18A-18E when compared to the exemplary embodiment in FIGS. 9A-9E. In particular, the raised flow path 908, 910 on the pod pumps 820, 828 in the alternate embodiment of FIGS. 18A-18E has dimensions that are a smaller than in the exemplary embodiment shown in FIGS. 9A-9E. Additionally, the fluid paths in the exemplary embodiment of FIGS. 9A-9E have more squared off edges, whereas in the alternate embodiment shown in FIGS. 18A-18E, the fluid paths have more rounded edges. The exemplary embodiment's edges being more squared off lend to easier manufacture as the laser welding is more efficient and effective in this embodiment.

Referring now to FIGS. 23A-27B another alternate embodiment of the cassette is shown. However, in this embodiment, the metering pump is not incorporated or integrated into the cassette. Thus, in this embodiment of the cassette, where a metering pump is desired, a separate metering pump is connected to the cassette. One embodiment of a separate metering pump is described and shown with respect to FIGS. 14A-17D. Many of the features, i.e., the pod pumps and the fluid lines are similar to the exemplary embodiment shown in FIGS. 9A-12D. Thus, the description and numbering of the figures corresponding to FIGS. 9A-12D can be applied to FIGS. 23A-26D. The cross section views in the alternate embodiment shown in FIGS. 27A and 27B correspond to cross sectional views shown in FIGS. 13A and 13C respectively.

Figure 24A:
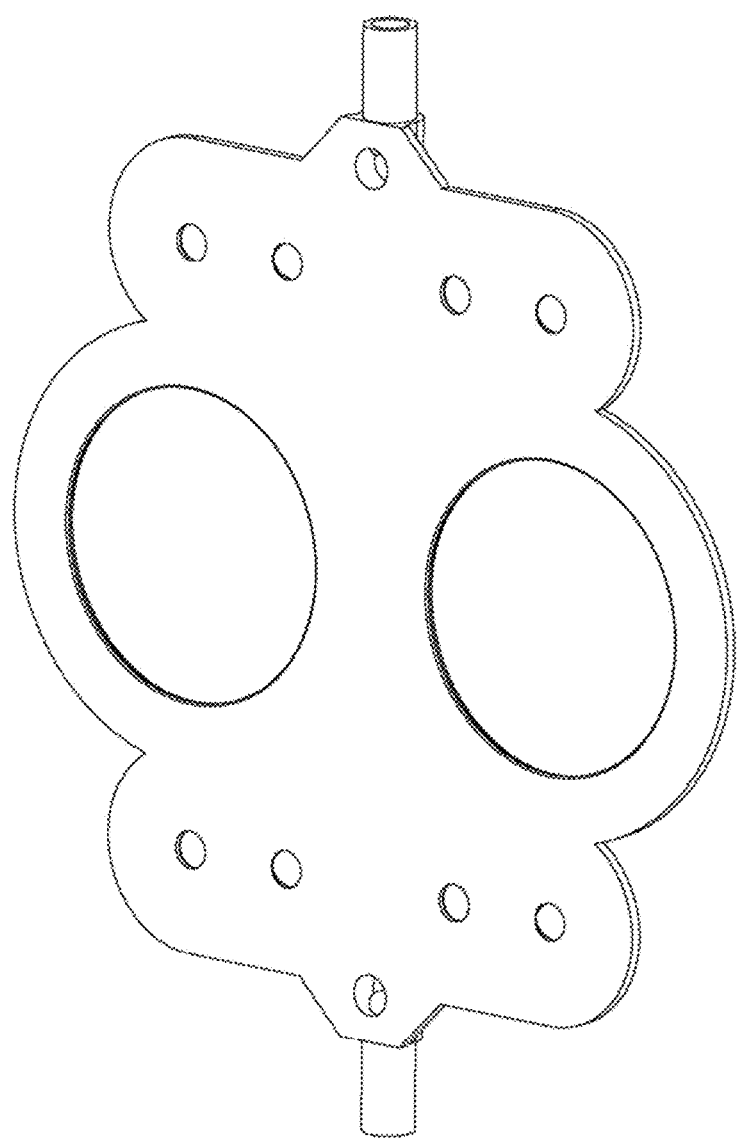
FIGS. 24A-24B show isometric and top views of the liquid side midplate according to an alternate embodiment of the cassette.
Figure 24B:
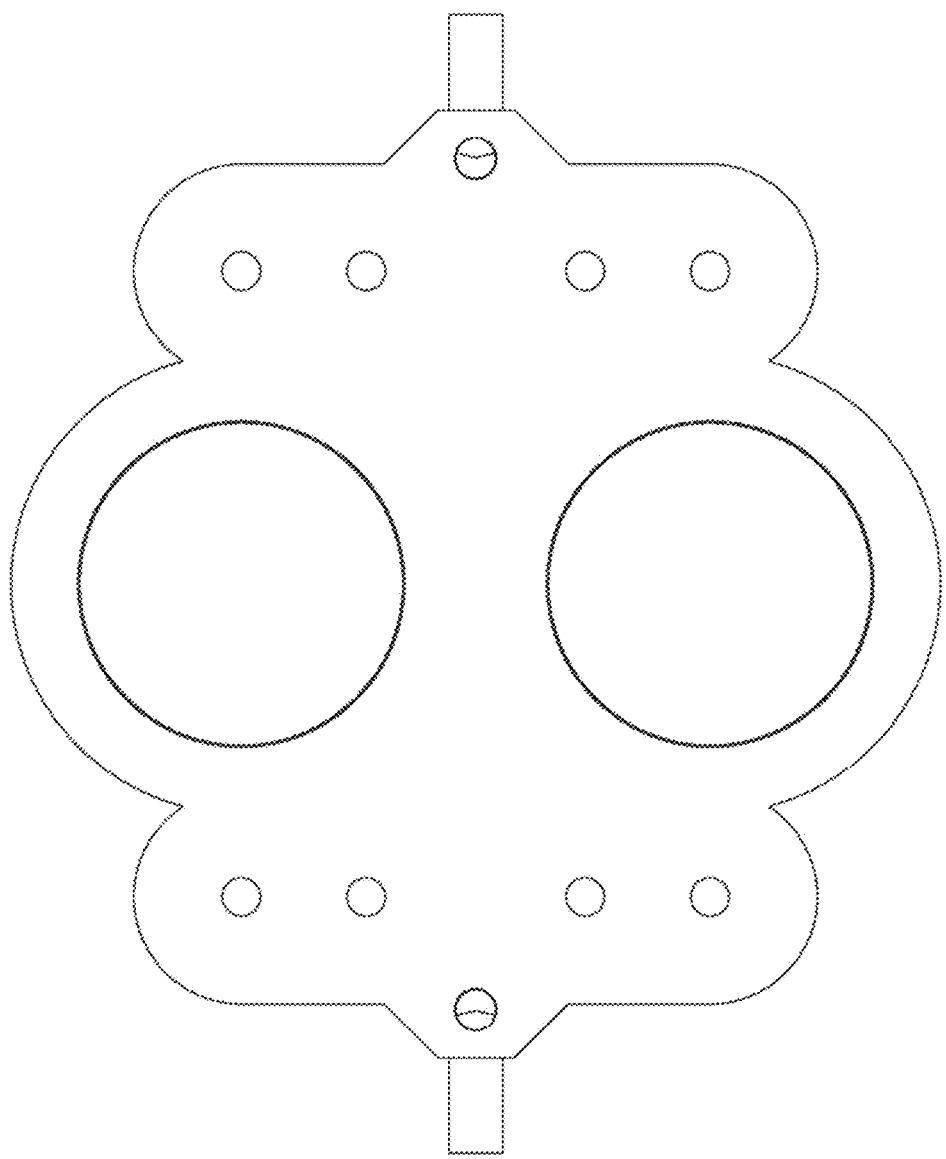
Figure 24C:
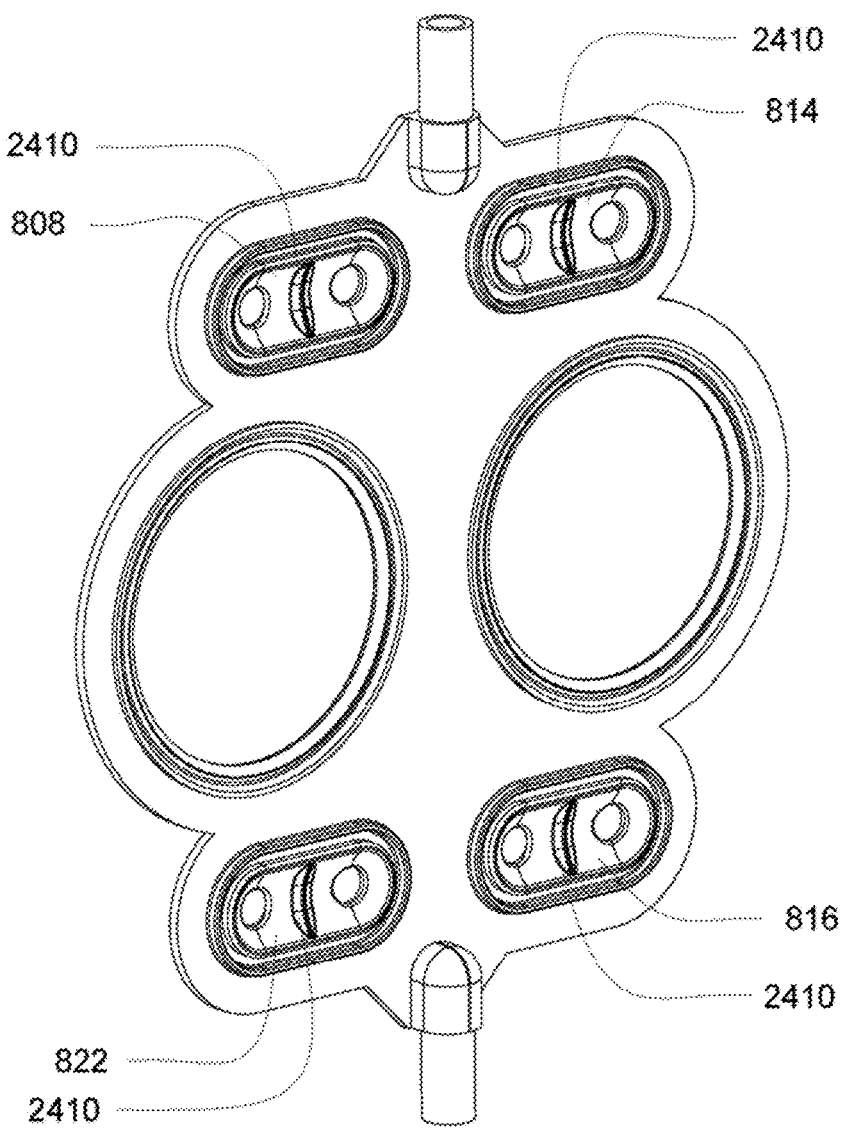
FIGS. 24C-24D show isometric and bottom views of the air side midplate according to an alternate embodiment of the cassette.
Figure 24D:
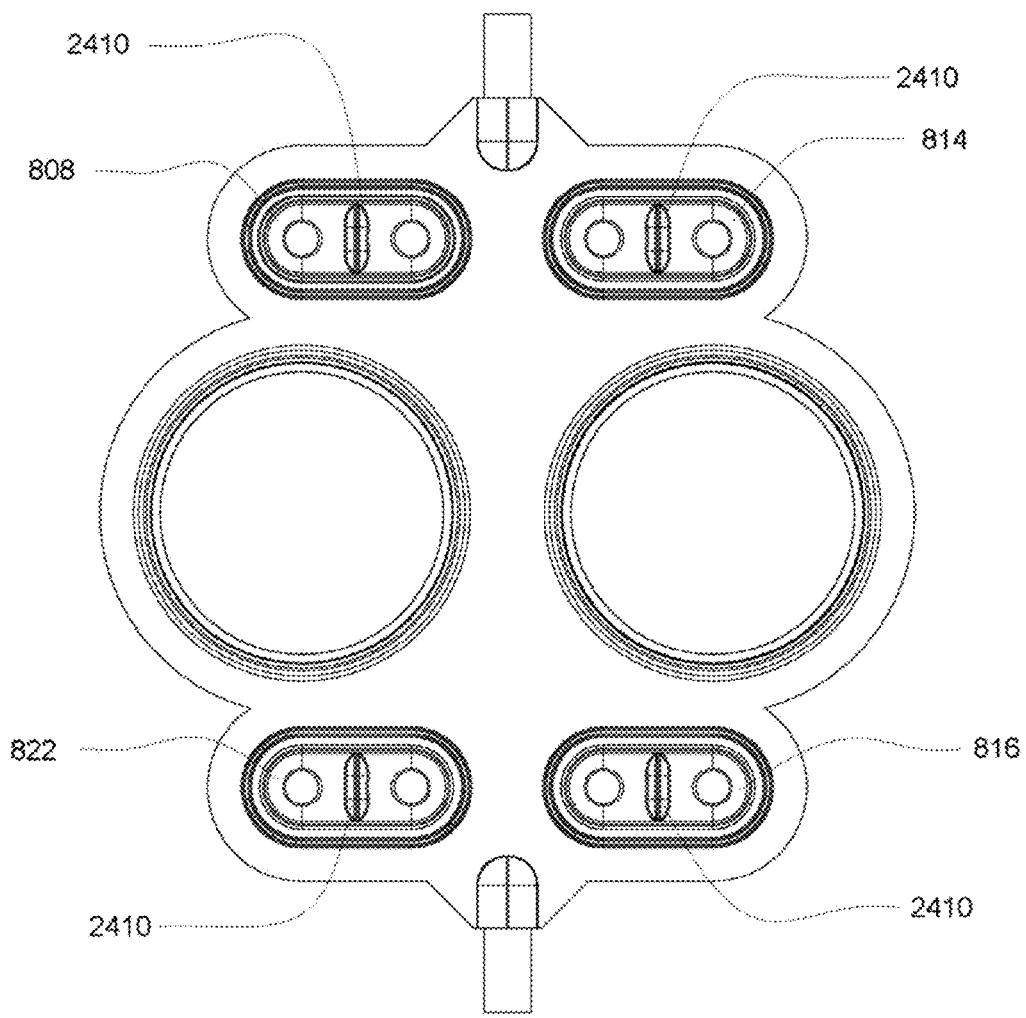
Figure 24E:
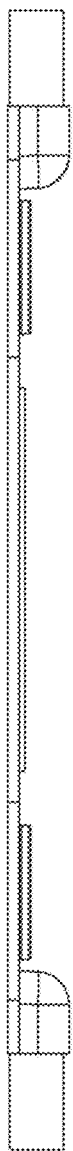
FIG. 24E shows a side view of the alternate embodiment of the midplate.

Referring now to FIGS. 24C and 24D, an alternate view of the valves 808, 814, 816, 822 is shown. Comparing the valves 808, 814, 816, 822 in FIGS. 24C-24D to the exemplary embodiment shown in FIGS. 10C-10D as 808, 814, 816, 822, it is apparent that the valves 808, 814, 816, 822 in FIGS. 24C-24D include a raised feature 2410, whereas the valves 808, 814, 816, 822 in FIGS. 10C-10D do not. The valves 808, 814, 816, 822 shown in FIGS. 10C-10D include a smooth construction and do not include any raised or textured features. Referring again to FIGS. 24C and 24D, the raised feature 2410 of the valves 808, 814, 816, 822 provides for a different sealing mechanism for the fluid flowing from one fluid path to the next (where each fluid path is indicated by the holes in the valves 808, 814, 816, 822).

Figure 23A:
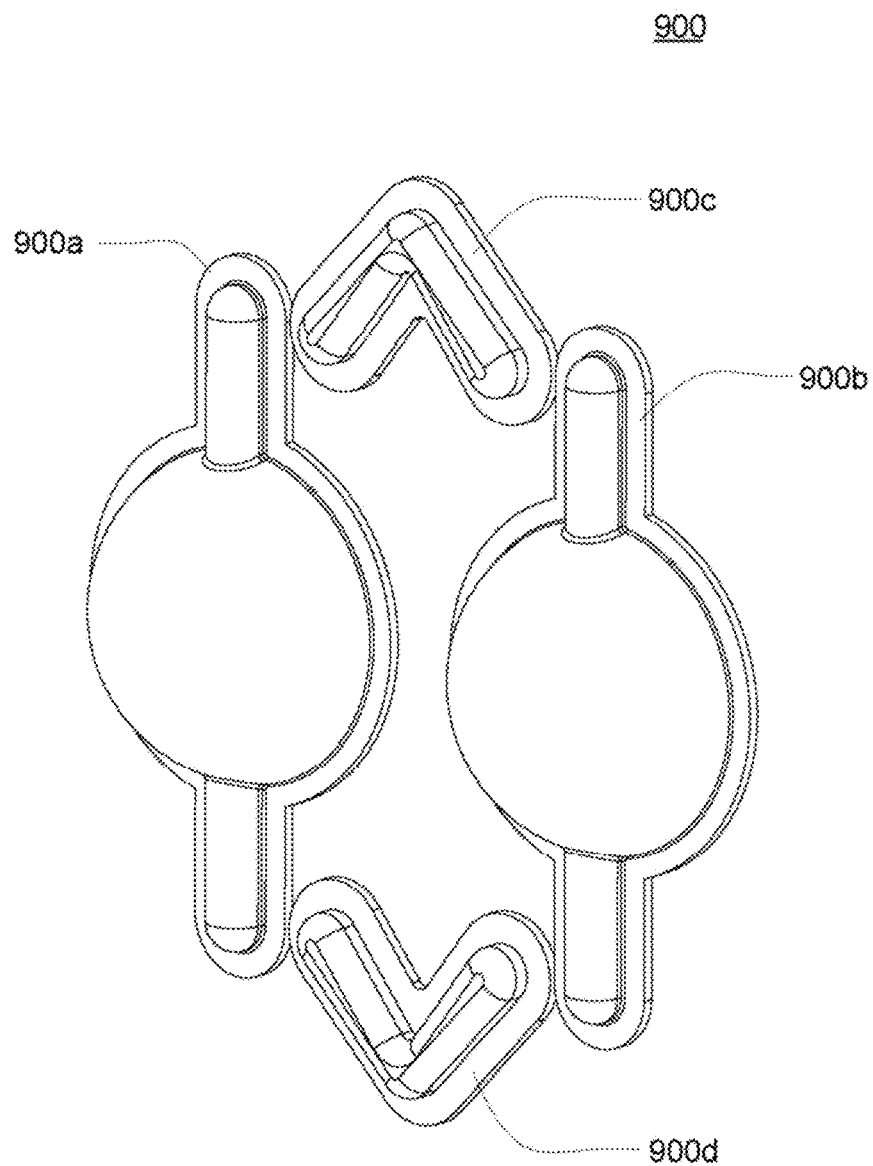
FIGS. 23A-23B show isometric and top views of outer top plate according to an alternate embodiment of the cassette.
Figure 23B:
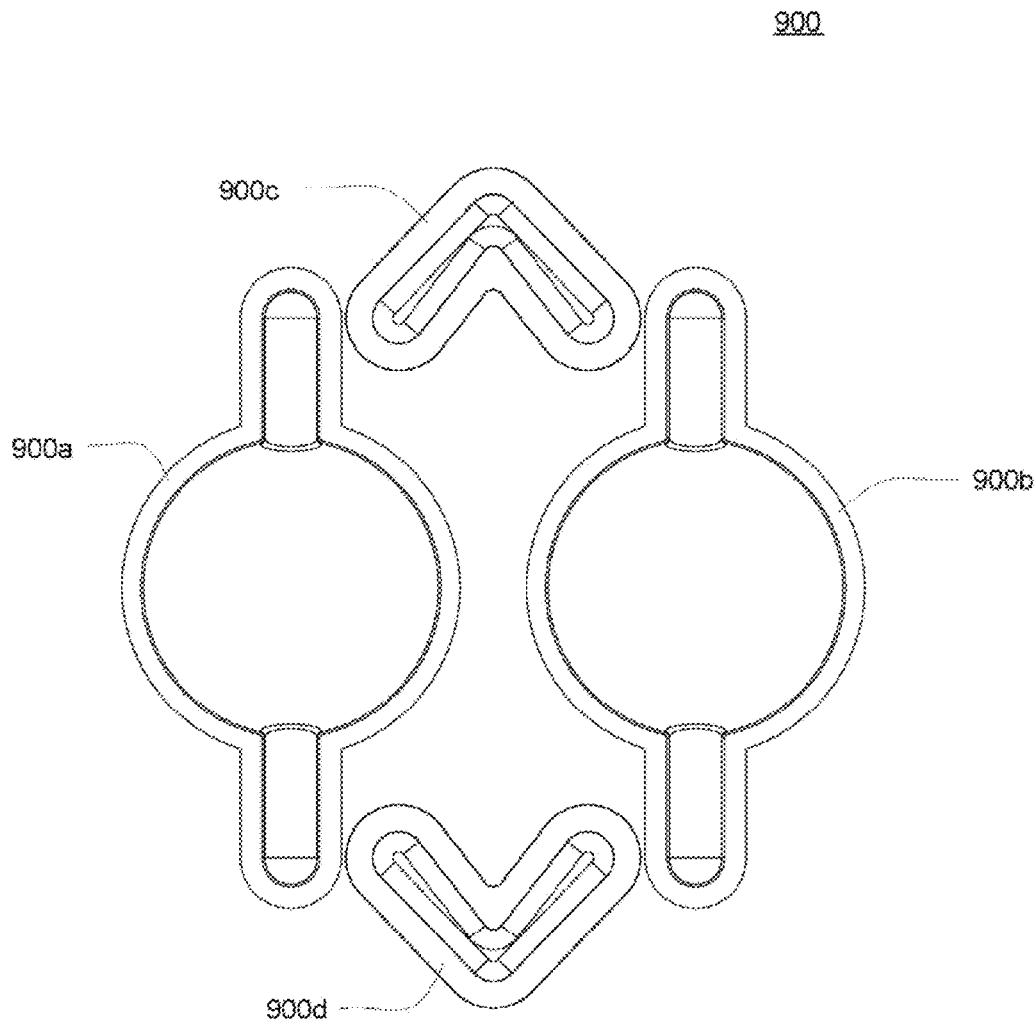
Figure 23C:
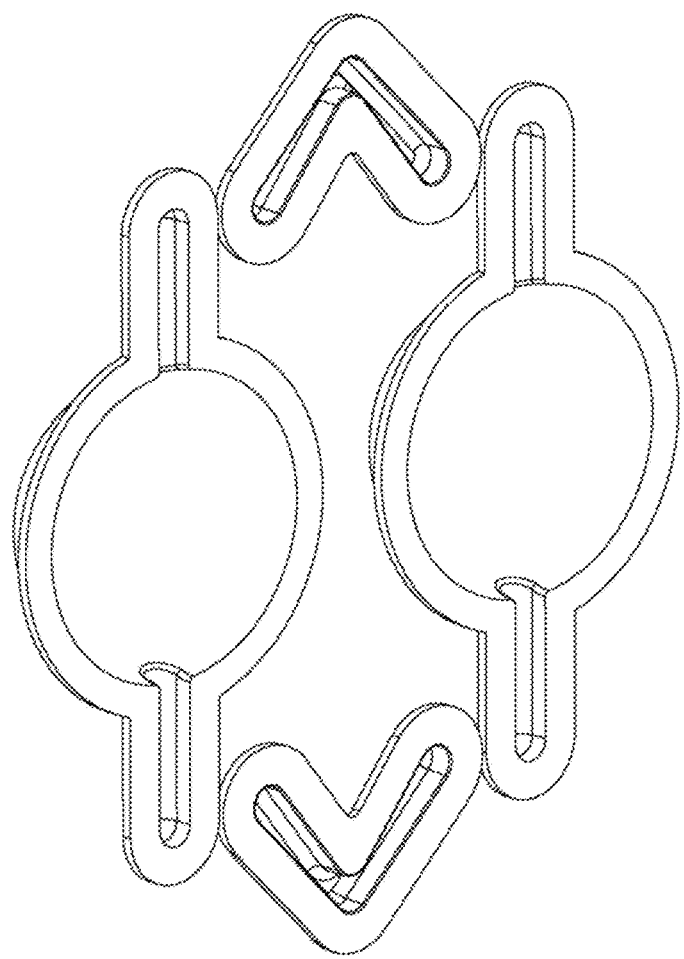
FIGS. 23C-23D show bottom views of the inner top plate according to an alternate embodiment of the cassette.
Figure 23D:
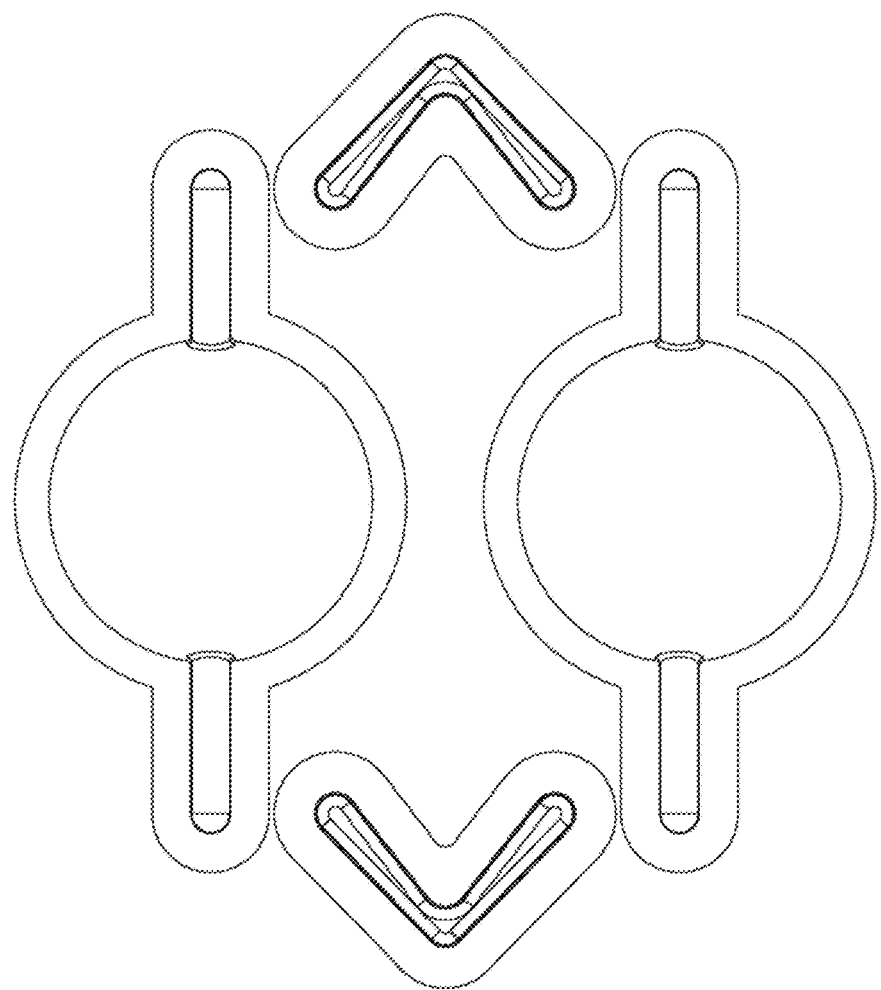
Figure 23E:
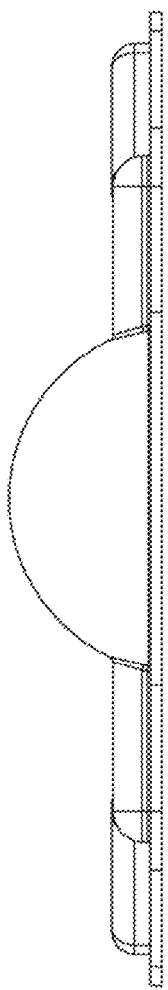
FIG. 23E shows a side view of the alternate embodiment of the top plate.

Referring now to FIGS. 23A-23B, the alternate embodiment of the top plate 900 is shown. Again, comparing this alternate embodiment to the exemplary embodiment shown in FIGS. 9A-9B, in FIGS. 9A and 9B, the top plate 900 is one solid part. However, referring again to FIGS. 23A-23B, the top plate 900 is four separate parts 900a, 900b, 900c, 900d. In manufacture, the four plates are laser welded or ultrasonically welded individually onto the fluid side of the midplate (shown in FIGS. 24A-24B). Other modes of manufacture are discussed above.

Figure 25A:
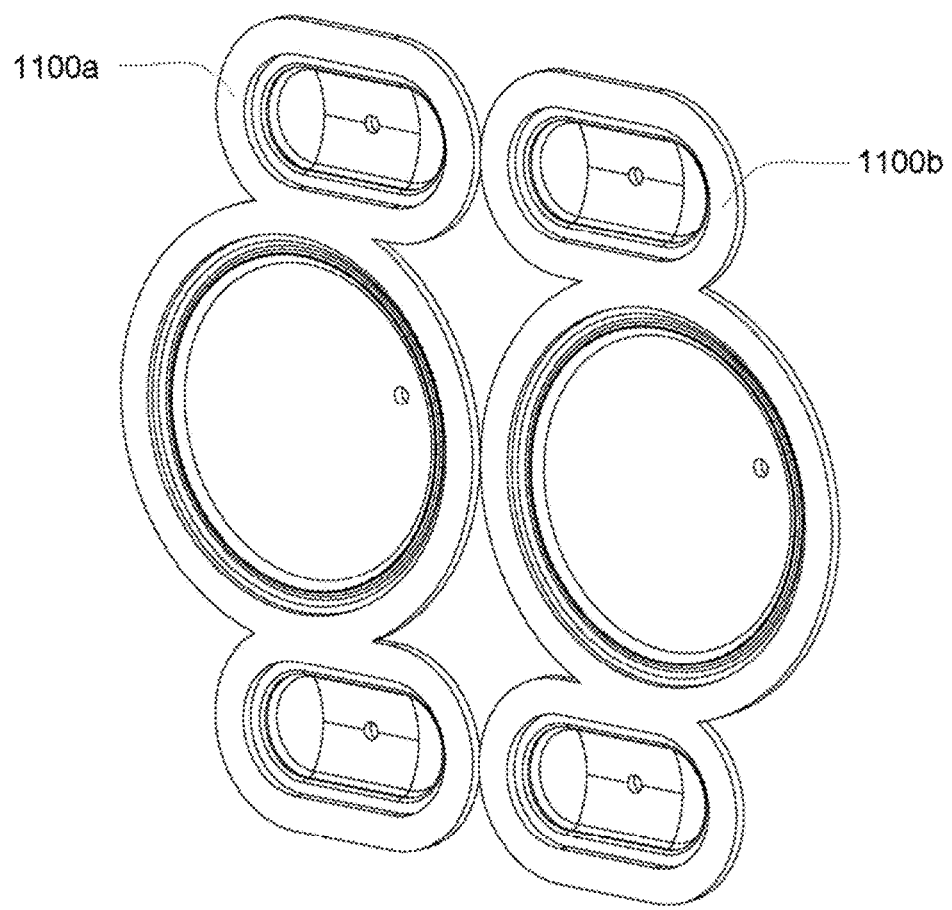
FIGS. 25A-25B show isometric and top views of the inner bottom plate according to an alternate embodiment of the cassette.
Figure 25B:
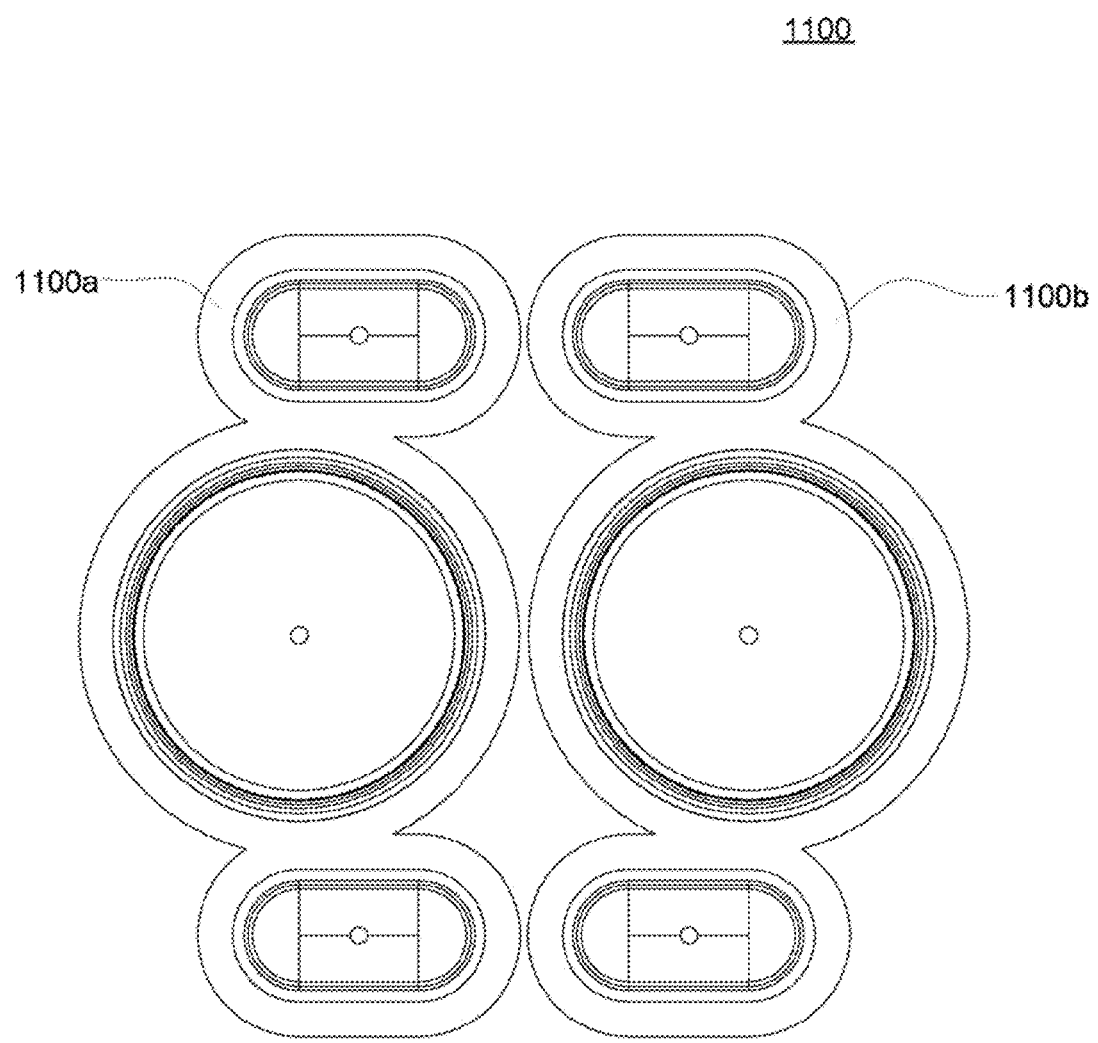
Figure 25C:
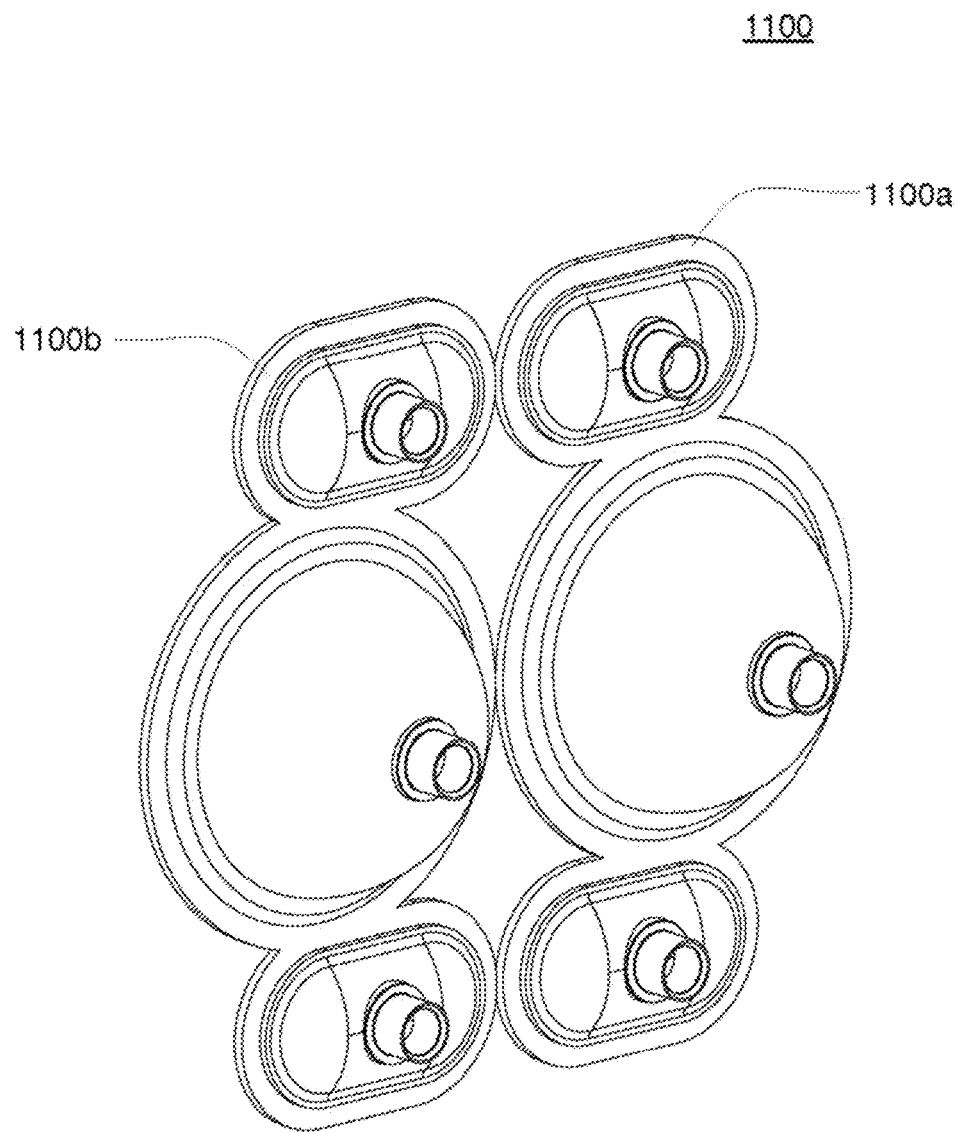
FIGS. 25C-25D show isometric and bottom views of the outer bottom according to an alternate embodiment of the cassette.
Figure 25D:
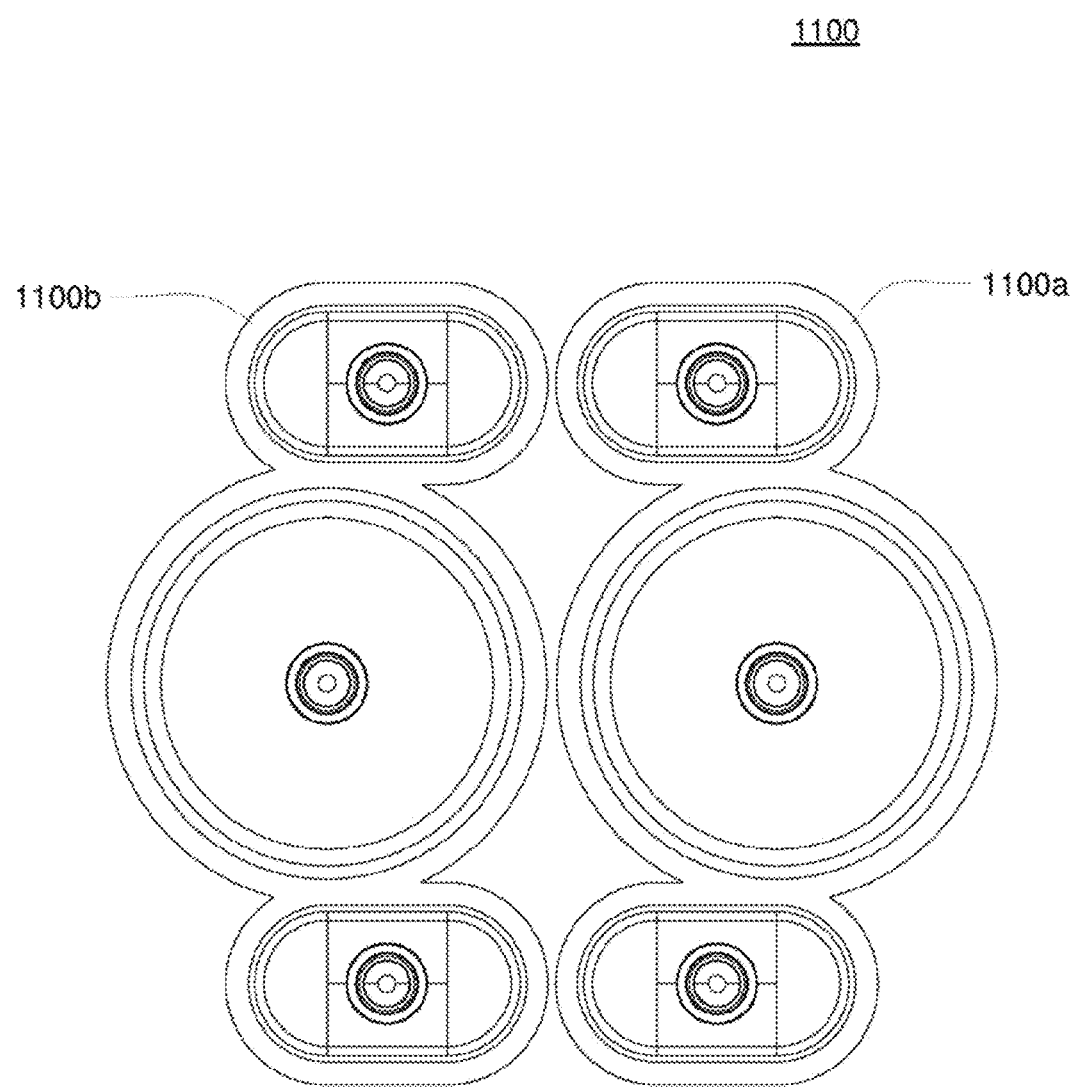
Figure 25E:
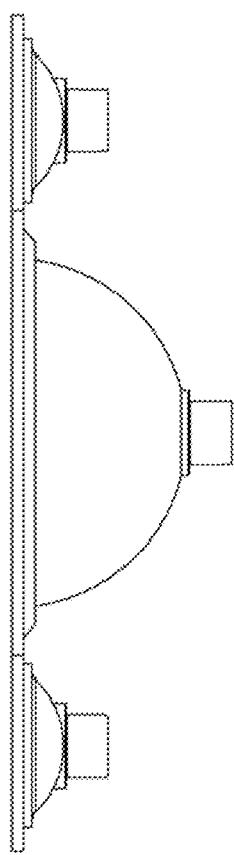
FIG. 25E shows a side view of the alternate embodiment of the bottom plate.
Figure 26A:
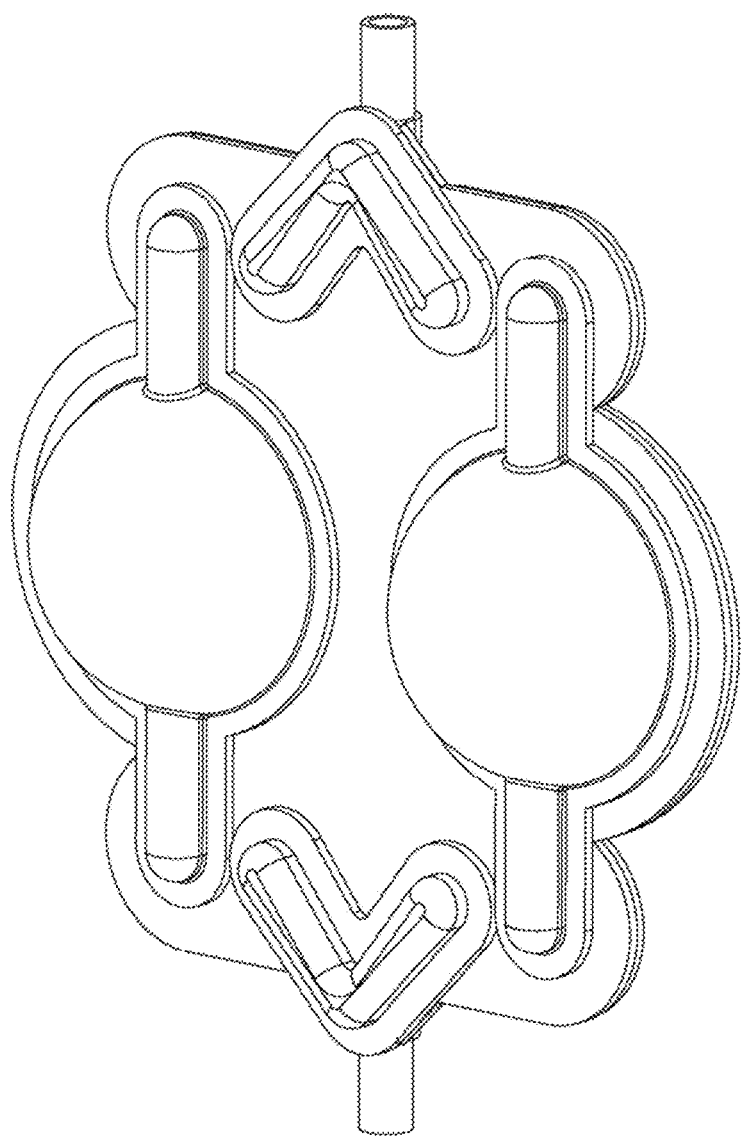
FIG. 26A is a top view of an assembled alternate embodiment of the cassette.
Figure 26B:
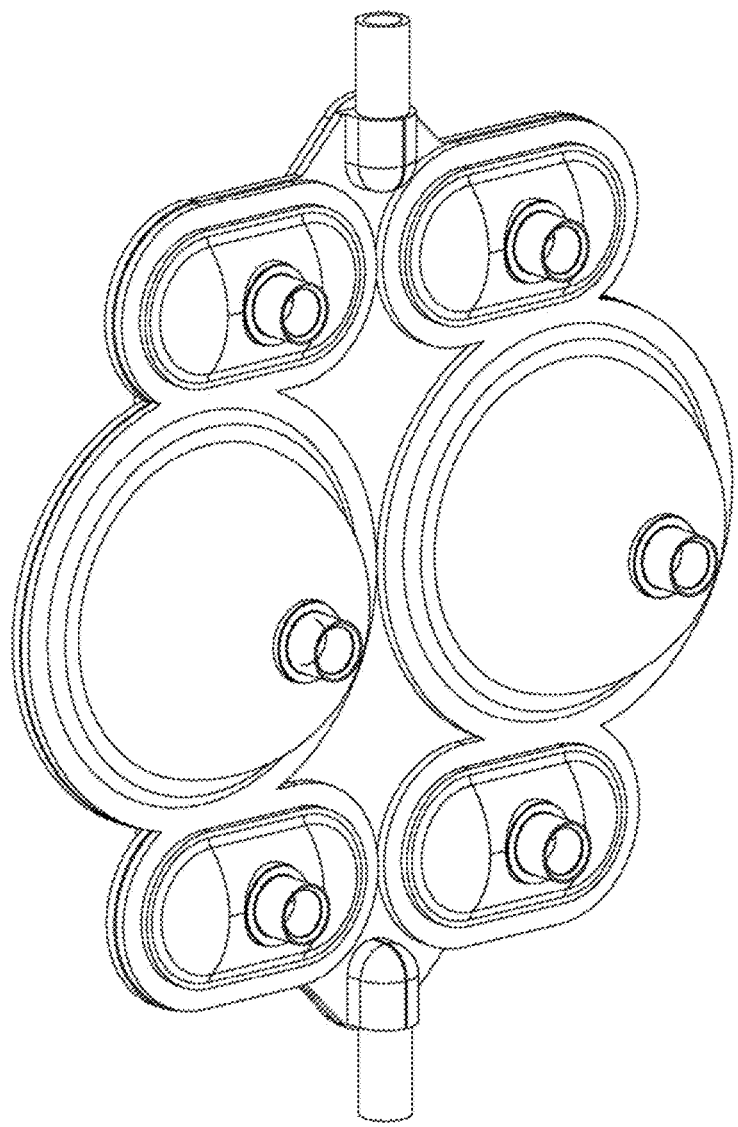
FIG. 26B is a bottom view of an assembled alternate embodiment of the cassette.
Figure 26C:
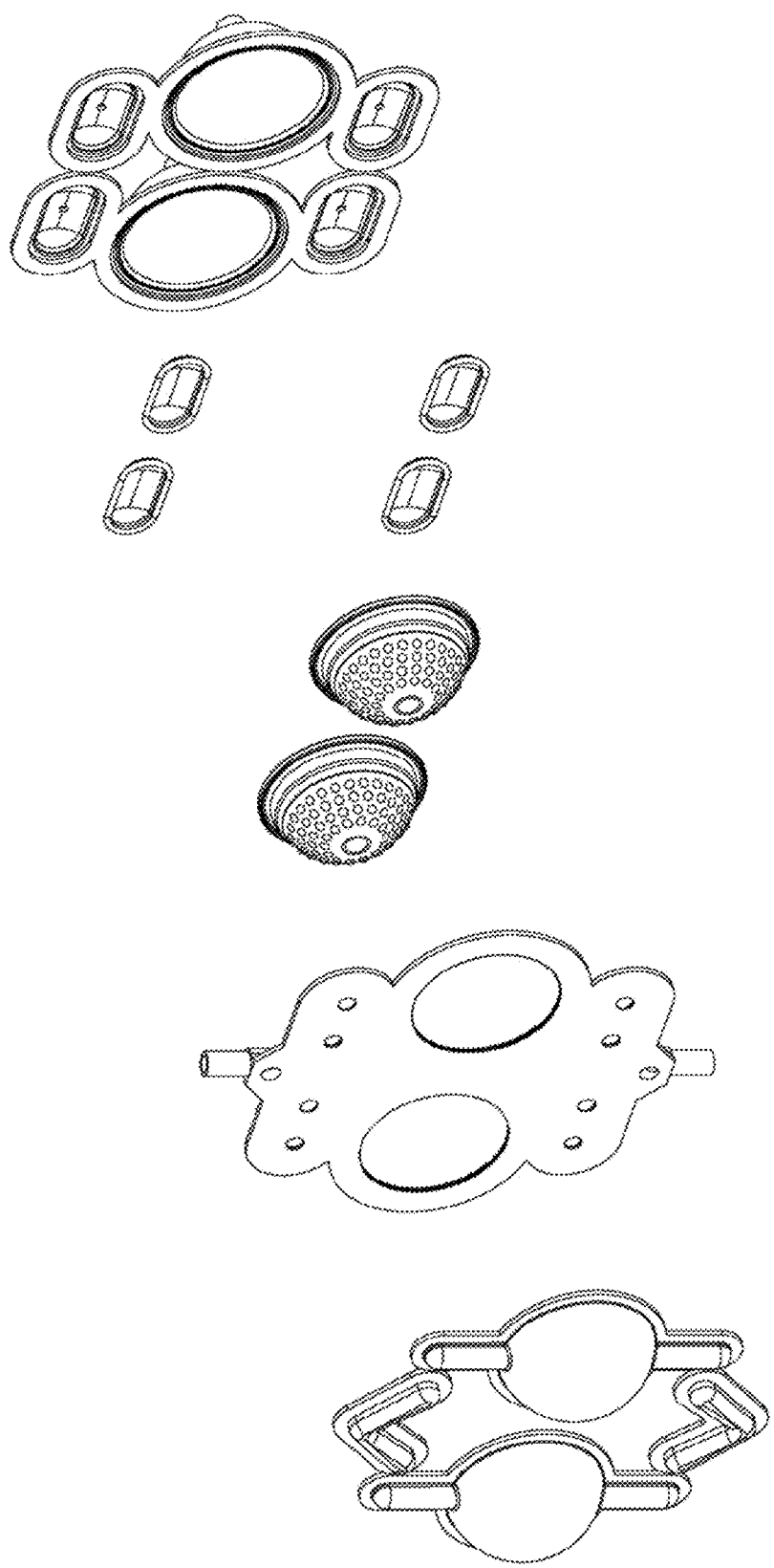
FIG. 26C is an exploded view of the assembled alternate embodiment of the cassette.
Figure 26D:
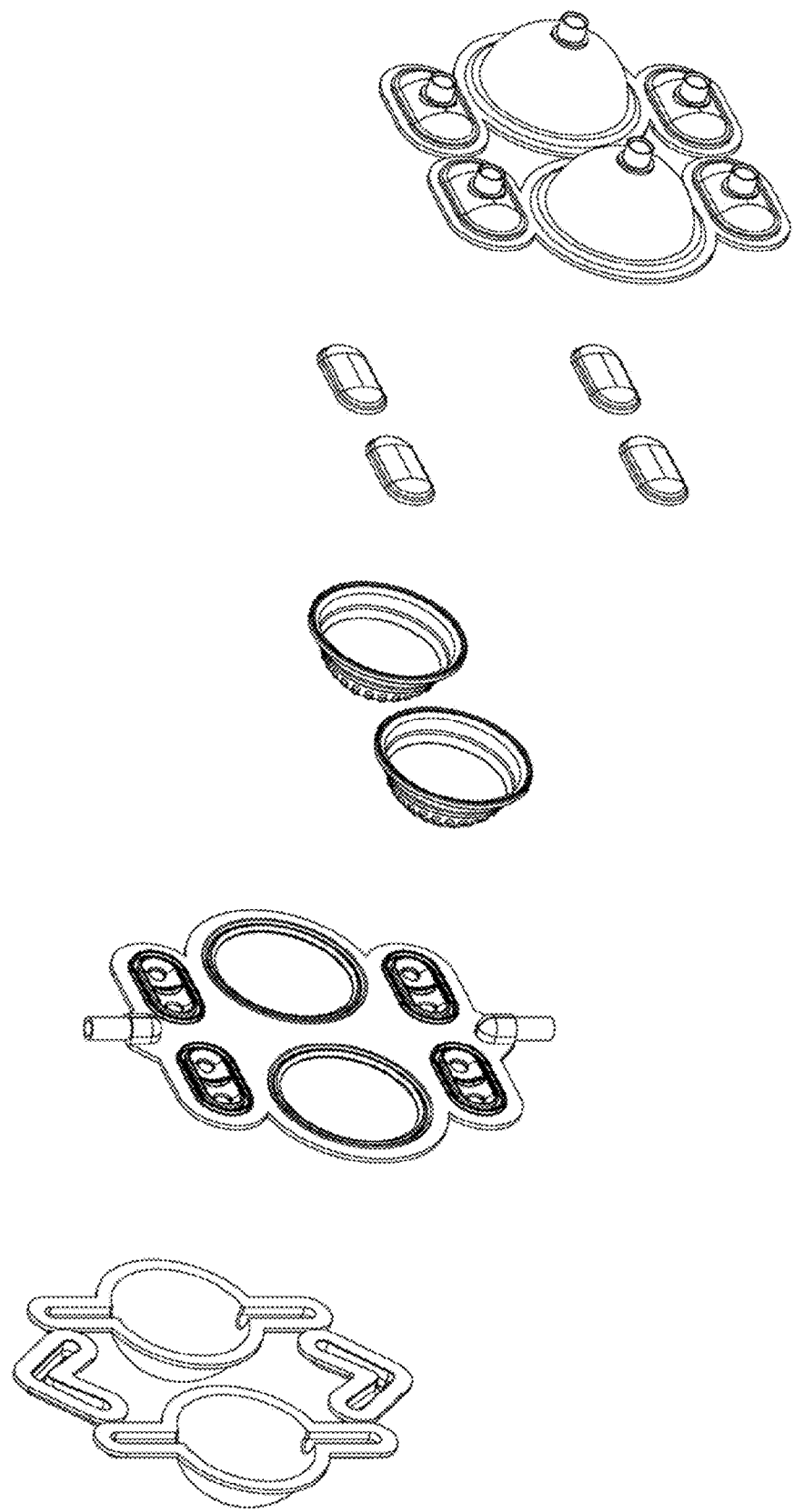
FIG. 26D is an exploded view of the assembled alternate embodiment of the cassette.

Referring next to FIGS. 25A-25B, the alternate embodiment of the bottom plate 1100 is shown. Again, comparing this alternate embodiment to the exemplary embodiment shown in FIGS. 11A-11B, in FIGS. 11A and 11B, the bottom plate 1100 is one solid part. However, referring again to FIGS. 25A-25B, the bottom plate 1100 is two separate parts 1100a, 1100b. In manufacture, the two plates are laser welded or ultrasonically welded individually onto the air side of the midplate (shown in FIGS. 24C-24D). Referring now to FIG. 27A, the multi-piece construction of the top plate 900a, 900b and the bottom plate 1100a, 1100b are readily shown. FIG. 27B additionally shows the separate construction of the top plate 1100a, 1100b.

5.1 Exemplary Embodiments of the Pumping Cassette

In practice, the cassette may be used to pump any type of fluid from any source to any location. The types of fluid include nutritive, nonnutritive, inorganic chemicals, organic chemicals, bodily fluids or any other type of fluid. Additionally, fluid in some embodiments includes a gas, thus, in some embodiments; the cassette is used to pump a gas.

The cassette serves to pump and direct the fluid from and to the desired locations. In some embodiments, outside pumps pump the fluid into the cassette and the cassette pumps the fluid out. However, in some embodiments, the pod pumps serve to pull the fluid into the cassette and pump the fluid out of the cassette.

As discussed above, depending on the valve locations, control of the fluid paths is imparted. Thus, the valves being in different locations or additional valves are alternate embodiments of this cassette. Additionally, the fluid lines and paths shown in the figures described above are mere examples of fluid lines and paths. Other embodiments may have more, less and/or different fluid paths. In still other embodiments, valves are not present in the cassette.

The number of pod pumps described above may also vary depending on the embodiment. For example, although the exemplary and alternate embodiments shown and described above include two pod pumps, in other embodiments, the cassette includes one. In still other embodiments, the cassette includes more than two pod pumps. The pod pumps can be single pumps or work in tandem to provide a more continuous flow. Either or both may be used in various embodiments of the cassette.

The term inlet and outlet, are used interchangeable. A fluid can flow "in" the outlet and "out" the inlet. Additional inlets/outlets ("ports") can be added. Additional ports may be provided to impart particular fluid paths onto the cassette. These additional ports are not necessarily all used all of the time, instead, the variety of ports provide flexibility of use of the cassette in practice.

The pumping cassette can be used in a myriad of applications. However, in one exemplary embodiment, the pumping cassette is used to pump blood from a patient to a dialyzer outside of the cassette and then provide enough pumping force for the blood to travel through the dialyzer and back to the patient through a line outside of the cassette.

The exemplary embodiment includes two pod pumps, a blood inlet, a blood outlet and a heparin metering pump. The valves are smooth valves as described above with respect to FIG. 2D. In the exemplary embodiment, the pod pump membrane is a dimpled membrane as shown in FIGS. 4E-4F.

The blood pump cassette supports both dual-needle and single-needle operation. When operating with two needles the chambers take turns filling and delivering so the blood flow is effectively continuous in both lines. When operating with a single needle the pump will first fill both pump chambers through the arterial line and then deliver to the venous line.

Referring now to FIGS. 12C and 12D, in the exemplary embodiment, the fluid or blood inlet line is oriented on the bottom 810 and the fluid or blood outlet is on the top 824. Thus, in practice, the blood pump cassette may be oriented such that normal therapy flow is up through the pump chambers, exiting at the top. In this embodiment, substantially all or all air entering the blood pump cassette is pushed on toward the dialyzer. However, in other embodiments, the blood inlet line is oriented on the top.

In this exemplary embodiment, the metering pump is a heparin pump and is a single chamber FMS meter pump that takes measured quantities of heparin from a vial or container and delivers it into the blood circuit/fluid line. This feature allows the blood pump cassette to manage the heparin prescription.

Some embodiments may include an air trap within the fluid lines and/or at least one sensor element. The sensor element can be any sensor element having a capability to determine any fluid or non fluid sensor data. In one embodiment; three sensor elements are included in a single fluid line. In some embodiments, more than one fluid line includes the three sensor elements. In the three sensor element embodiment, two of the sensor elements are conductivity sensors and the third sensor element is a temperature sensor. The conductivity sensor elements and temperature sensor elements can be any conductivity or temperature sensor element in the art. In one embodiment, the conductivity sensor elements are graphite posts. In other embodiments, the conductivity sensor elements are posts made from stainless steel, titanium, platinum or any other metal coated to be corrosion resistant and still be electrically conductive. The conductivity sensor elements will include an electrical lead that transmits the probe information to a controller or other device. In one embodiment, the temperature sensor is a thermister potted in a stainless steel probe. However, in alternate embodiments, a combination temperature and conductivity sensor elements is used similar to the one described in U.S. patent application entitled Sensor Apparatus Systems, Devices and Methods, Ser. No. 11/871,821, filed Oct. 12, 2007 and published as U.S. Patent Application Publication No. US2008/0240929 on Oct. 2, 2008. In alternate embodiments, there are either no sensors in the cassette or only a temperature sensor, only one or more conductivity sensors or one or more of another type of sensor.

Although the blood pump cassette embodiment has been described, other embodiments are easily discernable. The metering pump can be used to administer or remove a volume of fluid. Using the FMS, this volume is measured and thus, a substantially accurate (or near substantially accurate) volume of fluid added or removed is known. Other embodiments of this pumping cassette include use of a different membrane or an overmolded membrane or other membranes as described above. Some of the various embodiments of the membrane are described above and shown with respect to FIGS. 4C-6G.

In practice, the cassette may be used to pump any type of fluid from any source to any location. The types of fluid include nutritive, nonnutritive, inorganic chemicals, organic chemicals, bodily fluids or any other type of fluid. Additionally, fluid in some embodiments include a gas, thus, in some embodiments, the cassette is used to pump a gas.

The cassette serves to pump and direct the fluid from and to the desired locations. In some embodiments, outside pumps pump the fluid into the cassette and the cassette pumps the fluid out. However, in some embodiments, the pod pumps serve to pull the fluid into the cassette and pump the fluid out of the cassette.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A pump cassette comprising a fluid flowpath plate and an actuation plate separated by a midplate;
   the fluid flowpath plate comprising a pump fluid chamber wall defining a pump fluid chamber, and comprising a plurality of channels;
   the pneumatic actuation plate comprising a pump actuation chamber wall opposite the fluid pump chamber wall and defining a pump actuation chamber, and comprising a valve actuation chamber wall defining a valve actuation chamber, said pump actuation chamber wall and valve actuation chamber wall each having an actuation port for connection to a source of actuation pressure;
   the midplate having a first side facing the fluid flowpath plate and an opposing second side facing the actuation plate, the first side comprising a surface to enclose and seal the plurality of channels, the second side comprising a valve fluid chamber wall defining a valve fluid chamber, said valve fluid chamber wall having a first fluid port penetrating from the second side to the first side at a first channel of the plurality of channels, and having a second fluid port penetrating from the second side to the first side at a second channel of the plurality of channels;
   the midplate also defining an aperture between the pump fluid chamber wall and the pump actuation chamber wall, the midplate comprising a perimeter groove surrounding the aperture and configured to seat a flexible pump membrane separating the pump fluid chamber from the pump actuation chamber; and
   the midplate also configured to seat a flexible valve membrane separating the valve fluid chamber from the valve actuation chamber.

2. The pump cassette of claim 1, wherein said valve actuation chamber wall is a first valve actuation chamber wall, said valve actuation chamber is a first valve actuation chamber, said valve fluid chamber wall is a first valve fluid chamber wall, and said valve fluid chamber is a first valve fluid chamber;
   the pneumatic actuation plate comprising a second valve actuation chamber wall defining a second valve actuation chamber, and the second side of the midplate comprising a second valve fluid chamber wall defining a second valve fluid chamber, the second valve fluid chamber wall having a first fluid port communicating with a third channel of the plurality of channels and a second fluid port communicating with a fourth channel of the plurality of channels;
   wherein the first channel is in fluid communication with an inlet of the pump cassette, the second channel is in fluid communication with an inlet of the pump fluid chamber, the third channel is in fluid communication with an outlet of the pump fluid chamber, and the fourth channel is in fluid communication with an outlet of the pump cassette.

3. The pump cassette of claim 2, wherein said pump fluid chamber wall is a first pump fluid chamber wall, said pump fluid chamber is a first pump fluid chamber, said pump actuation chamber wall is a first pump actuation chamber wall, and said pump actuation chamber is a first pump actuation chamber;
   the fluid flowpath plate comprising a second pump fluid chamber wall defining a second pump fluid chamber, the pneumatic actuation plate comprising a second pump actuation chamber wall opposite the second fluid pump chamber wall and defining a second pump actuation chamber, and the midplate defining a second aperture between the second pump fluid chamber wall and the second pump actuation chamber wall over which a second flexible pump membrane can be positioned.

4. The pump cassette of claim 3, wherein the pneumatic actuation plate comprises third and fourth valve actuation chamber walls defining third and fourth valve actuation chambers, and the second side of the midplate comprises third and fourth valve fluid chamber walls defining third and fourth valve fluid chambers, the third and fourth valve fluid chamber walls each having a first fluid port communicating with a respective fifth and sixth channel of the plurality of channels and a second fluid port communicating with a respective seventh and eighth channel of the plurality of channels;
   wherein the fifth channel is in fluid communication with the inlet of the pump cassette, the sixth channel is in fluid communication with an inlet of the second pump fluid chamber, the seventh channel is in fluid communication with an outlet of the second pump fluid chamber, and the eighth channel is in fluid communication with the outlet of the pump cassette.

5. The pump cassette of claim 1, wherein the pneumatic actuation plate comprises a metering pump actuation chamber wall defining a metering pump actuation chamber, said metering pump actuation chamber wall having an actuation port for connection to a source of actuation pressure; and wherein
   the midplate second side comprises a metering pump fluid chamber wall defining a metering pump fluid chamber, said metering pump fluid chamber wall having one or more metering pump fluid ports penetrating from the second side to the first side of the midplate at a termination of a metering channel of the plurality of channels.

6. The pump cassette of claim 5, wherein the one or more metering pump fluid ports comprise three metering pump fluid ports, each said metering pump fluid port communicating with a separate metering channel of the plurality of channels.

7. The pump cassette of claim 6, wherein a first metering pump fluid port communicates with a first metering channel connected to a medication container port on the fluid flowpath plate, a first metering valve interposed between the first metering channel and the medication container port.

8. The pump cassette of claim 7, wherein a second metering pump fluid port communicates with a second metering channel connected to a vent port on the fluid flowpath plate, a second metering valve interposed between a first and second portion of the second metering channel.

9. The pump cassette of claim 8, wherein a third metering pump fluid port communicates with a third metering channel connected to an outlet of the pump cassette, a third metering valve interposed between a first and second portion of the third metering channel.

10. A pump cassette comprising a fluid flowpath plate and an actuation plate separated by a midplate;
    the fluid flowpath plate comprising a pump fluid chamber wall defining a pump fluid chamber, and comprising a plurality of channels;
    the pneumatic actuation plate comprising a pump actuation chamber wall opposite the fluid pump chamber wall and defining a pump actuation chamber, and comprising a metering pump actuation chamber wall defining a metering pump actuation chamber, said pump actuation chamber wall and metering pump actuation chamber wall each having an actuation port for connection to a source of actuation pressure;

the midplate having a first side facing the fluid flowpath plate and an opposing second side facing the actuation plate, the first side comprising a surface to enclose and seal the plurality of channels, the second side comprising a metering pump fluid chamber wall defining a metering pump fluid chamber, said metering pump fluid chamber wall having one or more fluid ports penetrating from the second side to the first side, each said one or more fluid ports communicating with a corresponding channel of the plurality of channels;

the midplate also defining an aperture between the pump fluid chamber wall and the pump actuation chamber wall, the midplate comprising a perimeter groove surrounding the aperture and configured to seat a flexible pump membrane separating the pump fluid chamber from the pump actuation chamber; and the midplate also configured to seat a flexible metering pump membrane separating the metering pump fluid chamber from the metering pump actuation chamber.

11. The pump cassette of claim 10, wherein the midplate comprises an inlet and an outlet of the pump cassette, said inlet of the pump cassette being in fluid communication with a first channel of the plurality of channels that is in fluid communication via a first valve with an inlet of the pump fluid chamber, said outlet of the pump cassette being in fluid communication with a second channel of the plurality of channels that is in fluid communication via a second valve with an outlet of the pump fluid chamber.

12. The pump cassette of claim 11, wherein the one of more fluid ports of the metering pump fluid chamber wall comprise a first fluid port communicating with a third channel of the plurality of channels that is in fluid communication via a third valve with the outlet of the pump cassette.

13. The pump cassette of claim 12, wherein the one or more fluid ports of the metering pump chamber wall comprise a second fluid port communicating with a fourth channel of the plurality of channels that is in fluid communication via a fourth valve with a medication container port on the fluid flowpath plate.

14. The pump cassette of claim 13, wherein the one or more fluid ports of the metering pump chamber wall comprise a third fluid port communicating with a fifth channel of the plurality of channels that is in fluid communication via a fifth valve with a vent port on the fluid flowpath plate.

15. The pump cassette of claim 10, wherein said pump fluid chamber wall is a first pump fluid chamber wall, said pump fluid chamber is a first pump fluid chamber, said pump actuation chamber wall is a first pump actuation chamber wall, and said pump actuation chamber is a first pump actuation chamber; and wherein the fluid flowpath plate comprises a second pump fluid chamber wall defining a second pump fluid chamber, the pneumatic actuation plate comprises a second pump actuation chamber wall opposite the second fluid pump chamber wall and defining a second pump actuation chamber, and the midplate defines a second aperture between the second pump fluid chamber wall and the second pump actuation chamber wall over which a second flexible pump membrane can be positioned.

16. The pump cassette of claim 15, wherein the midplate comprises an inlet and an outlet of the pump cassette, said inlet of the pump cassette being in fluid communication with a first channel of the plurality of channels that is in fluid communication via a first valve with an inlet of the first pump fluid chamber, said inlet of the pump cassette being in fluid communication with a second channel of the plurality of channels that is in fluid communication via a second valve with an inlet of the second pump fluid chamber, said outlet of the pump cassette being in fluid communication with a third channel of the plurality of channels that is in fluid communication via a third valve with an outlet of the first pump fluid chamber, and said outlet of the pump cassette being in fluid communication with a fourth channel of the plurality of channels that is in fluid communication via a fourth valve with an outlet of the second pump fluid channel.

17. The pump cassette of claim 16, wherein the one of more fluid ports of the metering pump fluid chamber wall comprise a first fluid port communicating with a fifth channel of the plurality of channels that is in fluid communication via a fifth valve with the outlet of the pump cassette.

18. The pump cassette of claim 17, wherein the one or more fluid ports of the metering pump chamber wall comprise a second fluid port communicating with a sixth channel of the plurality of channels that is in fluid communication via a sixth valve with a medication container port on the fluid flowpath plate.

19. The pump cassette of claim 18, wherein the one or more fluid ports of the metering pump chamber wall comprise a third fluid port communicating with a seventh channel of the plurality of channels that is in fluid communication via a seventy valve with a vent port on the fluid flowpath plate.

20. A pump cassette comprising a fluid flowpath plate and an actuation plate separated by a midplate;

the fluid flowpath plate comprising a pump fluid chamber wall defining a pump fluid chamber, and comprising a plurality of channels;

the pneumatic actuation plate comprising a pump actuation chamber wall opposite the fluid pump chamber wall and defining a pump actuation chamber, comprising a metering pump actuation chamber wall defining a metering pump actuation chamber, and comprising a valve actuation chamber wall defining a valve actuation chamber, said pump actuation chamber wall, metering pump actuation chamber wall, and valve actuation chamber wall each having an actuation port for connection to a source of actuation pressure;

the midplate having a first side facing the fluid flowpath plate and an opposing second side facing the actuation plate, the first side comprising a surface to enclose and seal the plurality of channels, the second side comprising a metering pump fluid chamber wall defining a metering pump fluid chamber, said metering pump fluid chamber wall having one or more metering pump fluid ports penetrating from the second side to the first side, and comprising a valve fluid chamber wall defining a valve fluid chamber, said valve fluid chamber wall having two valve fluid ports, each said metering pump and valve fluid ports communicating with a corresponding channel of the plurality of channels;

the midplate also defining an aperture between the pump fluid chamber wall and the pump actuation chamber wall, the midplate comprising a perimeter groove surrounding the aperture and configured to seat a flexible pump membrane separating the pump fluid chamber from the pump actuation chamber; and the midplate also configured to seat a flexible metering pump membrane separating the metering pump fluid chamber from the metering pump actuation chamber.

* * * * *